US012723087B2

(12) United States Patent
Ramchandren et al.

(10) Patent No.: US 12,723,087 B2
(45) Date of Patent: Sep. 1, 2026

(54) ANTI-FcRn ANTIBODIES AND METHODS FOR TREATING MYASTHENIA GRAVIS

(71) Applicant: Momenta Pharmaceuticals, Inc., Titusville, NJ (US)

(72) Inventors: Sindhu Ramchandren, Spring House, PA (US); Hong Sun, Spring House, PA (US); William Denney, Watertown, MA (US); Santiago Arroyo, Boston, MA (US); Leona E. Ling, Spring House, PA (US); Jocelyn H. Leu, Spring House, PA (US); Jianhua Jin, Belmont, MA (US); Marie-Helene Jouvin, Jamaica Plain, MA (US); Keith Karcher, Titusville, NJ (US); Shawn Black, Spring House, PA (US); Yaowei Zhu, Wayne, PA (US)

(73) Assignee: Momenta Pharmaceuticals, Inc., Titusville, NJ (US)

( * ) Notice: Subject to any disclaimer, the term of this patent is extended or adjusted under 35 U.S.C. 154(b) by 0 days.

(21) Appl. No.: 17/519,811

(22) Filed: Nov. 5, 2021

(65) Prior Publication Data

US 2022/0144946 A1 May 12, 2022

Related U.S. Application Data

(60) Provisional application No. 63/110,884, filed on Nov. 6, 2020, provisional application No. 63/137,972, filed on Jan. 15, 2021, provisional application No. 63/173,126, filed on Apr. 9, 2021, provisional application No. 63/173,919, filed on Apr. 12, 2021, provisional application No. 63/174,423, filed on Apr. 13, 2021, provisional application No. 63/175,440, filed on Apr. 15, 2021, provisional application No. 63/203,075, filed on Jul. 7, 2021, provisional application No. 63/203,077, filed on Jul. 7, 2021, provisional application No. 63/219,155, filed on Jul. 7, 2021.

(51) Int. Cl.

| | |
|---|---|
| ***C07K 16/28*** | (2006.01) |
| ***A61K 47/10*** | (2017.01) |
| ***A61K 47/26*** | (2006.01) |
| ***A61P 21/04*** | (2006.01) |
| *A61K 39/00* | (2006.01) |

(52) U.S. Cl.

CPC ............ *C07K 16/283* (2013.01); *A61K 47/10* (2013.01); *A61K 47/26* (2013.01); *A61P 21/04* (2018.01); *A61K 2039/505* (2013.01); *A61K 2039/545* (2013.01)

(58) Field of Classification Search

CPC ....... C07K 16/283; A61P 21/04; A61K 47/10; A61K 47/26; A61K 2039/505; A61K 2039/545

See application file for complete search history.

(56) References Cited

U.S. PATENT DOCUMENTS

| | | | |
|---|---|---|---|
| 7,662,928 | B2 | 2/2010 | Balthasar et al. |
| 9,943,642 | B2 | 4/2018 | Kondo |
| 10,676,526 | B2 | 6/2020 | Kehry et al. |
| 11,345,751 | B2 | 5/2022 | Ling et al. |
| 11,354,751 | B2 | 6/2022 | Hurry |
| 11,732,047 | B2 | 8/2023 | Kehry et al. |
| 11,773,168 | B2 | 10/2023 | Ling et al. |
| 2005/0053598 | A1 | 3/2005 | Burke et al. |
| 2009/0131639 | A1 | 5/2009 | Kakuta et al. |
| 2009/0297535 | A1 | 12/2009 | Kolkman et al. |
| 2010/0330076 | A1 | 12/2010 | Georgiou et al. |
| 2011/0027262 | A1 | 2/2011 | Das et al. |
| 2011/0059101 | A9 | 3/2011 | Kolkman et al. |
| 2012/0183549 | A1 | 7/2012 | Bradley et al. |
| 2014/0235482 | A1 | 8/2014 | George et al. |
| 2014/0308206 | A1 | 10/2014 | Sexton et al. |
| 2015/0118240 | A1 | 4/2015 | Finney et al. |
| 2015/0157709 | A1 | 6/2015 | Everett et al. |
| 2015/0291689 | A1 | 10/2015 | Padley et al. |

(Continued)

FOREIGN PATENT DOCUMENTS

| | | | |
|---|---|---|---|
| CN | 101124245 | A | 2/2008 |
| CN | 101421297 | A | 4/2009 |

(Continued)

OTHER PUBLICATIONS

Ling Le, et al. M281, an Anti-FcRn Antibody: Pharmacodynamics, Pharmacokinetics, and Safety Across the Full Range of IgG Reduction in a First-in-Human Study. Clin Pharmacol Ther. Apr. 2019;105(4):1031-1039. (Year: 2019).*

Lazaridis K, Tzartos SJ. Autoantibody Specificities in Myasthenia Gravis; Implications for Improved Diagnostics and Therapeutics. Front Immunol. Feb. 14, 2020;11:212. (Year: 2020).*

Roopenian DC, Low BE, Christianson GJ, Proetzel G, Sproule TJ, Wiles MV. Albumin-deficient mouse models for studying metabolism of human albumin and pharmacokinetics of albumin-based drugs. MAbs. 2015;7(2):344-51. (Year: 2015).*

(Continued)

*Primary Examiner* — Aurora M Fontainhas
*Assistant Examiner* — Jennifer A Benavides
(74) *Attorney, Agent, or Firm* — BakerHostetler

(57) ABSTRACT

Methods for dosing antibodies directed to human neonatal Fc receptor (FcRn) are described, wherein said methods comprise administration of anti-FcRn antibodies at an initial loading dose and a maintenance dose. The anti-FcRn antibodies are useful, e.g., to promote clearance of autoantibodies in a subject, to suppress antigen presentation in a subject, to block an immune response, e.g., block an immune complex-based activation of the immune response in a subject, or to treat immunological diseases (e.g., autoimmune diseases) in a subject, such as myasthenia gravis. Pharmaceutical compositions comprising the anti-FcRn antibodies are also described.

18 Claims, 13 Drawing Sheets

Specification includes a Sequence Listing.

(56) References Cited

U.S. PATENT DOCUMENTS

2015/0329628 A1 11/2015 Antochshuk et al.
2016/0194397 A1 7/2016 TenHoor et al.
2017/0209550 A1 7/2017 Kjellman et al.
2018/0016334 A1* 1/2018 Kehry .................... A61P 21/00
2019/0194277 A1 6/2019 de Haard et al.
2020/0003191 A1 1/2020 Ono et al.
2020/0031917 A1* 1/2020 Kraft .................... A61K 47/183
2020/0044731 A1 2/2020 Tsuzaki et al.
2020/0299382 A1 9/2020 Kehry et al.
2021/0299255 A1 9/2021 Zhang et al.
2021/0340251 A1 11/2021 Zhang et al.
2022/0064290 A1 3/2022 Ling et al.
2022/0259308 A1* 8/2022 Arroyo .................. A61P 37/06
2023/0049725 A1 2/2023 Ling et al.
2024/0158508 A1 5/2024 Kehry et al.

FOREIGN PATENT DOCUMENTS

CN 102149729 A 8/2011
CN 103619353 B 3/2014
CN 103717619 A 4/2014
CN 104479017 A 4/2015
CN 106103476 A 11/2016
CN 109790221 A 5/2019
CN 107567460 B 4/2021
EP 2703010 A2 3/2014
EP 3010938 A1 4/2016
EP 3250610 A2 12/2017
EP 3491025 B1 6/2019
JP 06-217791 A 8/1994
JP 2011-088913 A 5/2011
JP 2011523351 A 8/2011
JP 2014523737 A 9/2014
JP 2015163618 A 9/2015
JP 2017516848 A 6/2017
JP 6853178 B2 3/2021
JP 7094941 B2 7/2022
JP 7442575 B2 3/2024
KR 20140036267 A 3/2014
KR 10-2015-0005987 A 1/2015
KR 10-2017-0109020 A 9/2017
WO 93/19785 A1 10/1993
WO 2004041862 A2 5/2004
WO 2005013912 A2 2/2005
WO 2007087289 A3 10/2008
WO 2009124294 A2 10/2009
WO 2009131702 A9 9/2010
WO 2012167039 A1 12/2012
WO 2014019727 A1 2/2014
WO 2014204280 A1 12/2014
WO 2014179601 A3 1/2015
WO 2015100299 A1 7/2015
WO 2015167293 A1 11/2015
WO 2016065323 A2 4/2016
WO 2016123521 A3 9/2016
WO 2016183352 A1 11/2016
WO 2017015622 A2 1/2017
WO 2017/189556 A1 11/2017
WO 2018023136 A1 2/2018
WO 2018/055574 A1 3/2018
WO 2019/070714 A1 4/2019
WO 2019110823 A1 6/2019
WO 2019118791 A1 6/2019
WO 2019160979 A1 8/2019
WO 2019/194277 A1 10/2019
WO 2020/018910 A1 1/2020
WO 2020/023310 A1 1/2020
WO 2020/047029 A1 3/2020
WO WO-2020079086 A1 * 4/2020 ......... A61K 39/3955
WO 2020097099 A1 5/2020
WO 2021/022249 A1 2/2021
WO 2021140202 A1 7/2021
WO 2021257668 A1 12/2021
WO 2022/098955 A1 5/2022
WO 2022221239 A1 10/2022
WO 2022/240875 A1 11/2022

OTHER PUBLICATIONS

Miniaci A, Gupta V. Loading Dose. [Updated Jun. 23, 2022]. In: StatPearls [Internet]. Treasure Island (FL): StatPearls Publishing; Jan. 2022. Available from: https://www.ncbi.nlm.nih.gov/books/NBK557418/ (Year: 2022).*

Tosi et al. Clinical Development Strategies and Outcomes in First-in-Human Trials of Monoclonal Antibodies. J Clin Oncol. Jul. 1, 2015;33(19):2158-65. (Year: 2015).*

Casipit et al., "Improving the Binding Affinity of an Antibody using Molecular Modeling and Site-Directed Mutagenesis," Protein Science, Aug. 1, 1998, 7:1671-1680.

Chen et al., "Enhancement and destruction of antibody function by somatic mutation: unequal occurrence is controlled by V gene combinatorial associations", The EMBO Journal (1995) vol. 14 No. 12, pp. 2784-2794.

Chien et al., "Significant structural and functional change of an antigen-binding site by a distant amino acid substitution: Proposal of a structural mechanism,", Proc. Natl. Acad. Sci. USA, 1989, 86(14): 5532-5536.

Christensen, D et al., Trehalose preserves DDA/TDB liposomes and their adjuvant effect during freeze-drying, Biochimica et Biophysica Acta., Sep. 2007, Epub May 13, 2007, vol. 1768, No. 9, pp. 2120-2129.

Christianson et al., "Monoclonal antibodies directed against human FcRn and their applications," MAbs, 2012, 4(2):208-216.

Committee on Obstetric Practice American Institute of Ultrasound in Medicine Society for Maternal-Fetal Medicine, "Committee Opinion. Number 700: Methods for Estimating the Due Date," Obstetrics & Gynecology, May 2017, 129(5): e150-e154.

Ellinger et al., "Overexpression of the human neonatal Fc-receptor alpha-chain in trophoblast-derived BeWo cells increases cellular retention of beta2-microglobulin," Placenta., 2005, 26(2-3): 171-182.

Hiroyuki et al., "Tryptophan H33 plays an important role in pyrimidine (6-4) pyrimidone photoproduct binding by a higli-affinity antibody," Protein Engineering, 1999, 12(10): 879-884.

Hoftman et al., "Newborn illnesses caused by transplacental antibodies," Adv. Pediatr., 2008, 55: 271-304.

Hutson et al., "The human placental perfusion model: a systematic review and development of a model to predict in vivo transfer of theraeputic drugs," Clin. Pharmacol. Ther., 2011, 90(1): 67-76.

International Preliminary Report on Patentability in International Application No. PCT/US2017/044765, dated Jan. 29, 2019, 9 pages.

International Preliminary Report on Patentability in International Application No. PCT/US2018/065568, dated Jun. 16, 2020, 10 pages.

International Preliminary Report on Patentability in International Applications No. PCT/US2016/015720, dated Aug. 1, 2017.

International Search Report and Written Opinion in International Application No. PCT/US16/15720, dated Jul. 26, 2016.

International Search Report and Written Opinion in International Application No. PCT/US2017/44765, dated Jan. 9, 2018, 14 pages.

International Search Report and Written Opinion in International Application No. PCT/US2019/042597, dated Nov. 26, 2019.

International Search Report and Written Opinion in International Application No. PCT/US2019/042615, dated Nov. 15, 2019.

International Search Report and Written Opinion in International Application No. PCT/US2020/044731, dated Dec. 22, 2020.

International Search Report and Witten Opinion in International Application No. PCT/US2018/065568, dated Apr. 2, 2019, 14 pages.

Junghans and Anderson, "The protection receptor for lgG catabolismis the beta2-microglobulin-containing neonatal intestinal transport receptor," PNAS, May 1996, 93:5512-5516.

Kobrin et al., "A V Region Mutation in Phosphocholine-Binding Monoclonal Antibody Results in Loss of Antigen Binding,", J. of Immunol., Mar. 15, 1991, 146(6): 2017-2020.

(56) References Cited

OTHER PUBLICATIONS

Kussie et al., "A Single Engineered Amino Acid Substitution Changes Antibody Fine Specificity", Journal of Immunology (1994) 152(1): pp. 146-152.
Li et al., "The Maternal Immune Response to Fetal Platelet GPibalpha Causes Frequent Miscarriage in Mice That Can Be Prevented by Intravenous lgG and anti-FcRn Therapies," J. Clin. Invest., Nov. 2011, 121(11): 4537-4547.
Ling et al., "32: M281, an anti-FcRn antibody, inhibits lgG transfer in a human ex-vivo placental perfusion model," Jan. 2019, 220(1): 32.
Ling et al., "M281: A Therapeutic Anti-FcRn Blocking Antibody for Rapid Clearance of lgG and lgG Autoantibodies in Immune Cytopenias and Other Auto/Allm-Immune Disease", Blood (2015) 126, 23: 3472.
Liu et al., "Amelioration of Experimental Autoimmune Myasthenia Gravis in Rats by Neonatal FcR Blockage," J. of Immunol., Apr. 15, 2007, 178(8): 5390-5398.
Mahadevan eta l., "Placental transfer of anti-tumor necrosis factor agents in pregnant patients with inflammatory bowel disease," Clin. Gastroenterol. Hepatol., 2013, 11(3): 286-292.
Maleck, "Ex vivo human placenta models: transport of immunoglobulin G and its subclasses, " Vaccine, 2003, 21: 3362-3364.
Mathiesen eta l., "Quality assessment of a placental perfusion protocol," Reproductive Toxicology, 2010, 30: 138-146.
Montes, T et al., Genetic Modification of the Penicillin G Acylase Surface to Improve its Reversible Immobilization on Ionic Exchangers, Applied and Encironmental Microbiology, Jan. 2007, Epub Nov. 10, 2006, vol. 73, No. 1, pp. 312-319.
Morgan et al., "The effect of intravenous immunoglobulin on placental transfer of a platelet-specific antibody: Anti-P1A1," Transfusion Medicine, 1991, 1: 209-216.
Mørck et al., "Placental transport and in vitro effects of Bisphenol A," Reproductive Toxicol., 2010, 30: 131-137.
Nanovskaya et al., "Transplacental Transfer and Metabolism of Buprenophine," J. Pharmacol. Exp. Ther., 2002, 300 (1): 26-33.
Nonfinal Office Action mailed Jun. 29, 2021 received in U.S. Appl. No. 16/321,801.
Panka et al., "Defining the Structural Correlates Responsible for Loss of Arsonate Affinity in an IDCR Antibody Isolated From an Autoimmune Mouse," Mol. Immunol.,I Aug. 1, 1993, 30(11): 1013-1020.
Porter et al., "Certolizumab pegol does not bind the neonatal Fc receptor (FcRn): Consequences for FcRn-mediated in vitro transcytosis and ex vivo human placental transfer," J. Repro. Imm., 2016, 116: 7-12.
Roopenian et al., "Clinical Ramifications of the MHC Family Fc Receptor FcRn," J. Clin. Immunol., 2010, 30(6): 790-797.
Roopenian et al., "FcRn: the neonatal Fc receptor comes of age," Nature Immunol., 2007, 7: 715-25.
Rudikoff et al., "Single Amino Acid Substitution Altering Antigen-Binding Specificity," Proc. Natl. Acad. Sci. USA, Mar. 1, 1982, 79: 1979-1983.
Schildbach et al., "Modulation of antibody affinity by a non-contact residue," Protein Science, 1993, 2: 206-214.
Schneider et al., "Effect of flow rate ratio on the diffusion of antipyrine and 3H20 in the isolated dually in vitro perfused lobe of the human placenta," Contrib. Gynecol. Obstet., 1985, 13: 114-123.
Schneider et al., "Transfer across the perfused human placenta of antipyrine, sodium and leucine," Am. J. Obstet. Gynecol., 1972, 114: 822-828.
Singapore Search Report and Written Opinion in Singapore Application No. 11201705475Q, dated Jul. 31, 2018.
Urbaniak et al., "Transfer of anti-D antibodies across the isolated perfused human placental lobule and inhibition by high dose intravenous immunoglobulin: a possible mechanism of action," Br. J. Hematol., 1997, 96: 186-93.
Urbaniak et al., "Variable inhibition of placental lgG transfer in vitro with commercial IVgG preparations," Br. J. Haematol., 1999, 107: 815-817.
Whittamker, MM et al., Burst Kinetics and Redoc Transformations of the Active Site Manganesse Ion in Oxalate Oxidase: Implications for the Catalytic Mechanism, The Journal of Biological Chemistry, Mar. 9, 2007, Epub Jan. 8, 2007, vol. 282, No. 10, pp. 7011-7023.
Winkler et al., "Changing the Antigen Binding Specificity by Single Point Mutations of an Anti-p24 (HIV-1) Antibody," J. of Immunol., Oct. 15, 2000, 165(8): 4505-4514.
Zhu et al., "MHC class I-related neonatal Fc receptor for lgG is functionally expressed in monocytes, intestinal macrophages, and dendritic cells," J. Immunol., 2001, 166(5): 3266-3276.
Nonfinal Office Action mailed Jan. 22, 2022 received in U.S. Appl. No. 16/771,147.
Notice of Allowance mailed Jan. 28, 2022 received in U.S. Appl. No. 16/321,801.
International Search Report and Written Opinion in International Application No. PCT/US2021/058188, dated Apr. 5, 2022.
Singapore Search Report and Written Opinion in Application No. 10202007232W, dated Feb. 17, 2022.
Extended European Search Report Application No. EP19840429. mailed Mar. 18, 2022.
Wang, et al., "Antibody Structure, Instability, and Formulation", Journal of Pharmaceutical Sciences, (2007) vol. 96, No. 1.
Warne et al., "Development of high concentration protein biopharmaceuticals: The use of platform approaches in formulation development", European Journal of Pharmaceutics and Biopharmaceutics (2011) 78: pp. 208-212.
Daugherty et al., "Formulation and Delivery Issues for Monoclonal Antibody Therapeutics", Current Trends In Monoclonal Antibody Development and Manufacturing (2010) pp. 103-129.
Sharma et al., "The Formulation and Delivery of Monoclonal Antibodies", Therapeutic Monoclonal Antibodies: From Bench to Clinic (2009) pp. 1-37.
Kortt et al., "Dimaric and trimeric antibodies: high avidity scFvs for cancer targeting", Biomolecular Engineering (2001) 18; 95-108.
Nonfinal Office Action mailed Aug. 5, 2022 received in U.S. Appl. No. 16/771,147.
Buyon et al., "Autoimmune associated congential heart block: integration of clinical and research clues in the management of the maternal/foetal dyad at risk", Journal of Internal Medicine (2009) 265: 653-662.
Hui-Juan et al., "Prokaryotic expression of porcine FcRn-CT and prepartion of polyclonal antibody", Chinese Journal of Vetenary Science (2012) vol. 32, No. 2, pp. 262-271.
Tannemaat et al., "Emerging therapies for autoimmune myasthenia gravis: Towards treatment without corticosteroids", Neuromuscular Disorders (2020 30: pp. 111-119.
International Search Report and Witten Opinion in International Application No. PCT/US2022/024354, dated Sep. 12, 2022.
Notice of Allowance mailed Nov. 22, 2022 received in U.S. Appl. No. 16/825,066.
Deng et al., "Neonatal Alloimmune Thrombocytopenia Associated with Maternal HLA Antibodies," Chinese Journal Of Blood Transfusion (Sep. 2016) vol. 29, No. 9, pp. 935-937.
European Search Report for European Patent Application No. 16744204.5 dated Jul. 24, 2018.
International Preliminary Report on Patentability for International PCT Application No. PCT/US2019/042615 dated Feb. 4, 2021.
Wilcox et al., "Review of Transplacental Antibody Transfer," Frontiers in Immunology (Oct. 2017) vol. 8, Art. 1294, pp. 1-12.
Kang et al., "Rapid Formulation Development for Monoclonal Antibodies," BioProcess International (Apr. 2016) pp. 1-7.
European Search Report for European Patent Application No. 19838652.6 dated Nov. 10, 2022.
European Search Report for European Patent Application No. 20846154.1 dated Jul. 19, 2023.
International Preliminary Report on Patentability for International PCT Application No. PCT/US2019/042597 dated Feb. 4, 2021.
International Preliminary Report on Patentability for International PCT Application No. PCT/US2020/044731 dated Feb. 10, 2022.
International Preliminary Report on Patentability for International PCT Application No. PCT/US2021/058188 dated May 19, 2023.
European Search Repot for European Patent Application No. 17835436.1.

(56) References Cited

OTHER PUBLICATIONS

Akilesh et al., "The MHC class I-like Fc receptor promotes humorally mediated autoimmune disease," J Clin Invest (2004) 113(9): 1328-1333.
Chung et al., "Effects of Antibody Disulfide Bond Reduction on Purification Process Performance and Final Drug Substance Stability," Biotechnol. Bioeng. (Jun. 2017) vol. 114, No. 6, pp. 1264-1274.
Ling et al., "Targeting the Neonatal Fc Receptor (FcRn) to Mediate Autoantibody Clearance in lgG-Driven Autoimmune Disease," Momenta Pharmaceuticals, Inc., Abstract THU0057, Presented at the Annual European Congress of Rheumatology, Jun. 10-13, 2015.
Zuercher et al., "Next-Generation Fc Receptor-Targeting Biologics for Autoimmune Diseases," Autoimmunity Reviews (2019) vol. 18, No. 10, Art. 102366, pp. 1-9.
Qin, "Modern Surgery for Obstetric and Gynecological Diseases," Scientific Technical Documentation Press, 1st edition (2017) p. 172.
Vlasak et al., "Fragmentation of Monoclonal Antibodies," mAbs. (2011) 3(3) pp. 253-663.
International Preliminary Report on Patentability for International PCT Application No. PCT/US2022/024354 dated Oct. 26, 2023.
Yu et al., "Estimation of Hemolytic Disease of the Newborn in the United States from 1996-2010," Momenta Pharmaceuticals, Inc. (2021).
Zdravic et al., "Fetal and neonatal alloimmune thrombocytopenia", Seminars in Fetal & neonatal Medicine (2016) 21; pp. 19-27.
Roy et al., "M281, an Anti-FcRn Antibody, Inhibits lgG Transfer in a Human Ex Vivo Placental Perfusion Model," American Journal of Obstetrics & Gynecology (May 2109) 498.e1-e9.
Antozzi et al., "A Phase 2, Multicenter, Randomized, Double-Blind, Placebo-Controlled Study to Evaluate the Safety, Tolerability, Efficacy, Pharmacokinetics, Pharmacodynamics, and Immunogenicity of Nipocalimab Administered to Adults with Generalized Myathenia Gravis," Poster Presented at the 16th International Congress on Neuromuscular Diseases (Virtual), May 21-22 & 28-29, 2021.
Choudhury, "Mode of Nipocalimab Action, PK-PD-Efficacy from Cells to Patients," FcRn-Targeted Therapies for Autoimmune Disorders Online Event, Mar. 23-25, 2021, pp. 1-23.
Brown et al., "Tolerance to Single, but Not Multiple, Amino Acid Replacements in Antibody VH CDR2," Journal of Immunology (1996), vol. 156, pp. 3285-3291.
Vajdos et al., "Comprehensive Functional Maps of the Antigen-binding Site of an Anti-ErbB2 Antibody Obtained with Shotgun Scanning Mutagenesis," Journal of Molecular Biology (2002), vol. 320, pp. 415-428.
Liu, "Medical Immunology," China Press of Traditional Chinese Medicine, 1st edition (2008) p. 28.
"Vivacity-MG Phase 2 Interim Analysis Topline Results," Momenta Pharmaceuticals, Inc., (2020) pp. 1-22.
Guptill, "Vivacity-MG: A Phase 2, Multicenter, Randomized, Double-Blind, Placebo-Controlled Study to Evaluate the Safety, Tolerability, Efficacy, Pharmacokinetics, Pharmacodynamics, and Immunogenicity of Nipocalimab Administered to Adults with Generalized Myasthenia Gravis," American Academy of Neurology, Virtual Meeting, Apr. 17-22, 2021.
Guptill et al., "Vivacity-MG: A Phase 2, Multicenter, Randomized, Double-Blind, Placebo-Controlled Study to Evaluate the Safety, Tolerability, Efficacy, Pharmacokinetics, Pharmacodynamics, and Immunogenicity of Nipocalimab Administered to Adults with Generalized Myasthenia Gravis," Momenta Pharmaceuticals, Inc., 164, Presented at the American Association of Neuromuscular & Electrodiagnostic Medicine (AANEM) 2929 Virtual Annual Meeting, Oct. 7-10, 2020.
Guptill et al., "Phase 2 Trial Evaluating the FcRn Antagonist Nipocalimab in Adults with Generalized Myasthenia Gravis," Momenta Pharmaceuticals, Inc., Presented at the 16th International Congress on Neuromuscular Diseases, Virtual Worldwide, May 21-22 & 28-29, 2021.
Edelman et al., "The Covalent Structure Of An Entire Gimmunoglobulin Molecule," Proc. Natl. Acad. USA (1969) 63, pp. 78-85.
Extended European Search Report for European Patent Application No. 23189767.9 dated Jan. 17, 2024.
Extended European Search Report for European Patent Application No. 23195791.1 dated Jan. 17, 2024.
Haberger et al., "Rapid characterization of biotherapeutic proteins by size-exclusion chromatography coupled to native mass spectrometry," MABS (2016) vol. 8(2), pp. 331-339.
Ling et al., "Nipocalimab's Selective Targeting of FcRn and lgG Clearance Preserves Key Immune Functions," American Academy of Neurology Annual Meeting, Apr. 24-26, 2022, pp. 1-12.
McCrae et al., "Identification of a Warm Autoimmune Hemolytic Anemia (wAIHA) Population Using Predictive Analytics of a Known Clinically Profiled Cohort," Momenta Pharmaceuticals, Inc., 2021, pp. 1-9.
McCrae et al., "Identification of a Warm Autoimmune Hemolytic Anemia (wAIHA) Population Using Predictive Analytics of a Known Clinically Profiled Cohort," Presented at the European Hematology Association (EHA), Virtual, Jun. 9-17, 2021, 1 page.
Murakhovskaya et al., "Study Design of a Phase 2/3, Randomized, Double-Blind, Placebo-Controlled Study to Assess the Efficacy and Safety of Nipocalimab, an FcRn Antagonist, in Warm Autoimmune Haemolytic Anaemia (wAIHA)," Presented at the European Hematology Association (EHA), Virtual, Jun. 9-17, 2021.
Zhang et al., "Real-World Resource Utilization and Productivity Loss Among Patients with Myasthenia Gravis in Sweden: A Nationwide Population-Based Study," Presented at the American Academy of Neurology, Apr. 24-26, 2022, pp. 1-13.
Anonymous: "A Study of Nipocalimab in Children Aged 2 to Less Than 18 Years With Generalized Myasthenia Gravis", NCT05265273, Retrieved from https://clinicaltrials.gov/study/NCT05265273, Mar. 25, 2025, pp. 1-16.
Castleman et al., "Medical therapy to attenuate fetal anaemia in severe maternal red cell alloimmunisation", British Journal of Haematology, vol. 192, No. 3, Aug. 14, 2020, pp. 425-432.
Intravenous Immune Globulin (IVIG) Guideline, Intravenous Immune Globulin (IVIG) Administration in Neonates, ACTS Practice Committee, IVIG HDS Version May 10, 2007, 3pp.
Li et al., "The Maternal Immune Response to Fetal Platelet GPlba Causes Frequent Miscarriage in Mice That Can Be Prevented by Intravenous lgG and anti-FcRn Therapies," J. Clin. Invest., Nov. 2011, 121(11): 4537-4547.
Ling et al., "M281, an Anti-FcRn Antibody: Pharmacodynamics, Pharmacokinetics and Safety across the Full Range of lgG Reduction in a First-In-Human Study, Supplementary Materials", Apr. 1, 2019 (Apr. 1, 2019), XP093187207, DOI: https://doi.org/10.1002/cpt.1276, Retrieved from: URL:https://ascpt.onlinelibrary.wiley.com/action/downloadSupplement?doi=10.1002/cpt.1276&file=cpt1276-sup-0001-Supinfo.pdf.
Munot et al., "242nd ENMC International Workshop: Diagnosis and management of juvenile myasthenia gravis Hoofddorp, the Netherlands, Mar. 1-3, 2019", Neuromuscular Disorders, vol. 30, 2020, pp. 254-264.
O'Connell et al., "Management of Juvenile Myasthenia Gravis", Front. Neurol., vol. 11, Article 743, Jul. 2020, pp. 1-12.
RA | How to Prepare for RITUXAN® (rituximab) Infusions, Rituzan, accessed https://www. rituxan.com/ra/treatment/preparing.html, on Jan. 2, 2024, 1pp.
Simister et al., "Placental transport of immunoglobulin G, Vaccine", 21:3365-3369, 2003.

* cited by examiner

Abbreviations: FcRn = neonatal Fc receptor; SD = standard deviation.

Abbreviations: IgG = immunoglobulin G; SD = standard deviation.

Label
30mg/kg Q2W
60 mg/kg and 2 weeks later 15 mg/kg Q2W

Baseline MG-ADL Change from (Placebo corrected)
0
-1
-2
0
1
2
3
4
Time, weeks

ANTI-FcRn ANTIBODIES AND METHODS FOR TREATING MYASTHENIA GRAVIS

CROSS-REFERENCE TO RELATED APPLICATIONS

This application claims priority to U.S. Provisional Application No. 63/110,884, filed Nov. 6, 2020, U.S. Provisional Application No. 63/137,972, filed Jan. 15, 2021, U.S. Provisional Application No. 63/173,126, filed Apr. 9, 2021, U.S. Provisional Application No. 63/173,919, filed Apr. 12, 2021, U.S. Provisional Application No. 63/174,423, filed Apr. 13, 2021, U.S. Provisional Application No. 63/175,440, filed Apr. 15, 2021, U.S. Provisional Application No. 63/203,075, filed Jul. 7, 2021, U.S. Provisional Application No. 63/203,077, filed Jul. 7, 2021, U.S. Provisional Application No. 63/219,155, filed Jul. 7, 2021, each of which is hereby incorporated by reference in its entirety.

BACKGROUND

Therapeutic proteins, e.g., therapeutic antibodies, have rapidly become a clinically important drug class for patients with immunological diseases. Numerous autoimmune and alloimmune diseases are mediated by pathogenic antibodies. There exists a need for novel methods of treating immunological diseases.

SUMMARY

The present disclosure features methods for dosing of antibodies to human neonatal Fc receptor (FcRn). The anti-FcRn antibodies are useful, e.g., to promote clearance of autoantibodies in a subject, to suppress antigen presentation in a subject, to block an immune response, e.g., block an immune complex-based activation of the immune response in a subject, or to treat immunological diseases (e.g., autoimmune diseases) in a subject.

Described herein are methods of treating various disorders comprising intravenous or subcutaneous administration of about 15 mg/kg to about 60 mg/kg dose of an anti-FcRn antibody as described herein to a subject. The methods described herein can include an initial administration (e.g., a loading dose or induction) at a first dose level followed by subsequent administrations at a different or maintenance dose level.

In some embodiments, methods of treating myasthenia gravis in a patient in need thereof, the method comprising administering an initial loading dose of about 30 mg/kg mg/kg to about 60 mg/kg of an anti-FcRn antibody followed by administering a maintenance dose of about 15 mg/kg to about 30 mg/kg of the anti-FcRn antibody, wherein the anti-FcRn antibody comprises a heavy chain comprising a HCDR1 of SEQ ID NO: 6, a HCDR2 of SEQ ID NO: 7, and a HCDR3 of SEQ ID NO: 8; and a light chain comprising a LCDR1 of SEQ ID NO: 3, a LCDR2 of SEQ ID NO: 4, and a LCDR3 of SEQ ID NO: 5; wherein the administration reduces serum IgG in the patient by at least 10%, at least 20%, at least 30%, at least 40%, at least 50%, at least 60%, at least 70%, at least 80%, or at least 90% of baseline serum IgG are provided.

In some embodiments, methods of treating myasthenia gravis in a patient in need thereof, the method comprising administering an initial loading dose of about 30 mg/kg mg/kg to about 60 mg/kg of an anti-FcRn antibody followed by administering a maintenance dose of about 15 mg/kg to about 30 mg/kg of the anti-FcRn antibody, wherein the anti-FcRn antibody comprises a heavy chain comprising a HCDR1 of SEQ ID NO: 6, a HCDR2 of SEQ ID NO: 7, and a HCDR3 of SEQ ID NO: 8; and a light chain comprising a LCDR1 of SEQ ID NO: 3, a LCDR2 of SEQ ID NO: 4, and a LCDR3 of SEQ ID NO: 5; wherein the administration reduces serum autoantibodies by at least 95%, at least 90%, at least 85%, at least 80%, at least 75%, at least 50%, or at least 25% of baseline serum autoantibodies are provided.

In some embodiments, methods of treating or reducing severity of myasthenia gravis in a subject, the method comprising administering to the subject an initial loading dose of about 5 mg/kg mg/kg to about 120 mg/kg of the anti-FcRn antibody followed by administering a maintenance dose of about 5 mg/kg to about 60 mg/kg of an anti-FcRn antibody, wherein the anti-FcRn antibody comprises a heavy chain comprising a HCDR1 of SEQ ID NO: 6, a HCDR2 of SEQ ID NO: 7, and a HCDR3 of SEQ ID NO: 8; and a light chain comprising a LCDR1 of SEQ ID NO: 3, a LCDR2 of SEQ ID NO: 4, and a LCDR3 of SEQ ID NO: 5, are provided.

In some embodiments, pharmaceutical compositions comprising an anti-FcRn antibody for administration to a patient suffering from myasthenia gravis, wherein the anti-FcRn antibody is administered to the patient at an initial loading dose of about 30 mg/kg mg/kg to about 60 mg/kg followed by administering a maintenance dose of about 15 mg/kg to about 30 mg/kg of the anti-FcRn antibody; and the anti-FcRn antibody comprises a heavy chain comprising a HCDR1 of SEQ ID NO: 6, a HCDR2 of SEQ ID NO: 7, and a HCDR3 of SEQ ID NO: 8; and a light chain comprising a LCDR1 of SEQ ID NO: 3, a LCDR2 of SEQ ID NO: 4, and a LCDR3 of SEQ ID NO: 5, are provided.

DETAILED DESCRIPTION

Definitions

Figure 1:
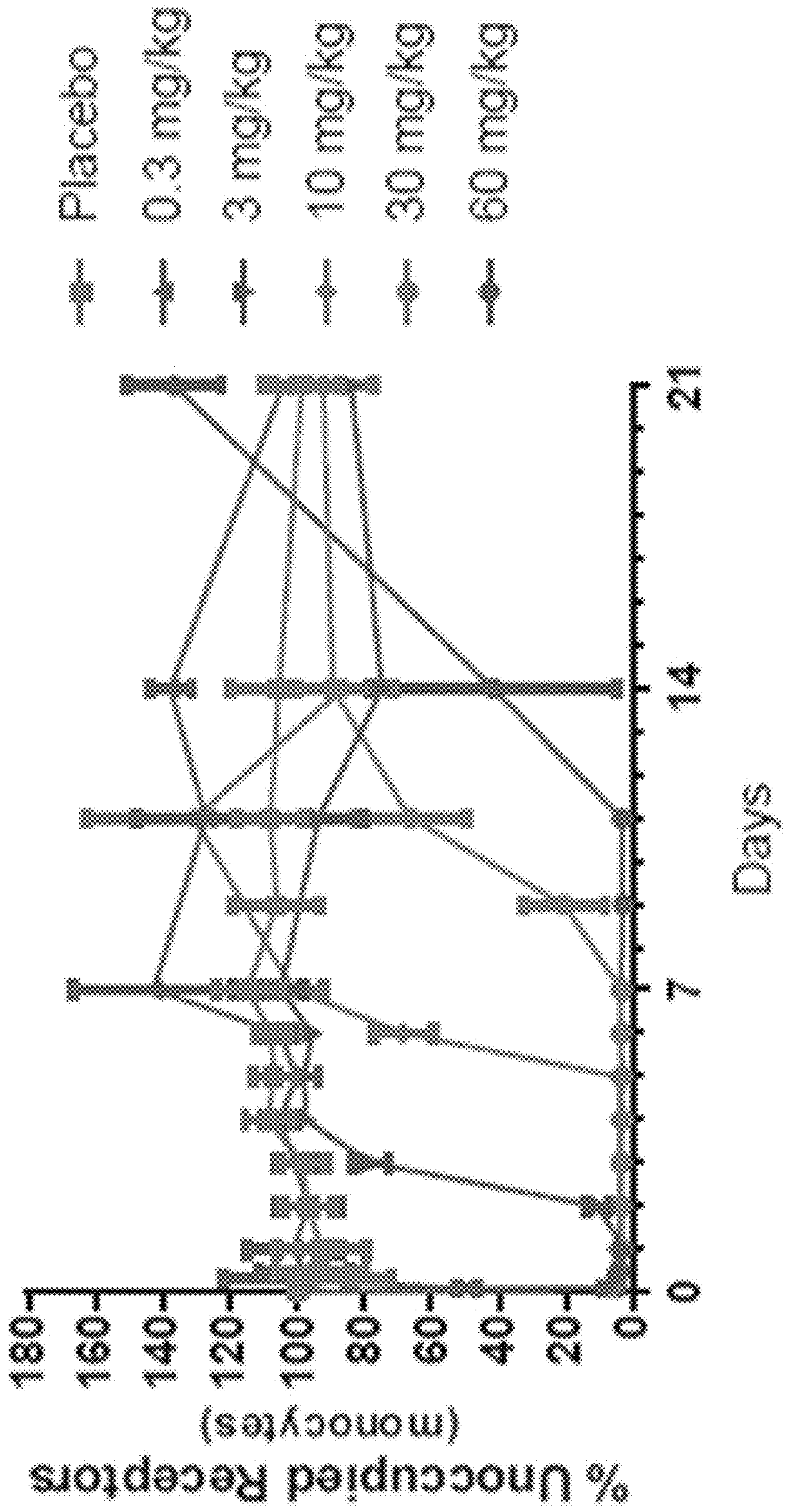
FIG. 1 is a graph showing mean (SD) FcRn receptor occupancy in circulating monocytes following single doses of 0.3 mg/kg, 3 mg/kg, 10 mg/kg, 30 mg/kg, and 60 mg/kg of M281.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by +/−10% and remain within the scope of the disclosed embodiments. Additionally, although a value may be preceded by the term "about" the exact value is also provided for herein, i.e., without the term "about."

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit FcRn antigen-binding activity.

"Antibody fragments" comprise a portion of an intact antibody, including the antigen binding or variable region of the intact antibody. Examples of antibody fragments include Fab, Fab', $F(ab')_2$, and Fv fragments, diabodies, linear antibodies, single-chain antibody molecules, and multispecific antibodies.

As used herein, the term "isolated antibody" refers to an antibody which has been separated and/or recovered from a component of its manufacturing host cell environment. Contaminant components of its manufacturing host cell environment are materials which would interfere with research, diagnostic, or therapeutic uses of the antibody. Contaminant components may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or non-reducing conditions using, for example, Coomassie blue or silver stain. An isolated antibody includes the antibody in situ within recombinant cells. Ordinarily, however, an isolated antibody will be prepared by at least one purification step. A pharmaceutical preparation of an isolated antibody typically has less than 250 ppm (e.g., less than 200 ppm, 150 ppm. 100 ppm) of host cell proteins (HCP) as determined by an ELISA based HCP assay performed as recommended by an FDA "Guidance for Industry" document.

As used herein, the term "baseline" in reference to amount, concentration or level of a molecule refers to the amount, concentration, or level of the molecule prior to the administration of a therapeutic (e.g., antibody) provided for herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps. Any step or composition that uses the transitional phrase of "comprise" or "comprising" can also be said to describe the same with the transitional phase of "consisting of" or "consists."

As used herein, the term "monoclonal antibody" refers to an antibody obtained from a population of substantially homogeneous antibodies, i.e., individual antibodies in the population have the same primary sequence except for possible naturally occurring mutations that may be present in minor amounts. Monoclonal antibodies are highly specific and directed against a single antigenic site (i.e., an epitope on human FcRn). In contrast to polyclonal antibody preparations which typically include different antibodies directed against different epitopes, each monoclonal antibody is directed against a single epitope on the antigen. The modifier "monoclonal" indicates the character of the antibody as being obtained from a substantially homogenous population of antibodies, and is not to be construed as requiring production of the antibody by any particular method.

As used herein, the terms "variable region" and "variable domain" refer to the portions of the light and heavy chains of an antibody that include amino acid sequences of complementary determining regions (CDRs, e.g., CDR L1, CDR L2, CDR L3, CDR H1, CDR H2, and CDR H3) and framework regions (FRs). According to the methods used in this disclosure, the amino acid positions assigned to CDRs and FRs are defined according to Kabat. Using this numbering system, the actual linear amino acid sequence may contain fewer or additional amino acids corresponding to a shortening of, or insertion into, a CDR (defined further herein) or FR (defined further herein) of the variable region. For example, a heavy chain variable region may include a single inserted residue (i.e., residue 52a according to Kabat) after residue 52 of CDR H2 and inserted residues (i.e., residues 82a, 82b, 82c, etc. according to Kabat) after residue 82 of heavy chain FR. The Kabat numbering of residues may be determined for a given antibody by alignment at regions of homology of the sequence of the antibody with a "standard" Kabat numbered sequence.

As used herein, the terms "complementary determining regions" and "CDRs" refer to the regions of an antibody variable domain or variable region which are hypervariable in sequence and/or form structurally defined loops. A CDR is also known as a hypervariable region. The light chain and heavy chain variable regions each has three CDRs. The light chain variable region contains CDR L1, CDR L2, and CDR L3. The heavy chain variable region contains CDR H1, CDR H2, and CDR H3. Each CDR may include amino acid residues from a complementarity determining region as defined by Kabat (i.e. about residues 24-34 (CDR L1), 50-56 (CDR L2) and 89-97 (CDR L3) in the light chain variable region and about residues 31-35 (CDR H1), 50-65 (CDR H2) and 95-102 (CDR H3) in the heavy chain variable region.

As used herein, the term "FcRn" refers a neonatal Fc receptor that binds to the Fc region of an IgG antibody, e.g., an IgG1 antibody. An exemplary FcRn is human FcRn having UniProt ID No. P55899. Human FcRn is believed to be responsible for maintaining the half-life of IgG by binding and trafficking constitutively internalized IgG back to the cell surface for the recycling of IgG.

As used herein, the terms "affinity" and "binding affinity" refer to the strength of the binding interaction between two molecules. Generally, binding affinity refers to the strength of the sum total of non-covalent interactions between a single binding site of a molecule and its binding partner, such as an isolated antibody and its target (e.g., an isolated anti-FcRn antibody and a human FcRn). Unless indicated otherwise, binding affinity refers to intrinsic binding affinity, which reflects a 1:1 interaction between members of a binding pair. The binding affinity between two molecules is commonly described by the dissociation constant ($K_D$) or the affinity constant ($K_A$). Two molecules that have low binding affinity for each other generally bind slowly, tend to dissociate easily, and exhibit a large $K_D$. Two molecules that have high affinity for each other generally bind readily, tend to remain bound longer, and exhibit a small $K_D$.

As used herein, the term "inhibit IgG binding to FcRn" refers to the ability of an anti-FcRn antibody to block or inhibit the binding of IgG (e.g., IgG1) to human FcRn. In some embodiments, an anti-FcRn antibody binds FcRn, for example, at the site on human FcRn to which IgG binds. Thus, the anti-FcRn antibody is able to inhibit the binding of IgG (e.g., a subject's autoantibodies) to FcRn. In some embodiments, the molecule (e.g., an anti-FcRn antibody of the disclosure) substantially or completely inhibits binding to IgG. In some embodiments, the binding of IgG is reduced by at least 10%, 20%, 30%, 40%, 50%, 60%, 70%, 80%, 90%, 95%, or even 100%.

As used herein, the term "inhibit pathogenic antibody binding to FcRn" refers to the ability of an anti-FcRn antibody to block or inhibit the binding of a pathogenic antibody (e.g., pathogenic IgG antibody) to human FcRn. In some embodiments, an anti-FcRn antibody binds FcRn, for example, at the site on human FcRn to which the pathogenic antibody binds. Thus, the anti-FcRn antibody is able to inhibit the binding of pathogenic antibodies (e.g., pathogenic IgG antibodies) to FcRn. In some embodiments, the molecule (e.g., an anti-FcRn antibody) substantially or completely inhibits binding to pathogenic antibodies. In some embodiments, the binding of pathogenic antibodies to FcRn is reduced by at least 10%, 20%, 30%, 40%, 50%, 60%, 70%, 80%, 90%, 95%, or even 100%.

As used herein, the term "hydrophobic amino acid" refers to an amino acid having relatively low-water solubility. Hydrophobic amino acids include, but are not limited to, leucine, isoleucine, alanine, phenylalanine, valine, and proline. In some embodiments, hydrophobic amino acids in the present disclosure are alanine, leucine, isoleucine, and valine.

As used herein, the term "polar amino acid" refers to an amino acid having a chemical polarity in its side chain induced by atoms with different electronegativity. The polarity of a polar amino acid is dependent on the electronegativity between atoms in the side chain of the amino acid and the asymmetry of the structure of the side chain. Polar amino acids include, but are not limited to, serine, threonine, cysteine, methionine, tyrosine, tryptophan, asparagine, and glutamine. In some embodiments, polar amino acids in the present disclosure are serine, threonine, asparagine, glutamine, cysteine, and tyrosine.

As used herein, the term "acidic amino acid" refers to an amino acid whose side chain contains a carboxylic acid group having a pKa between 3.5 and 4.5. In some embodiments, acidic amino acids are aspartic acid and glutamic acid.

As used herein, the term "basic amino acid" refers to an amino acid whose side chain contains an amino group having a pKa between 9.5 and 13. In some embodiments, basic amino acids are histidine, lysine, and arginine.

As used herein, the term "percent (%) identity" refers to the percentage of amino acid (or nucleic acid) residues of a candidate sequence, e.g., an anti-FcRn antibody of the disclosure, that are identical to the amino acid (or nucleic acid) residues of a reference sequence, e.g., a wild-type anti-FcRn antibody, after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid (or nucleic acid) sequence identity of a given candidate sequence to, with, or against a given reference sequence (which can alternatively be phrased as a given candidate sequence that has or includes a certain percent amino acid (or nucleic acid) sequence identity to, with, or against a given reference sequence) is calculated as follows:

$$100\times(\text{fraction of A/B})$$

where A is the number of amino acid (or nucleic acid) residues scored as identical in the alignment of the candidate sequence and the reference sequence, and where B is the total number of amino acid (or nucleic acid) residues in the reference sequence. In some embodiments where the length of the candidate sequence does not equal to the length of the reference sequence, the percent amino acid (or nucleic acid) sequence identity of the candidate sequence to the reference sequence would not equal to the percent amino acid (or nucleic acid) sequence identity of the reference sequence to the candidate sequence.

In particular, embodiments, a reference sequence aligned for comparison with a candidate sequence may show that the candidate sequence exhibits from 50% to 100% identity across the full length of the candidate sequence or a selected portion of contiguous amino acid (or nucleic acid) residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same amino acid (or nucleic acid) residue as the corresponding position in the reference sequence, then the molecules are identical at that position. A position may be altered by a substitution, deletion, or insertion. A substitution, deletion, or insertion may comprise a certain number of amino acids, (e.g., 1, 2, 3, 4, 5, 6, 7, 8, 9, 10, 11, 12, 13, 14, 15, or more). When describing a substitution, deletion, or insertion of no more than n amino acids, this is meant that the substitution, deletion, or insertion comprises, e.g., 1, 2, 3, 4, 5, 6, 7, 8, 9, 10, 11, 12, 13, 14, 15, or n amino acids. The number or substitutions, deletions, or insertions can comprise a percent of the total sequence (e.g., 1%, 5%, 10%, 15%, 20%, or more) where the number of substitutions, deletions, or insertions alters 5%, 10%, 15%, 20% or more, of the amino acids in the total sequence.

As used herein, the term "fetal and neonatal alloimmune and/or autoimmune disorder" refers to an immune disorder in a fetus and/or neonate that is caused by the transplacental transfer of maternal antibodies (e.g., pathogenic maternal antibodies) directed against fetal and/or neonate antigens. For example, a pregnant subject's antibodies (e.g., pathogenic antibodies) may react against antigens in the fetus (e.g., antigens the fetus inherited from the fetus' father). Examples of fetal and neonatal alloimmune and/or autoimmune disorders are provided herein.

As used herein, the term "pathogenic antibody" refers to an antibody that causes one or more immune diseases or disorders in a subject (e.g., a pregnant subject), a fetus in a pregnant subject, and/or a neonate. In some embodiments, pathogenic antibodies are autoantibodies produced in a subject (e.g., a pregnant subject) against one or more of the subject's own proteins, thus causing autoimmune diseases or disorders in the subject. In some embodiments, pathogenic antibodies in a pregnant subject may transfer through the placenta to the fetus and react against antigens from the fetus (e.g., antigens that the fetus inherited from the fetus' father), thus causing, e.g., fetal and neonatal alloimmune and/or autoimmune disorders.

As used herein, the term "antibody-mediated enhancement of viral disease" refers to a viral disease in which antibodies can facilitate viral entry into host cells, thus leading to increased or enhanced infectivity in the cells. In some embodiments, an antibody may bind to a viral surface protein and the antibody/virus complex may bind to an FcRn receptor on a cell surface through interaction between the antibody and the receptor. Subsequently, the antibody/virus complex may be internalized into the cell.

As used herein, the term "gestational age" describes how far along the pregnancy is. The gestational age can be described in terms of weeks. Methods of determining gestational age are known in the art (e.g., Committee on Obstetric Practice American Institute of Ultrasound in Medicine Society for Maternal-Fetal Medicine, Committee Opinion. Number 700. May 2017; which is incorporated herein in its entirety). In some instances, the gestational age can be determined by ultrasound, weeks since first day of last menstrual period (LMP), or combinations thereof.

As used herein, the term "pharmaceutical composition" refers to a medicinal or pharmaceutical formulation that contains an active ingredient as well as one or more excipients and diluents to enable the active ingredient suitable for the method of administration. The pharmaceutical composition of the present disclosure includes pharmaceutically acceptable components that are compatible with the anti-FcRn antibody. The pharmaceutical composition may be in aqueous form for intravenous or subcutaneous administration or in tablet or capsule form for oral administration.

As used herein, the term "pharmaceutically acceptable carrier" refers to an excipient or diluent in a pharmaceutical composition. The pharmaceutically acceptable carrier must be compatible with the other ingredients of the formulation and not deleterious to the recipient. In the present disclosure, the pharmaceutically acceptable carrier must provide adequate pharmaceutical stability to the Fc construct. The nature of the carrier differs with the mode of administration. For example, for intravenous administration, an aqueous solution carrier is generally used; for oral administration, a solid carrier is generally used.

As used herein, the term "therapeutically effective amount" refers to an amount, e.g., pharmaceutical dose, effective in inducing a desired biological effect in a subject or patient or in treating a patient having a condition or disorder described herein. It is also to be understood herein that a "therapeutically effective amount" may be interpreted as an amount giving a desired therapeutic effect, either taken in one dose or in any dosage or route, taken alone or in combination with other therapeutic agents.

As used herein, the term "no more than" refers to an amount that is less than equal to. This may be an amount in integers. For example, no more than two substitutions can refer to 0, 1, or 2 substitutions.

As used herein, the terms "treatment" or "treating" refer to reducing, decreasing, decreasing the risk of, or decreasing the side effects of a particular disease or condition. Reducing, decreasing, decreasing the risk of, or decreasing the side effects of are relative to a subject who did not receive treatment, e.g., a control, a baseline, or a known control level or measurement.

Described herein is a method for administration of anti-FcRn antibodies, such as preferably nipocalimab. The methods can include the administration of a loading dose followed 1 week, 2 weeks, 3 weeks, or 4 weeks later by the initiation of weekly, biweekly, every 3 weeks, or monthly dosing at a maintenance dose lower than the loading dose (e.g., a dose that is about 75%, about 50%, about 25%, about 20%, about 15%, about 10%, or about 5% of the loading dose. The antibodies can be administered by IV or subcutaneously relatively rapidly, yet safely.

I. Anti-FcRn Antibodies

Described herein are methods for treating various disorders, comprising infusion of about 5 mg/kg to about 120 mg/kg dose of an anti-FcRn antibody to a subject. In some embodiments, the infusion is intravenous or subcutaneous.

In some embodiments, the method includes intravenous administration of an initial loading dose that is about 60 mg/kg followed by biweekly intravenous administration of a maintenance dose that is about 30 mg/kg. In some embodiments, the method includes intravenous administration of an initial loading dose that is about 60 mg/kg followed by biweekly intravenous administration of a maintenance dose of about 15 mg/kg. In some embodiments, the method includes intravenous administration of an initial loading dose that is about 30 mg/kg followed by biweekly intravenous administration of a maintenance dose that is about 30 mg/kg. In some embodiments, the method includes intravenous administration of an initial loading dose that is about 30 mg/kg followed by biweekly intravenous administration of a maintenance dose that is about 15 mg/kg. In some embodiments, the method includes intravenous administration of an initial loading dose that is about 60 mg/kg followed by monthly intravenous administration of a maintenance dose that is about 30 mg/kg. In some embodiments, the method includes intravenous administration of an initial loading dose that is about 60 mg/kg followed by monthly intravenous administration of a maintenance dose that is about 15 mg/kg. In some embodiments, the method includes intravenous administration of an initial loading dose that is about 30 mg/kg followed by monthly intravenous administration of a maintenance dose that is about 30 mg/kg. In some embodiments, the method includes intravenous administration of an initial loading dose that is about 30 mg/kg followed by monthly intravenous administration of a maintenance dose that is about 15 mg/kg.

In some embodiments, the method includes subcutaneous administration of an initial loading dose that is about 60 mg/kg followed by biweekly subcutaneous administration of a maintenance dose that is about 30 mg/kg. In some embodiments, the method includes subcutaneous administration of an initial loading dose that is about 60 mg/kg followed by biweekly subcutaneous administration of a maintenance dose of about 15 mg/kg. In some embodiments, the method includes subcutaneous administration of an initial loading dose that is about 30 mg/kg followed by biweekly subcutaneous administration of a maintenance dose that is about 30 mg/kg. In some embodiments, the method includes subcutaneous administration of an initial loading dose that is about 30 mg/kg followed by biweekly subcutaneous administration of a maintenance dose that is about 15 mg/kg. In some embodiments, the method includes subcutaneous administration of an initial loading dose that is about 60 mg/kg followed by monthly subcutaneous administration of a maintenance dose that is about 30 mg/kg. In some embodiments, the method includes subcutaneous administration of an initial loading dose that is about 60 mg/kg followed by monthly subcutaneous administration of a maintenance dose that is about 15 mg/kg. In some embodiments, the method includes subcutaneous administration of an initial loading dose that is about 30 mg/kg followed by monthly subcutaneous administration of a maintenance dose that is about 30 mg/kg. In some embodiments, the method includes subcutaneous administration of an initial loading dose that is about 30 mg/kg followed by monthly subcutaneous administration of a maintenance dose that is about 15 mg/kg.

In some embodiments, the method includes intravenous administration of an initial loading dose that is about 60 mg/kg followed by biweekly subcutaneous administration of a maintenance dose that is about 30 mg/kg. In some embodiments, the method includes intravenous administration of an initial loading dose that is about 60 mg/kg followed by biweekly subcutaneous administration of a maintenance dose of about 15 mg/kg. In some embodiments, the method includes intravenous administration of an initial loading dose that is about 30 mg/kg followed by biweekly subcutaneous administration of a maintenance dose that is about 30 mg/kg. In some embodiments, the method includes intravenous administration of an initial loading dose that is about 30 mg/kg followed by biweekly subcutaneous administration of a maintenance dose that is about 15 mg/kg. In some embodiments, the method includes intravenous administration of an initial loading dose that is about 60 mg/kg followed by monthly subcutaneous administration of a maintenance dose that is about 30 mg/kg. In some embodiments, the method includes intravenous administration of an initial loading dose that is about 60 mg/kg followed by monthly subcutaneous administration of a maintenance dose that is about 15 mg/kg. In some embodiments, the method includes intravenous administration of an initial loading dose that is about 30 mg/kg followed by monthly subcutaneous administration of a maintenance dose that is about 30 mg/kg. In some embodiments, the method includes intravenous administration of an initial loading dose that is about 30 mg/kg followed by monthly subcutaneous administration of a maintenance dose that is about 15 mg/kg.

In some embodiments, the anti-FcRn antibody is M281. In some embodiments, the anti-FcRn antibody is nipocalimab. In some embodiments, M281 and nipocalimab comprise the same amino acid sequence. In some embodiments, M281 and nipocalimab comprise the same heavy chain and light chain amino acid sequence. In some embodiments, M281 and nipocalimab comprise the same variable heavy chain and variable light chain amino acid sequence. As used herein, "M281" and "nipocalimab" refer to the same antibody and can be used interchangeably. In preferred embodiments, the anti-FcRn antibody is M281.

In some embodiments, the anti-FcRn antibody is M281 and comprises or consists of: a light chain comprising or consisting of the sequence: QSALTQPASVSGS- PGQSITISCTGTGSDVGSYNLVSWYQQHPGKAPKLMIYGD-SERPSGVSN RFSGSKSGNTASLTISGLQAEDEADYY-CSSYAGSGIYVFGTGTKVTVLGQPKAAPSVTLFPP SSEELQANKATLVCLISDFYPGAVTVAWKADSSPVK-AGVETTTPSKQSNNKYAASSYLSLT PEQWKSHKSYS-CQVTHEGSTVEKTVAPTECS (SEQ ID NO: 1); and a heavy chain comprises or consists of the sequence:

```
                                              (SEQ ID NO: 2)
EVQLLESGGGLVQPGGSLRLSCAASGFTFSTYAMGWVRQAPGKGLEWVS

SIGASGSQTRYADSVKGRFTISRDNSKNTLYLQMNSLRAEDTAVYYCAR

LAIGDSYWGQGTMVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQ

YASTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLS

LSPG.
```

In some embodiments, the anti-FcRn antibody has: (a) a light chain sequence that is at least 90%, 95%, 96%, 97% 98%, or 99% identical to SEQ ID NO: 1, wherein the LCDR1 comprises the sequence TGTGSDVGSYNLVS (SEQ ID NO: 3), the LCDR2 comprises the sequence GDSERPS (SEQ ID NO: 4), the LCDR3 comprises the sequence SSYAGSGIYV (SEQ ID NO: 5); and (b) a heavy chain sequence that is at least 90%, 95%, 96%, 97% 98%, or 99% identical to SEQ ID NO: 2, wherein the HCDR1 comprises the sequence TYAMG (SEQ ID NO: 6), the HCDR2 comprises the sequence SIGASGSQTRYADS (SEQ ID NO: 7), and the HCDR3 comprises the sequence

```
                                              (SEQ ID NO: 8)
LAIGDSY.
```

In some embodiments, the anti-FcRn antibody comprises a light chain variable region comprising an amino acid sequence that is at least 90%, 95%, 96%, 97%, 98%, 99%, or 100% identical to: QSALTQPASVSGS-PGQSITISCTGTGSDVGSYNLVSWYQQHPGKAPK-LMIYGDSERPSGVSN RFSGSKSGNTASLTISGLQAE-DEADYYCSSYAGSGIYVFGTGTKVTVL (SEQ ID NO: 9). In some embodiments, the light chain variable region contains a LCDR1 having the sequence of TGTGSDVGSYNLVS (SEQ ID NO: 3), a LCDR2 having the sequence of GDSERPS (SEQ ID NO: 4), a LCDR3 having the sequence of SSYAGSGIYV (SEQ ID NO: 5).

In some embodiments, the anti-FcRn antibody comprises a heavy chain variable region comprising an amino acid sequence that is at least 90%, 95%, 96%, 97%, 98%, 99%, or 100% identical to: EVQLLESGGGLVQPGGSLRLS- CAASGFTFSTYAMGWVRQAPGKGLEWVSSIGASG-SQTRY ADSVKGRFTISRDNSKNTLYLQMNSLRAED-TAVYYCARLAIGDSYWGQGTMVTVSS (SEQ ID NO: 10). In some embodiments, the heavy chain variable region contains a HCDR1 having the sequence of TYAMG (SEQ ID NO: 6), a HCDR2 having the sequence of SIGASGSQTRYADS (SEQ ID NO: 7), and a HCDR3 having the sequence of LAIGDSY (SEQ ID NO: 8).

In some embodiments, the an anti-FcRn antibody comprises a heavy chain and a light chain, wherein the heavy chain comprises a HCDR1 of SEQ ID NO: 6, a HCDR2 of SEQ ID NO: 7, and a HCDR3 of SEQ ID NO: 8; and wherein the light chain comprises a LCDR1 of SEQ ID NO: 3, a LCDR2 of SEQ ID NO: 4, and a LCDR3 of SEQ ID NO: 5.

In some embodiments, the variable region heavy chain comprises an amino acid sequence having at least 90% identity to the sequence of SEQ ID NO: 10 and the variable region light chain comprises an amino acid sequence having at least 90% identity to the sequence of SEQ ID NO: 9. In some embodiments, the variable region heavy chain comprises an amino acid sequence having at least 95% identity to the sequence of SEQ ID NO: 10 and the variable region light chain comprises an amino acid sequence having at least 95% identity to the sequence of SEQ ID NO: 9. In some embodiments, the variable region heavy chain comprises an amino acid sequence having at least 99% identity to the sequence of SEQ ID NO: 10 and the variable region light chain comprises an amino acid sequence having at least 99% identity to the sequence of SEQ ID NO: 9.

In some embodiments, the heavy chain comprises an amino acid sequence having at least 90% identity to the sequence of SEQ ID NO: 2 and the light chain comprises an amino acid sequence having at least 90% identity to the sequence of SEQ ID NO: 1. In some embodiments, the heavy chain comprises an amino acid sequence having at least 95% identity to the sequence of SEQ ID NO: 2 and the light chain comprises an amino acid sequence having at least 95% identity to the sequence of SEQ ID NO: 1. In some embodiments, the heavy chain comprises an amino acid sequence having at least 99% identity to the sequence of SEQ ID NO: 2 and the light chain comprises an amino acid sequence having at least 99% identity to the sequence of SEQ ID NO: 1.

In some embodiments, the variable region heavy chain comprises the amino acid sequence of SEQ ID NO: 10 and the variable region light chain comprises the amino acid sequence of SEQ ID NO: 9.

In some embodiments, the heavy chain comprises the amino acid sequence of SEQ ID NO: 2 and the light chain comprises the amino acid sequence of SEQ ID NO: 1.

The antibodies described herein may further contain amino acid substitutions, additions, and/or deletions outside of the CDRs (i.e., in framework regions (FRs)). An amino acid substitution, addition, and/or deletion can be a substitution, addition, and/or deletion of one or more amino acids (e.g., 1, 2, 3, 4, 5, 6, 7, 8, or more). An amino acid substitution, addition, and/or deletion can be a substitution, addition, and/or deletion of eight or fewer, seven or fewer, six or fewer, five or fewer, four or fewer, three or fewer, or two or fewer single amino acids.

In some embodiments, the antibodies described herein may include amino acid substitutions, additions, and/or deletions in the constant regions (e.g., Fc region) of the antibody that, e.g., lead to decreased effector function, e.g., decreased complement-dependent cytolysis (CDC), antibody-dependent cell-mediated cytolysis (ADCC), and/or antibody-dependent cell-mediated phagocytosis (ADCP), and/or decreased B-cell killing. The constant regions are not involved directly in binding an antibody to its target, but exhibit various effector functions, such as participation of the antibody in antibody-dependent cellular toxicity. In some embodiments, the antibodies described herein are characterized by decreased binding (i.e., absence of binding) to human complement factor C1q and/or human Fc receptor on natural killer (NK) cells. In other embodiments, the antibodies are characterized by decreased binding (i.e., absence of binding) to human FcγRI, FcγRIIA, and/or FcγRIIIA. To alter or reduce an antibody-dependent effector function, such as CDC, ADCC, ADCP, and/or B-cell killing, antibodies described herein may be of the IgG class and contain one or more amino acid substitutions E233, L234, G236, D265, D270, N297, E318, K320, K322, A327, A330, P331, and/or P329 (numbering according to the EU System). In some embodiments, the antibodies described herein contain the mutations L234A/L235A or D265A/N297A (numbering according to the EU System). In some embodiments, the antibodies described herein contain asparagine (N) at position 297 (numbering according to the EU System). In some embodiments, an anti-FcRn antibody described herein is aglycosylated at position 297 (numbering according to the EU System). In some cases, an anti-FcRn antibody described herein does not have an N at position 297 (EU numbering) in any one of SEQ ID NOs: 2 and 23-26, such that the antibody is aglycosylated at that position. The resulting effectorless antibody shows very little binding to complement or Fc receptors (i.e., complement C1q binding), indicating low CDC potential.

In some embodiments, the isolated anti-FcRn antibody described herein contains a LCDR1 having the sequence of TGTGSDVGSYNLVS (SEQ ID NO: 3), a LCDR2 having the sequence of GDSERPS (SEQ ID NO: 4), a LCDR3 having the sequence of SSYAGSGIYV (SEQ ID NO: 5), a HCDR1 having the sequence of NYAMG (SEQ ID NO: 12), a HCDR2 having the sequence of SIGASGAQTRYADS (SEQ ID NO: 14), and a HCDR3 having the sequence of LAIGDSY (SEQ ID NO: 8).

In some embodiments, the isolated anti-FcRn antibody described herein contains a LCDR1 having the sequence of TGTGSDVGSYNLVS (SEQ ID NO: 3), a LCDR2 having the sequence of GDSERPS (SEQ ID NO: 4), a LCDR3 having the sequence of SSYAGSGIYV (SEQ ID NO: 5), a HCDR1 having the sequence of TYAMG (SEQ ID NO: 6), a HCDR2 having the sequence of SIGASGGQTRYADS (SEQ ID NO: 15), and a HCDR3 having the sequence of LAIGDSY (SEQ ID NO: 8).

In some embodiments, the light chain of the isolated anti-FcRn antibody comprises a sequence having at least 90% identity to the sequence of

```
                                        (SEQ ID NO: 1)
QSALTQPASVSGSPGQSITISCTGTGSDVGSYNLVSWYQQHPGKAPKLM

IYGDSERPSGVSNRFSGSKSGNTASLTISGLQAEDEADYYCSSYAGSGI

YVFGTGTKVTVLGQPKAAPSVTLFPPSSEELQANKATLVCLISDFYPGA

VTVAWKADSSPVKAGVETTTPSKQSNNKYAASSYLSLTPEQWKSHKSYS

CQVTHEGSTVEKTVAPTECS.
```

In some embodiments, the heavy chain of the isolated anti-FcRn antibody comprises a sequence having at least 90% identity to the sequence of (SEQ ID NO: 23)

EVQLLESGGGLVQPGGSLRLSCAASGFTFSTYAMGWVRQAPGKGLEWVS
SIGSSGAQTRYADSVKGRFTISRDNSKNTLYLQMNSLRAEDTAVYYCAR
LAIGDSYWGQGTMVTVSSASTKGPSVFPLAPSSKSTSGGTAALGCLVKD
YFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLS
LSPG.

In other embodiments, the heavy chain of the isolated anti-FcRn antibody comprises a sequence having at least 90% identity to the sequence of (SEQ ID NO: 24)

EVQLLESGGGLVQPGGSLRLSCAASGFTFSDYAMGWVRQAPGKGLEWVS
SIGASGSQTRYADSVKGRFTISRDNSKNTLYLQMNSLRAEDTAVYYCAR
LAIGDSYWGQGTMVTVSSASTKGPSVFPLAPSSKSTSGGTAALGCLVKD
YFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLS
LSPG.

In other embodiments, the heavy chain of the isolated anti-FcRn antibody comprises a sequence having at least 90% identity to the sequence of (SEQ ID NO: 25)

EVQLLESGGGLVQPGGSLRLSCAASGFTFSNYAMGWVRQAPGKGLEWVS
SIGASGAQTRYADSVKGRFTISRDNSKNTLYLQMNSLRAEDTAVYYCAR
LAIGDSYWGQGTMVTVSSASTKGPSVFPLAPSSKSTSGGTAALGCLVKD
YFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLS
LSPG.

In some embodiments, the heavy chain of the isolated anti-FcRn antibody comprises a sequence having at least 90% identity to the sequence of (SEQ ID NO: 26)

EVQLLESGGGLVQPGGSLRLSCAASGFTFSTYAMGWVRQAPGKGLEWVS
SIGASGGQTRYADSVKGRFTISRDNSKNTLYLQMNSLRAEDTAVYYCAR
LAIGDSYWGQGTMVTVSSASTKGPSVFPLAPSSKSTSGGTAALGCLVKD
YFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLS
LSPG.

In some embodiments, the isolated anti-FcRn antibody has a light chain and a heavy chain, wherein the light chain comprises a sequence having at least 90%, 95%, 96%, 97%, 98%, or 99% identity to the sequence of QSALTQPAS VSGSPGQSITISCTGTGSDVGSYNLVSWYQQH PGKAPKLMIYGDSERPSGVSN RFSGSKSGNTASLTI SGLQAEDEADYYCSSYAGSGIYVFGTGTKVTVLGQP-KAAPSVTLFPP SSEELQANKATLVCLISDFYPGAV TV AWKADSSPVKAGVETTTPSKQSNNKYAASSYLSLT PEQWKSHKSYSCQVTHEGSTVEKTVAPTECS (SEQ ID NO: 1); and the heavy chain comprises a sequence having at least 90%, 95%, 96%, 97%, 98%, or 99% identity to the sequence of (SEQ ID NO: 23)

EVQLLESGGGLVQPGGSLRLSCAASGFTFSTYAMGWVRQAPGKGLEWVS
SIGSSGAQTRYADSVKGRFTISRDNSKNTLYLQMNSLRAEDTAVYYCAR
LAIGDSYWGQGTMVTVSSASTKGPSVFPLAPSSKSTSGGTAALGCLVKD
YFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLS
LSPG.

In some embodiments, the isolated anti-FcRn antibody containing has light chain and a heavy chain, wherein the light chain comprises a sequence having at least 90%, 95%, 96%, 97%, 98%, or 99% identity to the sequence of QSALTQPASVSGSPGQSITISCTGTGSDVGSYN-LVSWYQQHPGKAPKLMIYGDSERPSGVSN RFSGSKS GNTASLTISGLQAEDEADYYCSSYAGSGIYVFGT GTKVTVLGQPKAAPSVTLFPP SSEELQANK ATLVC LISDFYPGAVTVAWKADSSPVKAGVETTTPSKQS NNKYAASSYLSLT PEQWKSHKSYSCQVTHEGSTVEK TVAPTECS (SEQ ID NO: 1); and the heavy chain comprises a sequence having at least 90%, 95%, 96%, 97%, 98%, or 99% identity to the sequence of (SEQ ID NO: 24)

```
EVQLLESGGGLVQPGGSLRLSCAASGFTFSDYAMGWVRQAPGKGLEWVS
SIGASGSQTRYADSVKGRFTISRDNSKNTLYLQMNSLRAEDTAVYYCAR
LAIGDSYWGQGTMVTVSSASTKGPSVFPLAPSSKSTSGGTAALGCLVKD
YFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLS
LSPG.
```

In some embodiments, the isolated anti-FcRn antibody has a light chain and a heavy chain, wherein the light chain comprises a sequence having at least 90%, 95%, 96%, 97%, 98%, or 99% identity to the sequence of QSALTQ PASVSGSPGQSITISCTGTGSDVGSYNLVSWYQQHP GKAPKLMIYGDSERPSGVSN RFSGSKSGNTASLTI SGLQAEDEADYYCSSYAGSGIYVFGTGTKVTVLGQP-KAAPSVTLFPP SSEELQANKATLVCLISDFYPGAV TVAWKADSSPVKAGVETTTPSKQSNNKYAAS-SYLSLT PEQWKSHKSYSCQVTHEGSTVEKTV APTECS (SEQ ID NO: 1); and the heavy chain comprises a sequence having at least 90%, 95%, 96%, 97%, 98%, or 99% identity to the sequence of (SEQ ID NO: 25)

```
EVQLLESGGGLVQPGGSLRLSCAASGFTFSNYAMGWVRQAPGKGLEWVS
SIGASGAQTRYADSVKGRFTISRDNSKNTLYLQMNSLRAEDTAVYYCAR
LAIGDSYWGQGTMVTVSSASTKGPSVFPLAPSSKSTSGGTAALGCLVKD
YFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLS
LSPG.
```

In some embodiments, the isolated anti-FcRn antibody has a light chain and a heavy chain, wherein the light chain comprises a sequence having at least 90%, 95%, 96%, 97%, 98%, or 99% identity to the sequence of QSALT QPASVSGSPGQSITISCTGTGSDVGSYNLVSWYQ QHPGKAPKLMIYGDSERPSGVSN RFSGSKSGNTAS LTISGLQAEDEADYYCSSYAGSGIYVFGTG TKVTV LGQPKAAPSVTLFPP SSEELQANKATLVCLISDFYP-GAVTVAWKADSSPVKAGVETTTPSKQSNNKYAAS-SYLSLT PEQWKSHKSYSCQVTHEGSTVEKTVA PTECS (SEQ ID NO: 1); and the heavy chain comprises a sequence having at least 90%, 95%, 96%, 97%, 98%, or 99% identity to the sequence of (SEQ ID NO: 26)

```
EVQLLESGGGLVQPGGSLRLSCAASGFTFSTYAMGWVRQAPGKGLEWVS
SIGASGGQTRYADSVKGRFTISRDNSKNTLYLQMNSLRAEDTAVYYCAR
LAIGDSYWGQGTMVTVSSASTKGPSVFPLAPSSKSTSGGTAALGCLVKD
YFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLS
LSPG.
```

In some embodiments, the heavy chain of the isolated anti-FcRn antibody comprises a sequence having at least 90%, 95%, 96%, 97%, 98%, 99%, or 100% identity to the sequence of any one of SEQ ID NOs: 23-26. In other embodiments, the light chain of the isolated anti-FcRn antibody comprises a sequence having at least 90%, 95%, 96%, 97%, 98%, 99%, or 100% identity to the sequence of SEQ ID NO: 1.

In some embodiments, the heavy chain of the isolated anti-FcRn antibody comprises a sequence having no more than 5, 4, 3, 2 or 1 single amino acid substitutions relative to the amino acid sequence of SEQ ID NO: 2. In some embodiments, the light chain of the isolated anti-FcRn antibody comprises a sequence having no more than 5, 4, 3, 2 or 1 single amino acid substitutions relative to the sequence of SEQ ID NO: 1.

In some embodiments, the isolated anti-FcRn antibody includes amino acid substitution N297A, relative to the sequence of any one of SEQ ID NOs: 2 (numbering according to the EU System). In some embodiments, the isolated anti-FcRn antibody includes asparagine (N) at position 297, relative to the sequence of any one of SEQ ID NOs: 2 (numbering according to the EU System).

In some embodiments, the isolated anti-FcRn antibody further includes amino acid substitutions D355E and L357M, relative to the sequence of any one of SEQ ID NOs: 2. (According to EU Numbering).

In some embodiment, the isolated anti-FcRn antibody does not contain a C-terminal lysine at residue 446, relative to the sequence of SEQ ID NO: 2.

In some embodiments, the isolated anti-FcRn antibody has a light chain and a heavy chain, wherein the light chain comprises or consists of the sequence of QSAL TQ-PASVSGSPGQSITISCTGTGSDVGSYNLVSWYQ QHPGKAPKLMIYGDSERPSGVSN RFSGSKSGNTAS LTISGLQAEDEADYYCSSYAGSGIYVFGTG TKVTV LGQPKAAPSVTLFPP SSEELQANKATLVCLISDFYP-GAVTVAWKADSSPVKAGVETTTPSKQSNNKYAAS-SYLSLT PEQWKSHKSYSCQVTHEGSTVEKTVA PTECS (SEQ ID NO: 1); and the heavy chain comprises or consists of the sequence of (SEQ ID NO: 23)

```
EVQLLESGGGLVQPGGSLRLSCAASGFTFSTYAMGWVRQAPGKGLEWVS
SIGSSGAQTRYADSVKGRFTISRDNSKNTLYLQMNSLRAEDTAVYYCAR
LAIGDSYWGQGTMVTVSSASTKGPSVFPLAPSSKSTSGGTAALGCLVKD
```

-continued

```
YFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQ

YASTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLS

LSPG.
```

In some embodiments, the isolated anti-FcRn antibody has a light chain and a heavy chain, wherein the light chain comprises the sequence of QSALTQPASVS GSPG QSITISCTGTGSDVGSYNLVSWYQQHPGKAPK LMI YGDSERPSGVSN RFSGSKSGNTASLTISGLQAEDEA DYYCSSYAGSGIYVFGTGTKVTVLGQPKAAPSVT LFPP SSEELQANKATLVCLISDFYPGAVTVAWKADS SPVKAGVETTTPSKQSNNKYAASSYLSLT PEQWK-SHKSYSCQVTHEGSTVEKTVAPTECS (SEQ ID NO: 1); and the heavy chain comprises or consists of the sequence of

```
                                          (SEQ ID NO: 24)
EVQLLESGGGLVQPGGSLRLSCAASGFTFSDYAMGWVRQAPGKGLEWVS

SIGASGSQTRYADSVKGRFTISRDNSKNTLYLQMNSLRAEDTAVYYCAR

LAIGDSYWGQGTMVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQ

YASTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLS

LSPG.
```

In some embodiments, the isolated anti-FcRn antibody has a light chain and a heavy chain, wherein the light chain comprises the sequence of QSALTQPASVSG SPGQ SITISCTGTGSDVGSYNLVSWYQQHPGKAPKLMIYG DSERPSGVSN RFSGSKSGNTASLTISGLQAEDEAD-YYCSSYAGSGIYVFGTGTKVTVLGQPKAAPSVTLFPP SSEELQANKATLVCLISDFYPGAVTVAWKADSSPVK-AGVETTTPSKQSNNKYAASSYLSLT PEQWKSHKSYS-CQVTHEGSTVEKTVAPTECS (SEQ ID NO: 1); and the heavy chain comprises or consists of the sequence of

```
                                          (SEQ ID NO: 25)
EVQLLESGGGLVQPGGSLRLSCAASGFTFSNYAMGWVRQAPGKGLEWVS

SIGASGAQTRYADSVKGRFTISRDNSKNTLYLQMNSLRAEDTAVYYCAR

LAIGDSYWGQGTMVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQ

YASTYRVVSVLTVLHQDWLNGKEYKCKVSNKALPAPIEKTISKAKGQPR
```

-continued

```
EPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLS

LSPG.
```

In some embodiments, the isolated anti-FcRn antibody has a light chain and a heavy chain, wherein the light chain comprises or consists of the sequence of QSALTQP ASVSGSPGQSITISCTGTGSDVGSYNLVSWYQQH PGKAPKLMIYGDSERPSGVSN RFSGSKSGNTASL TIS GLQAEDEADYYCSSYAGSGIYVFGTGTKVTVLGQP-KAAPSVTLFPP SSEELQANKATLVCLISDFYPGA VT VAWKADSSPVKAGVETTTPSKQSNNKYAASSYLSLT PEQWKSHKSYSCQVTHEGSTVEKTVAPTECS (SEQ ID NO: 1); and the heavy chain comprises or consists of the sequence of

```
                                          (SEQ ID NO: 26)
EVQLLESGGGLVQPGGSLRLSCAASGFTFSTYAMGWVRQAPGKGLEWVS

SIGASGGQTRYADSVKGRFTISRDNSKNTLYLQMNSLRAEDTAVYYCAR

LAIGDSYWGQGTMVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQ

YASTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLS

LSPG.
```

Without being bound by any particular theory, it is believed that the anti-FcRn antibodies compete with and inhibit the binding of IgG to human FcRn. Epitope mapping by hydrogen-deuterium exchange of the antibodies indicates that the antibodies bind to an epitope on FcRn located in and/or adjacent to the Fc-FcRn interaction interface, which suggests that the antibodies block IgG binding to FcRn by direct inhibition. Furthermore, the epitope-mapped binding site is distant from the albumin-binding site of FcRn. Accordingly, serum albumin-binding should not be inhibited and serum albumin levels should not be reduced more than about 35%, 30% or 25% below.

In some embodiments, the anti-FcRn antibody is nipocalimab, RVT-1401 (HL161), rozanolixizumab (UCB7665), ALXN1830, ABY-039, or efgartigimod. RVT-1401 (also referred to as HL161BKN) is described in WO2020097099, rozanolixizumab is described in WO2014019727, and efgartigimod (ARGX-113) is described in WO2015100299, each of which is hereby incorporated by reference in its entirety. In some embodiments, the anti-FcRN antibody is a biosimilar of any of anti-FcRN antibodies provided for herein. In preferred embodiments, the anti-FcRn antibody is nipocalimab.

In some embodiments, the Fc domain of the antibody is not fucosylated. In some embodiments of all the methods described herein, the Fc domain of the antibody is not glycosylated. In some embodiments of all the methods described herein, the antibody lacks effector function. In some embodiments of all the methods described herein, the antibody is an IgG1 antibody.

II. FcRn Inhibition

FcRn is a type I transmembrane protein that functions as an IgG- and serum albumin-binding, intracellular vesicular trafficking protein. FcRn is expressed in endothelial cells, luminal epithelial cells, hepatocytes, podocytes, granulocytes, monocytes, macrophages, dendritic cells, and NK cells, but not on B or T cells. FcRn maintains the half-life of IgG by binding and trafficking constitutively internalized IgG back to the cell surface. Binding of both Fc and serum albumin by FcRn occurs in the early endosome at pH 6.0, followed by sorting of the FcRn into vesicles, which traffic the FcRn-bound IgG or albumin back to the cell surface where FcRn rapidly releases the IgG or albumin at pH 7.4. This trafficking cycle maintains the half-life of IgG and albumin by recycling both into the circulation and preventing trafficking to the lysosomes for degradation. FcRn also captures internalized IgG Fc in epithelial cells and transports them bidirectionally to the opposing apical or basolateral membranes. This function allows IgG to traffic to the lumen of organs such as the gastrointestinal tract or the transport of IgG or IgG-antigen complexes from the lumen to the vasculature or lymphoid tissues in the stromal layers.

In order to study the contribution of FcRn to IgG homeostasis, mice have been engineered so that parts of the light and heavy chains of FcRn have been "knocked out" so that these proteins are not expressed (Junghans et al., *Proc Natl Acad Sci USA* 93:5512, 1996). In these mice, the serum half-life and concentrations of IgG were dramatically reduced, suggesting an FcRn-dependent mechanism of IgG homeostasis. Studies in rodent models, such as the one discussed above, suggest that blockage of FcRn can increase IgG catabolism, including that of pathogenic autoantibodies, thereby inhibiting disease (e.g., an autoimmune disease) development. FcRn may also contribute to antigen presentation through trafficking of immune complexes to antigen degradation and MHC loading compartments.

The present disclosure provides isolated anti-FcRn antibodies that bind to human FcRn with high affinity. The anti-FcRn antibodies compete with and effectively inhibit the binding of other anti-FcRn antibodies (e.g., IgG, IgG autoantibodies) to FcRn, thereby increasing the catabolism and decreasing the half-life of other anti-FcRn antibodies (e.g., IgG, IgG autoantibodies). The anti-FcRn antibodies may be used in a method of treating or reducing immune complex-based activation of an immune response in a subject, such as an immune response caused by autoantibodies in an autoimmune disease.

Placental transfer of maternal IgG antibodies to the fetus is an important FcRn-dependent mechanism that provides protection to the neonate while his/her humoral response is inefficient. During fetal life, FcRn in the syncytiotrophoblast layers of the placenta is responsible for the transfer of maternal IgG antibodies to the fetus. Pathogenic maternal antibodies (e.g., pathogenic maternal IgG antibodies) may also cross the placenta by binding to FcRn and cause alloimmune disorders and/or autoimmune disorders in the fetus and neonate. In some embodiments, pathogenic antibodies in the pregnant subject cause a fetal and neonatal alloimmune and/or autoimmune disorder in a fetus in the pregnant subject. The anti-FcRn antibodies described herein may compete with and inhibit the binding of maternal pathogenic antibodies (e.g., maternal pathogenic IgG antibodies) to FcRn, thereby increasing the catabolism and decreasing the half-life of these pathogenic antibodies.

The present disclosure provides isolated anti-FcRn antibodies that bind to human FcRn. The anti-FcRn antibodies may compete with and inhibit the binding of other anti-FcRn antibodies (e.g., IgG, IgG autoantibodies) to FcRn, thereby increasing the catabolism and decreasing the half-life of other anti-FcRn antibodies (e.g., IgG, IgG autoantibodies). The anti-FcRn antibodies may be used in a method of treating or reducing immune complex-based activation of an immune response in a subject, such as an immune response caused by autoantibodies in an autoimmune disease. Reducing an immune response may be described as reducing an immune response relative to a subject who does not receive treatment (e.g., a control subject). The anti-FcRn antibodies may also be used in methods of decreasing pathogenic antibody transport (e.g., pathogenic maternal IgG antibody transport) across the placenta of a pregnant subject, increasing pathogenic antibody catabolism in a pregnant subject, and treating an antibody-mediated enhancement of viral disease in a fetus or a neonate by administering to a pregnant subject an isolated antibody that binds to human FcRn. Decreasing pathogenic antibody transport across the placenta of a pregnant subject, may be described as decreasing pathogenic antibody transport relative to a subject who does not receive treatment (e.g., a control subject). In another aspect, the disclosure features a method of treating an antibody-mediated enhancement of viral disease in a fetus or a neonate, the method comprising, consisting of, or consisting essentially of administering an antibody described herein to a pregnant subject, wherein the antibody comprises, consists of, or consists essentially of: a light chain and a heavy chain, wherein the light chain comprises, consists of, or consists essentially of the sequence of SEQ ID NO: 1; and the heavy chain comprises, consists of, or consists essentially of the sequence of SEQ ID NO: 2. In another aspect, the disclosure features a method of treating an antibody-mediated enhancement of viral disease in a fetus or a neonate, the method comprising, consisting of, or consisting essentially of administering an antibody to a pregnant subject, wherein the antibody comprises, consists of, or consists essentially of: a light chain and a heavy chain, wherein the light chain comprises, consists of, or consists essentially of a sequence having at least 90%, 95%, 96%, 97%, 98%, 99% or 100% identity to the sequence of SEQ ID NO: 1; and the heavy chain comprises, consists of, or consists essentially of a sequence having at least 90%, 95%, 96%, 97%, 98%, 99% or 100% identity to the sequence of SEQ ID NO: 2.

III. Vectors, Host Cells, and Antibody Production

The anti-FcRn antibodies can be produced from a host cell. A host cell refers to a vehicle that includes the necessary cellular components, e.g., organelles, needed to express the polypeptides and constructs described herein from their corresponding nucleic acids. The nucleic acids may be included in nucleic acid vectors that can be introduced into the host cell by conventional techniques known in the art (e.g., transformation, transfection, electroporation, calcium phosphate precipitation, direct microinjection, infection, etc.). The choice of nucleic acid vectors depends in part on the host cells to be used. Generally, host cells are of either prokaryotic (e.g., bacterial) or eukaryotic (e.g., mammalian) origin.

Nucleic Acid Vector Construction and Host Cells

A nucleic acid sequence encoding the amino acid sequence of an anti-FcRn antibody may be prepared by a variety of methods known in the art. These methods include, but are not limited to, oligonucleotide-mediated (or site-directed) mutagenesis and PCR mutagenesis. A nucleic acid molecule encoding an anti-FcRn antibody may be obtained using standard techniques, e.g., gene synthesis. Alternatively, a nucleic acid molecule encoding a wild-type anti-FcRn antibody may be mutated to contain specific amino acid substitutions using standard techniques in the art, e.g., QuikChange™ mutagenesis. Nucleic acid molecules can be synthesized using a nucleotide synthesizer or PCR techniques.

Nucleic acid sequences encoding anti-FcRn antibodies may be inserted into a vector capable of replicating and expressing the nucleic acid molecules in prokaryotic or eukaryotic host cells. Many vectors are available in the art and can be used for the purpose of the disclosure. Each vector may contain various components that may be adjusted and optimized for compatibility with the particular host cell. For example, the vector components may include, but are not limited to, an origin of replication, a selection marker gene, a promoter, a ribosome binding site, a signal sequence, the nucleic acid sequence encoding protein of interest, and a transcription termination sequence.

In some embodiments, mammalian cells are used as host cells for the disclosure. Examples of mammalian cell types include, but are not limited to, human embryonic kidney (HEK) (e.g., HEK293, HEK 293F), Chinese hamster ovary (CHO), HeLa, COS, PC3, Vero, MC3T3, NS0, Sp2/0, VERY, BHK, MDCK, W138, BT483, Hs578T, HTB2, BT20, T47D, NS0 (a murine myeloma cell line that does not endogenously produce any immunoglobulin chains), CRL7030, and HsS78Bst cells. In other embodiments, *E. coli* cells are used as host cells for the disclosure. Examples of *E. coli* strains include, but are not limited to, *E. coli* 294 (ATCC® 31,446), *E. coli* λ 1776 (ATCC® 31,537, *E. coli* BL21 (DE3) (ATCC® BAA-1025), and *E. coli* RV308 (ATCC® 31,608). Different host cells have characteristic and specific mechanisms for the posttranslational processing and modification of protein products. Appropriate cell lines or host systems may be chosen to ensure the correct modification and processing of the anti-FcRn antibody expressed. The above-described expression vectors may be introduced into appropriate host cells using conventional techniques in the art, e.g., transformation, transfection, electroporation, calcium phosphate precipitation, and direct microinjection. Once the vectors are introduced into host cells for protein production, host cells are cultured in conventional nutrient media modified as appropriate for inducing promoters, selecting transformants, or amplifying the genes encoding the desired sequences. Methods for expression of therapeutic proteins are known in the art, see, for example, Paulina Balbas, Argelia Lorence (eds.) *Recombinant Gene Expression: Reviews and Protocols* (*Methods in Molecular Biology*), Humana Press; 2nd ed. 2004 (Jul. 20, 2004) and Vladimir Voynov and Justin A. Caravella (eds.) *Therapeutic Proteins: Methods and Protocols* (*Methods in Molecular Biology*) Humana Press; 2nd ed. 2012 (Jun. 28, 2012).

Protein Production, Recovery, and Purification

Host cells used to produce the anti-FcRn antibodies may be grown in media known in the art and suitable for culturing of the selected host cells. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI-1640. Examples of suitable media for bacterial host cells include Luria broth (LB) plus necessary supplements, such as a selection agent, e.g., ampicillin. Host cells are cultured at suitable temperatures, such as from about 20° C. to about 39° C., e.g., from 25° C. to about 37° C., about 37° C., and $CO_2$ levels, such as 5 to 10% (about 8%). The pH of the medium is generally from about 6.8 to 7.4, e.g., 7.0, depending mainly on the host organism. If an inducible promoter is used in the expression vector of the disclosure, protein expression is induced under conditions suitable for the activation of the promoter.

Protein recovery typically involves disrupting the host cell, generally by such means as osmotic shock, sonication, or lysis. Once the cells are disrupted, cell debris may be removed by centrifugation or filtration. The proteins may be further purified. An anti-FcRn antibody may be purified by any method known in the art of protein purification, for example, by protein A affinity, other chromatography (e.g., ion exchange, affinity, and size-exclusion column chromatography), centrifugation, differential solubility, or by any other standard technique for the purification of proteins. In some instances, an anti-FcRn antibody can be conjugated to marker sequences, such as a peptide to facilitate purification. An example of a marker amino acid sequence is a hexa-histidine peptide (His-tag), which binds to nickel-functionalized agarose affinity column with micromolar affinity. Other peptide tags useful for purification include, but are not limited to, the hemagglutinin "HA" tag, which corresponds to an epitope derived from the influenza hemagglutinin protein.

Alternatively, anti-FcRn antibodies can be produced by the cells of a subject (e.g., a human), e.g., in the context of therapy, by administrating a vector (e.g., a retroviral vector, adenoviral vector, poxviral vector (e.g., vaccinia viral vector, such as Modified Vaccinia Ankara (MVA)), adeno-associated viral vector, and alphaviral vector) containing a nucleic acid molecule encoding the anti-FcRn antibody of the disclosure. The vector, once inside a cell of the subject (e.g., by transformation, transfection, electroporation, calcium phosphate precipitation, direct microinjection, infection, etc.) will promote expression of the anti-FcRn antibody, which is then secreted from the cell. If treatment of a disease or disorder is the desired outcome, no further action may be required. If collection of the protein is desired, blood may be collected from the subject and the protein purified from the blood by methods known in the art.

IV. Pharmaceutical Compositions and Preparations

The composition for infusion is an aqueous composition that is physiologically compatible (e.g., buffered to a physiological pH and substantially isotonic. The composition can include, for example: sodium chloride, Trehalose, and surfactant polysorbate (PS) 80, and buffered agents. The composition can include both an ionic osmolyte stabilizer (sodium chloride) and non-ionic osmolyte stabilizer (trehalose).

In certain embodiments, a suitable formulation may include about 25 mM sodium phosphate, about 25 mM sodium chloride, about 90.5 mg/ml Trehalose, about 0.01% polysorbate (PS) 80, and the antibody described herein at about 10 mg/ml, about 15 mg/ml, or about 30 mg/ml buffered at pH 6.5. In certain embodiments, a suitable formulation may include about 25 mM sodium succinate, about 25 mM sodium chloride, about 90.5 mg/ml Trehalose, about 0.01% polysorbate (PS) 80, and the antibody described herein at about 10 mg/ml, about 15 mg/ml, or about 30 mg/ml buffered at pH 6.6 or pH 6.5. In certain embodiments, a suitable formulation may include about 25 mM sodium succinate, about 25 mM sodium chloride, about 90.5 mg/ml Trehalose, about 0.01% polysorbate (PS) 80, and the antibody described herein at about 10 mg/ml, about 15 mg/ml, or about 30 mg/ml buffered at pH 5 to pH 8. In certain embodiments, a suitable formulation may include about 25 mM sodium succinate, about 25 mM sodium chloride, about 90.5 mg/ml Trehalose, about 0.01% polysorbate (PS) 80, and the antibody described herein at about 10 mg/ml, about 15 mg/ml, or about 30 mg/ml buffered at pH 5 to pH 7. In certain embodiments, a suitable formulation may include about 25 mM sodium succinate, about 25 mM sodium chloride, about 90.5 mg/ml Trehalose, about 0.01% polysorbate (PS) 80, and the antibody described herein at about 10 mg/ml, about 15 mg/ml, or about 30 mg/ml buffered at pH 6 to pH 7.

The disclosure features pharmaceutical compositions that include one or more anti-FcRn antibodies described herein. In addition to a therapeutically effective amount of the antibody, the pharmaceutical compositions may contain one or more pharmaceutically acceptable carriers or excipients, which can be formulated by methods known to those skilled in the art.

Acceptable carriers and excipients in the pharmaceutical compositions are nontoxic to recipients at the dosages and concentrations employed. Acceptable carriers and excipients may include buffers, antioxidants, preservatives, polymers, amino acids, and carbohydrates. Pharmaceutical compositions can be administered parenterally in the form of an injectable formulation. Pharmaceutical compositions for injection can be formulated using a sterile solution or any pharmaceutically acceptable liquid as a vehicle. Pharmaceutically acceptable vehicles include, but are not limited to, sterile water, physiological saline, and cell culture media (e.g., Dulbecco's Modified Eagle Medium (DMEM), α-Modified Eagles Medium (α-MEM), F-12 medium). Formulation methods are known in the art, see e.g., Banga (ed.) *Therapeutic Peptides and Proteins: Formulation, Processing and Delivery Systems* (2nd ed.) Taylor & Francis Group, CRC Press (2006).

In some embodiments, the composition is administered parenterally. In some embodiments, the composition is administered intravenously or subcutaneously. In some embodiments, the composition is administered intraperitoneal, intradermally, or intramuscularly. In some embodiments, the composition is administered intravenously. In some embodiments, the composition is administered subcutaneously. In some embodiments, the composition is administered using an infusion pump. In some embodiments, the composition is administered using an autoinjector. In some embodiments, the composition is administered using a patch pump injector. In some embodiments, the composition is administered using a wearable injector. In some embodiments, the composition is administered using a Sorrel™ pump. In some embodiments, the composition is administered using a pump, such as those in U.S. Pat. No. 9,943,642, which is hereby incorporated in its entirety.

In some embodiments, formulations can be prepared with different concentrations of sodium chloride, Trehalose, and surfactant polysorbate (PS) 80, buffered agents and buffered at different pH (pH 5 to 8, pH 6 to 7, or pH 5 to 7). In some embodiments, the compositions include both an ionic osmolyte stabilizer (sodium chloride) and non-ionic osmolyte stabilizer (trehalose). The stability of the formulations and compositions can be assessed over time by appearance, pH, protein concentration, size purity, charge distribution, and thermal stability. These stability parameters can be measured by analytical techniques including pH, UV-Vis, size exclusion chromatography, ion exchange chromatography, CE-SDS, and differential scanning calorimetry.

The composition for infusion can be an aqueous composition that is physiologically compatible (e.g., buffered to a physiological pH and substantially isotonic. The composition can include, for example: sodium chloride, Trehalose, and surfactant polysorbate (PS) 80, and buffered agents. The composition can include both an ionic osmolyte stabilizer (sodium chloride) and non-ionic osmolyte stabilizer (trehalose).

In some embodiments, the infusion is infusion of a composition comprising about 10 to about 60 mg/ml of the antibody described herein, about 20 mM to about 30 mM sodium phosphate, about 20 mM to about 30 mM sodium chloride, about 80 mg/ml to about 100 mg/ml Trehalose, and about 0.1% w/v to about 0.005% w/v Polysorbate 80. In certain embodiments, the antibody described herein is administered at about 5 mg/kg to about 30 mg/kg. In certain embodiments, the concentration of antibody described herein in the intravenous infusion is about 10 mg/ml to about 30 mg/ml. In certain embodiments, the concentration of antibody described herein in the subcutaneous infusion is about 10 mg/ml to about 30 mg/ml.

In some embodiments, a suitable formulation may include about 25 mM sodium phosphate, about 25 mM sodium chloride, about 90.5 mg/ml Trehalose, about 0.01% polysorbate (PS) 80, and the antibody described herein at about 10 mg/ml, about 15 mg/ml, or about 30 mg/ml buffered at pH 6.5. In certain embodiments, a suitable formulation may include about 25 mM sodium succinate, about 25 mM sodium chloride, about 90.5 mg/ml Trehalose, about 0.01% polysorbate (PS) 80, and the antibody described herein at about 10 mg/ml, about 15 mg/ml, or about 30 mg/ml buffered at pH 6.6 or pH 6.5. The stability of the aforementioned two formulations can be further tested in presence of select mechanical, thermal, and chemical stresses. In some embodiments, the stability of the composition can be maintained for more than 30 months for the formulation about 25 mM sodium phosphate, about 25 mM sodium chloride, about 90.5 mg/ml Trehalose, about 0.01% polysorbate (PS) 80, and the antibody described herein at about 10 mg/ml, about 15 mg/ml, or about 30 mg/ml buffered at pH 6.5. In various embodiments, formulations can comprise about 25 mM sodium phosphate, about 25 mM sodium chloride, about 90.5 mg/ml Trehalose, and an antibody disclosed herein, buffered at pH 6.5 with differing amounts of polysorbate 80. In some embodiments, a pharmaceutical composition comprises: an antibody disclosed herein with up to 5 single amino acid insertions, substitutions or deletions at about 10 mg/ml or 30 mg/ml, about 20 mM to about 30 mM sodium phosphate, about 20 mM to about 30 mM sodium chloride, about 80 mg/ml to about 100 mg/ml Trehalose, and about 0.10% w/v to about 0.005% w/v Polysorbate 80, buffered at pH 6.5. In some embodiments, a suitable formulation may include about 25 mM sodium phosphate, about 25 mM sodium chloride, about 90.5 mg/ml Trehalose, about 0.01% polysorbate (PS) 80, and the antibody described herein at about 10 mg/ml, about 15 mg/ml, or about 30 mg/ml buffered at pH 5 to pH 8. In certain embodiments, a suitable formulation may include about 25 mM sodium succinate, about 25 mM sodium chloride, about 90.5 mg/ml Trehalose, about 0.01% polysorbate (PS) 80, and the antibody described herein at about 10 mg/ml, about 15 mg/ml, or about 30 mg/ml buffered at pH 5 to pH 7. In some embodiments, the stability of the composition can be maintained for more than 30 months for the formulation about 25 mM sodium phosphate, about 25 mM sodium chloride, about 90.5 mg/ml Trehalose, about 0.01% polysorbate (PS) 80, and the antibody described herein at about 10 mg/ml, about 15 mg/ml, or about 30 mg/ml buffered at pH 6 to pH 7. In some embodiments, the stability of the composition can be maintained for more than 30 months for the formulation about 25 mM sodium phosphate, about 25 mM sodium chloride, about 90.5 mg/ml Trehalose, about 0.01% polysorbate (PS) 80, and the antibody described herein at about 10 mg/ml, about 15 mg/ml, or about 30 mg/ml buffered at pH 5 to pH 8. In various embodiments, formulations can comprise about 25 mM sodium phosphate, about 25 mM sodium chloride, about 90.5 mg/ml Trehalose, and an antibody disclosed herein, buffered at pH 5 to pH 8, pH 6 to 7, or pH 5 to pH 7. with differing amounts of polysorbate 80. In some embodiments, a pharmaceutical composition comprises: an antibody disclosed herein with up to 5 single amino acid insertions, substitutions or deletions at about 10 mg/ml or 30 mg/ml, about 20 mM to about 30 mM sodium phosphate, about 20 mM to about 30 mM sodium chloride, about 80 mg/ml to about 100 mg/ml Trehalose, and about 0.10% w/v to about 0.005% w/v Polysorbate 80, buffered at pH 5 to pH 8, or pH 5 to pH 7.

V. Routes, Dosage, and Administration

Pharmaceutical compositions that contain one or more anti-FcRn antibodies as the therapeutic proteins may be formulated for intravenous or subcutaneous administration. In preferred embodiments, the pharmaceutical composition comprises nipocalimab.

Described herein are methods of treating various disorders comprising intravenous or subcutaneous administration of about 5 mg/kg to about 120 mg/kg dose of an anti-FcRn antibody as described herein to a subject. In some embodiments, the anti-FcRn antibody comprises a heavy chain comprising a HCDR1 of SEQ ID NO: 6, a HCDR2 of SEQ ID NO: 7, and a HCDR3 of SEQ ID NO: 8; and a light chain comprising a LCDR1 of SEQ ID NO: 3, a LCDR2 of SEQ ID NO: 4, and a LCDR3 of SEQ ID NO: 5. In preferred embodiments, the anti-FcRn antibody is nipocalimab. The methods described herein include an initial administration (e.g., a loading dose or induction) at a first dose level followed by subsequent administrations at a different or maintenance dose level.

In some embodiments, the anti-FcRn antibody is administered at an initial loading dose that is about 5 mg/kg to about 120 mg/kg followed by biweekly maintenance dose of about 5 mg/kg to about 60 mg/kg. In some embodiments, the anti-FcRn antibody is administered at an initial loading dose that is about 5 mg/kg to about 60 mg/kg followed by biweekly maintenance dose of about 5 mg/kg to about 30 mg/kg. In some embodiments, the anti-FcRn antibody is administered at an initial loading dose that is about 60 mg/kg followed by biweekly maintenance dose of about 30 mg/kg. In some embodiments, the anti-FcRn antibody is administered at an initial loading dose that is about 60 mg/kg followed by biweekly maintenance dose of about 15 mg/kg. In some embodiments, the anti-FcRn antibody is administered at an initial loading dose that is about 30 mg/kg followed by biweekly maintenance dose of about 30 mg/kg. In some embodiments, the anti-FcRn antibody is administered at an initial loading dose that is about 30 mg/kg followed by biweekly maintenance dose of about 15 mg/kg. In some embodiments, the anti-FcRn antibody is administered at an initial loading dose that is about 5 mg/kg to about 120 mg/kg followed by a maintenance dose of about 5 mg/kg to about 60 mg/kg every four weeks. In some embodiments, the anti-FcRn antibody is administered at an initial loading dose that is about 5 mg/kg to about 60 mg/kg followed by a maintenance dose of about 5 mg/kg to about 30 mg/kg every four weeks. In some embodiments, the anti-FcRn antibody is administered at an initial loading dose that is about 60 mg/kg followed by a maintenance dose of about 30 mg/kg every four weeks. In some embodiments, the anti-FcRn antibody is administered at an initial loading dose that is about 60 mg/kg followed by a maintenance dose of about 15 mg/kg every four weeks. In some embodiments, the anti-FcRn antibody is administered at an initial loading dose that is about 30 mg/kg followed by a maintenance dose of about 30 mg/kg every four weeks. In some embodiments, the anti-FcRn antibody is administered at an initial loading dose that is about 30 mg/kg followed by a maintenance dose of about 15 mg/kg every four weeks. In some embodiments, the anti-FcRn antibody is administered at an initial loading dose that is about 5 mg/kg to about 120 mg/kg followed by monthly maintenance dose of about 5 mg/kg to about 60 mg/kg. In some embodiments, the anti-FcRn antibody is administered at an initial loading dose that is about 5 mg/kg to about 60 mg/kg followed by monthly maintenance dose of about 5 mg/kg to about 30 mg/kg. In some embodiments, the anti-FcRn antibody is administered at an initial loading dose that is about 5 mg/kg to about 60 mg/kg followed by biweekly maintenance dose of about 5 mg/kg to about 15 mg/kg. In some embodiments, the anti-FcRn antibody is administered at an initial loading dose that is about 5 mg/kg to about 60 mg/kg followed by monthly maintenance dose of about 5 mg/kg to about 15 mg/kg. In some embodiments, the anti-FcRn antibody is administered at an initial loading dose that is about 60 mg/kg followed by monthly maintenance dose of about 15 mg/kg. In some embodiments, the anti-FcRn antibody is administered at an initial loading dose that is about 60 mg/kg followed by monthly maintenance dose of about 30 mg/kg. In preferred embodiments, the anti-FcRn antibody is administered at an initial loading dose that is about 30 mg/kg followed by monthly maintenance dose of about 15 mg/kg. In some embodiments, the anti-FcRn antibody is administered at an initial loading dose that is about 30 mg/kg followed by monthly maintenance dose of about 30 mg/kg. In preferred embodiments, the anti-FcRn antibody is preferably nipocalimab. In some embodiments, the anti-FcRn antibody is administered intravenously. In some embodiments, the anti-FcRn antibody is administered subcutaneously. In some embodiments, the initial loading dose is administered intravenously, and the maintenance dose is administered subcutaneously.

In some embodiments, the methods described herein comprise administering the anti-FcRn antibody to an adult subject or patient. The terms “adult subject” or “adult patient” can be used interchangeably. An adult subject as used herein is a subject of 18 years or older, e.g. in certain embodiments an adult subject is 18-100 years old, 19-90 years old, e.g. at least 20, 25, 30, 35, 40, 45, 50, 55, 60, 65, 70, 75, 80, 85, 90, or 95 years old.

In some embodiments, the methods described herein comprise administering the anti-FcRN antibody to a pediatric subject or patient. The terms “pediatric subject” or “pediatric patient” can be used interchangeably. In some embodiments, a pediatric subject is less than 18 years old. In some embodiments, the pediatric subject is about 12 to less than 18 years old. In some embodiments, the pediatric subject is about to about 12 years old. In some embodiments, the pediatric subject is less than 12 years old. In some embodiments, the pediatric subject is 2 to 12 years old. In some embodiments, the pediatric patient is an adolescent pediatric patient. In some embodiments, the adolescent pediatric patient is aged 12 to less than 18 years old.

In some embodiments, the antibody is administered at an initial dose that is 60 mg/kg. In some embodiments, the antibody is administered at an initial dose that is 30 mg/kg In some embodiments, the antibody is administered at a dose from about 5 mg/kg to about 60 mg/kg, about 5 mg/kg to about 15 mg/kg, about 15 mg/kg to about 60 mg/kg, or about 30 mg/kg to about 60 mg/kg. In some embodiments, the antibody is administered at a dose of about 5 mg/kg, about 15 mg/kg, about 30 mg/kg, about 45 mg/kg, or about 60 mg/kg. In some embodiments, the antibody is administered at a dose of, or about, 5, 10, 15, 20, 25, 30, 35, 40, 45, 50, 55, or 60 mg/kg. In some embodiments, the antibody is administered at a single dose, or at an initial loading dose and a maintenance dose. In some embodiments, the initial loading dose and the maintenance dose are at the same dose. In some embodiments, the loading dose and the maintenance dose are not the same dose. In preferred embodiments, the loading dose is greater than the maintenance dose. In some embodiments, the loading dose is administered at a dose from about 5 mg/kg to about 60 mg/kg, about 5 mg/kg to about 15 mg/kg, about 15 mg/kg to about 60 mg/kg, or about 30 mg/kg to about 60 mg/kg. In some embodiments, the loading dose is administered at a dose of 60 mg/kg. In some embodiments, the loading dose is administered at a dose of 30 mg/kg. In some embodiments, the maintenance dose is administered at a dose from about 5 mg/kg to about 60 mg/kg, about 5 mg/kg to about 15 mg/kg, about 15 mg/kg to about 60 mg/kg, or about 30 mg/kg to about 60 mg/kg. In some embodiments, the maintenance dose is administered at a dose of about 5 mg/kg, about 15 mg/kg, about 30 mg/kg, about 45 mg/kg, or about 60 mg/kg. In some embodiments, the maintenance dose is administered at a dose of 5, 10, 15, 20, 25, 30, 35, 40, 45, 50, 55, or 60 mg/kg. In some embodiments, the maintenance dose is administered at a dose of 15 mg/kg. In some embodiments, the loading dose is administered at a dose of about 30 mg/kg and a maintenance dose of about 15 mg/kg. In preferred embodiments, the loading dose is administered at a dose of 30 mg/kg and a maintenance dose of 15 mg/kg.

In some embodiments, the administration reduces serum IgG in the patient by at least 10%, at least 20%, at least 30%, at least 40%, at least 50%, at least 60%, at least 70%, at least 80%, or at least 90% of baseline serum IgG. In some embodiments, the methods can include administering a loading dose that reduces serum IgG by at least 65% to at least 85% compared to baseline. The methods can include administering a loading dose that reduces serum IgG by at least 36% to at least 64% compared to baseline. The methods can include administering a loading dose that reduces serum IgG by at least 15% to at least 35% compared to baseline. The loading dose decreases the IgG levels by at least 20% to at least 35% (e.g., at least 20%, at least 25%, at least 30%, at least 35%) of baseline within the first about 1 week to about 2 weeks of treatment.

The loading dose can be followed by a maintenance dose that is about 75%, about 50%, about 25%, about 20%, about 15%, about 10%, or about 5% of the loading dose. In certain embodiments, the maintenance dose is administered every 2 weeks, every 3 weeks, or every 4 weeks. The maintenance dose maintains the serum IgG levels at a reduced level below baseline (e.g., maintains serum IgG at a level that is at least 65% to at least 85%, at least 36% to at least 64%, or at least 15% to at least 35% of baseline). The maintenance dosing method in certain embodiments maintains the serum IgG at a level that is at least 20% to at least 35% (e.g., at least 20%, at least 25%, at least 30%, at least 35%) of baseline.

In some embodiments, the initial loading dose is 60 mg/kg administered intravenously and is followed 1 week, 2 weeks, 3 weeks, or 4 weeks later by biweekly (Q2W) administration of a 15 mg/kg maintenance dose administered intravenously. In some embodiments, the initial loading dose is 60 mg/kg administered intravenously and is followed 1 week, 2 weeks, 3 weeks, or 4 weeks later by biweekly (Q2W) administration of a 30 mg/kg maintenance dose administered intravenously. In some embodiments, the initial loading dose is 30 mg/kg administered intravenously and is followed 1 week, 2 weeks, 3 weeks, or 4 weeks later by biweekly (Q2W) administration of a 15 mg/kg maintenance dose administered intravenously. In some embodiments, the initial loading dose is 30 mg/kg administered intravenously and is followed 1 week, 2 weeks, 3 weeks, or 4 weeks later by biweekly (Q2W) administration of a 30 mg/kg maintenance dose administered intravenously.

In some embodiments, the initial loading dose is 60 mg/kg administered intravenously and is followed 1 week, 2 weeks, 3 weeks, or 4 weeks later by monthly administration of a 15 mg/kg maintenance dose administered intravenously. In some embodiments, the initial loading dose is 60 mg/kg administered intravenously and is followed 1 week, 2 weeks, 3 weeks, or 4 weeks later by monthly administration of a 30 mg/kg maintenance dose administered intravenously. In some embodiments, the initial loading dose is 30 mg/kg administered intravenously and is followed 1 week, 2 weeks, 3 weeks, or 4 weeks later by monthly administration of a 15 mg/kg maintenance dose administered intravenously. In some embodiments, the initial loading dose is 30 mg/kg administered intravenously and is followed 1 week, 2 weeks, 3 weeks, or 4 weeks later by monthly administration of a 30 mg/kg maintenance dose administered intravenously.

In some embodiments, the initial loading dose is 60 mg/kg administered intravenously and is followed 1 week, 2 weeks, 3 weeks, or 4 weeks later by biweekly (Q2W) administration of a 15 mg/kg maintenance dose administered subcutaneously. In some embodiments, the initial loading dose is 60 mg/kg administered intravenously and is followed 1 week, 2 weeks, 3 weeks, or 4 weeks later by biweekly (Q2W) administration of a 30 mg/kg maintenance dose administered subcutaneously. In some embodiments, the initial loading dose is 30 mg/kg administered intravenously and is followed 1 week, 2 weeks, 3 weeks, or 4 weeks later by biweekly (Q2W) administration of a 15 mg/kg maintenance dose administered subcutaneously. In some embodiments, the initial loading dose is 30 mg/kg administered intravenously and is followed 1 week, 2 weeks, 3 weeks, or 4 weeks later by biweekly (Q2W) administration of a 30 mg/kg maintenance dose administered subcutaneously.

In some embodiments, the initial loading dose is 60 mg/kg administered intravenously and is followed 1 week, 2 weeks, 3 weeks, or 4 weeks later by monthly administration of a 15 mg/kg maintenance dose administered subcutaneously. In some embodiments, the initial loading dose is 60 mg/kg administered intravenously and is followed 1 week, 2 weeks, 3 weeks, or 4 weeks later by monthly administration of a 30 mg/kg maintenance dose administered subcutaneously. In some embodiments, the initial loading dose is 30 mg/kg administered intravenously and is followed 1 week, 2 weeks, 3 weeks, or 4 weeks later by monthly administration of a 15 mg/kg maintenance dose administered subcutaneously. In some embodiments, the initial loading dose is 30 mg/kg administered intravenously and is followed 1 week, 2 weeks, 3 weeks, or 4 weeks later by monthly administration of a 30 mg/kg maintenance dose administered subcutaneously.

In some embodiments, the initial loading dose is 60 mg/kg administered subcutaneously and is followed 1 week, 2 weeks, 3 weeks, or 4 weeks later by biweekly (Q2W) administration of a 15 mg/kg maintenance dose administered subcutaneously. In some embodiments, the initial loading dose is 60 mg/kg administered subcutaneously and is followed 1 week, 2 weeks, 3 weeks, or 4 weeks later by biweekly (Q2W) administration of a 30 mg/kg maintenance dose administered subcutaneously. In some embodiments, the initial loading dose is 30 mg/kg administered subcutaneously and is followed 1 week, 2 weeks, 3 weeks, or 4 weeks later by biweekly (Q2W) administration of a 15 mg/kg maintenance dose administered subcutaneously. In some embodiments, the initial loading dose is 30 mg/kg administered subcutaneously and is followed 1 week, 2 weeks, 3 weeks, or 4 weeks later by biweekly (Q2W) administration of a 30 mg/kg maintenance dose administered subcutaneously.

In some embodiments, the initial loading dose is 60 mg/kg administered subcutaneously and is followed 1 week, 2 weeks, 3 weeks, or 4 weeks later by monthly administration of a 15 mg/kg maintenance dose administered subcutaneously. In some embodiments, the initial loading dose is 60 mg/kg administered subcutaneously and is followed 1 week, 2 weeks, 3 weeks, or 4 weeks later by monthly administration of a 30 mg/kg maintenance dose administered subcutaneously. In some embodiments, the initial loading dose is 30 mg/kg administered subcutaneously and is followed 1 week, 2 weeks, 3 weeks, or 4 weeks later by monthly administration of a 15 mg/kg maintenance dose administered subcutaneously. In some embodiments, the initial loading dose is 30 mg/kg administered subcutaneously and is followed 1 week, 2 weeks, 3 weeks, or 4 weeks later by monthly administration of a 30 mg/kg maintenance dose administered subcutaneously.

In some embodiments, the administration of the antibody is an intravenous infusion. In some embodiments, the administration of the antibody is a subcutaneous infusion. In some embodiments, the antibody is administered at a dose of about 5, about 10, about 15, about 20, about 25, about 30, about 35, about 40, about 45, about 50, about 55, or about 60 mg/kg. In some embodiments, the antibody is administered at least every week, every two weeks, every three weeks, or every four weeks (i.e., once a month).

In some embodiments, a first infusion of the antibody is administered at a loading dose of about 60 mg/kg and a second infusion of the antibody is administered weekly at a maintenance dose of 15 mg/kg. In some embodiments, a first infusion of the antibody is administered at a loading dose of about 60 mg/kg and a second infusion of the antibody is administered every 2 weeks at a maintenance dose of 15 mg/kg. In some embodiments, a first infusion of the antibody is administered at a loading dose of about 60 mg/kg and a second infusion of the antibody is administered every 3 weeks at a maintenance dose of 15 mg/kg. In some embodiments, a first infusion of the antibody is administered at a loading dose of about 60 mg/kg and a second infusion of the antibody is administered every 4 weeks at a maintenance dose of 15 mg/kg.

In some embodiments, a first infusion of the antibody is administered at a loading dose of about 30 mg/kg and a second infusion of the antibody is administered weekly at a maintenance dose of 15 mg/kg. In some embodiments, a first infusion of the antibody is administered at a loading dose of about 30 mg/kg and a second infusion of the antibody is administered every 2 weeks at a maintenance dose of 15 mg/kg. In some embodiments, a first infusion of the antibody is administered at a loading dose of about 30 mg/kg and a second infusion of the antibody is administered every 3 weeks at a maintenance dose of 15 mg/kg. In some embodiments, a first infusion of the antibody is administered at a loading dose of about 30 mg/kg and a second infusion of the antibody is administered every 4 weeks at a maintenance dose of 15 mg/kg.

In some embodiments, a first infusion of the antibody is administered at a loading dose of about 60 mg/kg and a second infusion of the antibody is administered weekly at a maintenance dose of 30 mg/kg. In some embodiments, a first infusion of the antibody is administered at a loading dose of about 60 mg/kg and a second infusion of the antibody is administered every 2 weeks at a maintenance dose of 30 mg/kg. In some embodiments, a first infusion of the antibody is administered at a loading dose of about 60 mg/kg and a second infusion of the antibody is administered every 3 weeks at a maintenance dose of 30 mg/kg. In some embodiments, a first infusion of the antibody is administered at a loading dose of about 60 mg/kg and a second infusion of the antibody is administered every 4 weeks at a maintenance dose of 30 mg/kg.

In some embodiments, a first infusion of the antibody is administered at a loading dose of about 30 mg/kg and a second infusion of the antibody is administered weekly at a maintenance dose of 30 mg/kg. In some embodiments, a first infusion of the antibody is administered at a loading dose of about 30 mg/kg and a second infusion of the antibody is administered every 2 weeks at a maintenance dose of 30 mg/kg. In some embodiments, a first infusion of the antibody is administered at a loading dose of about 30 mg/kg and a second infusion of the antibody is administered every 3 weeks at a maintenance dose of 30 mg/kg. In some embodiments, a first infusion of the antibody is administered at a loading dose of about 30 mg/kg and a second infusion of the antibody is administered every 4 weeks at a maintenance dose of 30 mg/kg.

In some embodiments, additional infusions are performed at a maintenance dose of 15 mg/kg. In some embodiments, additional infusions are performed at a maintenance dose of 30 mg/kg. In some embodiments, the infusions (including the first, second, and/or additional) are administered every two weeks, every 3 weeks, or every 4 weeks. In some embodiments, the method includes an initial (loading) dose followed by a biweekly (e.g., every two weeks) maintenance dose. In some embodiments, the method includes an initial (loading) dose followed by an every 3 weeks maintenance dose. In some embodiments, the method includes an initial (loading) dose followed by an every month maintenance dose. In some embodiments, the initial dose is higher than the biweekly maintenance dose. In some embodiments, the loading dose provides a stronger week 1-2 IgG reduction (e.g., greater decrease in IgG levels).

The pharmaceutical compositions are administered in a manner and rate compatible with the dosage formulation. In some embodiments, the subject receives a single dose of about 30 mg/kg or about 60 mg/kg antibody by intravenous infusion over 90 minutes or less. In some embodiments, the intravenous infusion takes please over 60 minutes or less, 45 minutes or less, 30 minutes or less, 15 minutes or less, or 7 minutes or less. In some embodiments, the subject receives a single dose of about 30 mg/kg or about 60 mg/kg antibody by subcutaneous infusion over 90 minutes or less. In some embodiments, the subcutaneous infusion takes please over 60 minutes or less, 45 minutes or less, 30 minutes or less, 15 minutes or less, or 7 minutes or less. In some embodiments, the infusion of a dose of the antibody takes place over about 7 minutes to about 90 minutes, about 7 minutes to about 60 minutes, about 7 minutes to about 45 minutes, about 7 minutes to about 30 minutes, about 10 minutes to about 90 minutes, about 10 minutes to about 60 minutes, about 10 minutes to about 45 minutes, about 10 minutes to about 30 minutes, about 15 minutes to about 30 minutes, about 30 minutes to about 90 minutes, or about 15 minutes to about 60 minutes.

In some embodiments, the initial loading dose is infused into the subject in about 30 minutes to about 90 minutes. In some embodiments, the maintenance dose is infused into the subject in about 15 minutes to about 60 minutes. In some embodiments, the subject receives a dose of about 30 mg/kg antibody by intravenous infusion over 15 minutes. In some embodiments, the subject receives a dose of about 30 mg/kg antibody by intravenous infusion over 30 minutes. In some embodiments, the subject receives a dose of about 45 mg/kg antibody by intravenous infusion over 15 minutes. In some embodiments, the subject receives a dose of about 45 mg/kg antibody by intravenous infusion over 30 minutes. In some embodiments, the subject receives a dose of about 60 mg/kg antibody by intravenous infusion over 30 minutes. In some embodiments, the subject receives a dose of about 30 mg/kg antibody by intravenous infusion over 60 minutes. In some embodiments, the subject receives a dose of about 30 mg/kg to about 60 mg/kg by intravenous infusion over a first period of time for a first infusion and a second period of time for a second infusion. In some cases, the first period of time is longer than the second period of time. In some cases, the second infusion is the second administration of the antibody. In some cases, the subject receives a dose of about 30 mg/kg by intravenous infusion over a period of 30 minutes for the first period of time for the first infusion and a period of 15 minutes for the second period of time for the second infusion. In some cases, the subject receives a dose of about 45 mg/kg by intravenous infusion over a period of 30 minutes for the first period of time for the first infusion and a period of 15 minutes for the second period of time for the second infusion. In some cases, the subject receives a dose of about 60 mg/kg by intravenous infusion over a period of 60 minutes for the first period of time for the first infusion and a period of 30 minutes for the second period of time for the second infusion. In some embodiments, the subject receives a dose of about 30 mg/kg antibody by subcutaneous infusion over 15 minutes. In some embodiments, the subject receives a dose of about 30 mg/kg antibody by subcutaneous infusion over 30 minutes. In some embodiments, the subject receives a dose of about 45 mg/kg antibody by subcutaneous infusion over 15 minutes. In some embodiments, the subject receives a dose of about 45 mg/kg antibody by subcutaneous infusion over 30 minutes. In some embodiments, the subject receives a dose of about 60 mg/kg antibody by subcutaneous infusion over 30 minutes. In some embodiments, the subject receives a dose of about 30 mg/kg antibody by subcutaneous infusion over 60 minutes. In some embodiments, the subject receives a dose of about 30 mg/kg to about 60 mg/kg by subcutaneous infusion over a first period of time for a first infusion and a second period of time for a second infusion. In some cases, the first period of time is longer than the second period of time. In some cases, the second infusion is the second administration of the antibody. In some cases, the subject receives a dose of about 30 mg/kg by subcutaneous infusion over a period of 30 minutes for the first period of time for the first infusion and a period of 15 minutes for the second period of time for the second infusion. In some cases, the subject receives a dose of about 45 mg/kg by subcutaneous infusion over a period of 30 minutes for the first period of time for the first infusion and a period of 15 minutes for the second period of time for the second infusion. In some cases, the subject receives a dose of about 60 mg/kg by subcutaneous infusion over a period of 60 minutes for the first period of time for the first infusion and a period of 30 minutes for the second period of time for the second infusion. The dosage and rate of administration of the pharmaceutical compositions depends on factors including the prior treatment of the subject, the disease to be treated, and physical characteristics, e.g., age, weight, general health, of the subject.

TABLE 1

Examples of Dosing Regimens Subsequent to Initial (loading) Dose (e.g., 60 mg/kg)

| Regimen type | Maintenance Dose | Frequency |
|---|---|---|
| Consistent dose and frequency | 45 mg/kg | Every two weeks |
| Consistent dose and frequency | 45 mg/kg | Every one week |
| Consistent dose and frequency | 45 mg/kg | Every three weeks |
| Consistent dose and frequency | 45 mg/kg | Every month |
| Consistent dose and frequency | 30 mg/kg | Every two weeks |
| Consistent dose and frequency | 30 mg/kg | Every three weeks |
| Consistent dose and frequency | 30 mg/kg | Every month |
| Consistent dose and frequency | 15 mg/kg | Every two weeks |
| Consistent dose and frequency | 15 mg/kg | Every three weeks |
| Consistent dose and frequency | 15 mg/kg | Every month |
| Consistent dose and frequency | 5 mg/kg | Every two weeks |
| Consistent dose and frequency | 5 mg/kg | Every three weeks |
| Consistent dose and frequency | 5 mg/kg | Every month |

TABLE 2

Examples of Dosing Regimens Subsequent to Initial (loading) Dose (e.g., 60 mg/kg) including time for each subsequent infusion which can occur every 1 week, every 2 weeks, every 3 weeks or every 4 weeks.

| Maintenance Dose | Time for first infusion | Time for second infusion | Time for any subsequent infusion |
|---|---|---|---|
| 30 mg/kg | 30 min | 30 min | 15 min |
| 30 mg/kg | 30 min | 15 min | 15 min |
| 30 mg/kg | 15 min | 15 min | 15 min |
| 15 mg/kg | 30 min | 30 min | 15 min |
| 15 mg/kg | 30 min | 15 min | 15 min |
| 15 mg/kg | 15 min | 15 min | 15 min |
| 5 mg/kg | 30 min | 30 min | 15 min |
| 5 mg/kg | 30 min | 15 min | 15 min |
| 5 mg/kg | 15 min | 15 min | 15 min |

In some embodiments of all the methods described herein, the infusion is infusion of a composition comprising about 15 mg/ml to about 60 mg/ml of the antibody. In some embodiments of all the methods described herein, the infusion is infusion of a composition comprising about 15 mg/ml, about 30 mg/ml, about 45 mg/ml, or about 60 mg/ml of the antibody. In some embodiments of all the methods described herein, the infusion is infusion of a composition comprising about 15 mg/ml of the antibody. In some embodiments of all the methods described herein, the infusion is infusion of a composition comprising about 30 mg/ml of the antibody. In some embodiments of all the methods described herein, the infusion is infusion of a composition comprising about 60 mg/ml of the antibody. In preferred embodiments, the antibody is an anti-FcRn antibody, most preferably, the anti-FcRn antibody is nipocalimab. In some embodiments, the anti-FcRn antibody comprises the variable region heavy chain comprising a sequence having at least 95%, 96%, 97%, 98%, 99%, or 100% identity to the sequence of SEQ ID NO: 10 and the variable region light chain comprising a sequence having at least 95%, 96%, 97%, 98%, 99%, or 100% identity to the sequence of SEQ ID NO: 9. In some embodiments, the anti-FcRn antibody comprises the heavy chain comprising a sequence having at least 95%, 96%, 97%, 98%, 99%, or 100% identity to the sequence of SEQ ID NO: 2 and the light chain comprising a sequence having at least 95%, 96%, 97%, 98%, 99%, or 100% identity to the sequence of SEQ ID NO: 1.

In some embodiments, the infusion is an infusion of a composition comprising about 15 mg/ml to about 60 mg/ml (or about 15 mg/ml, about 20 mg/ml, about 30 mg/ml, about 40 mg/ml, about 50 mg/ml, about 60 mg/ml) of the antibody described herein, about 20 mM to about 30 mM sodium phosphate, about 20 mM to about 30 mM sodium chloride, about 80 mg/ml to about 100 mg/ml Trehalose, and about 0.1% w/v to about 0.005% w/v Polysorbate 80 at pH 6.5. In some embodiments, the infusion is an infusion of a composition comprising about 15 mg/ml to about 60 mg/ml (or about 15 mg/ml, about 20 mg/ml, about 30 mg/ml, about 40 mg/ml, about 50 mg/ml, about 60 mg/ml) of the antibody described herein, about 20 mM to about 30 mM sodium phosphate, about 20 mM to about 30 mM sodium chloride, about 80 mg/ml to about 100 mg/ml Trehalose, and about 0.1% w/v to about 0.005% w/v Polysorbate 80 at pH 5 to pH 8. In some embodiments, the infusion is an infusion of a composition comprising about 15 mg/ml to about 60 mg/ml (or about 15 mg/ml, about 20 mg/ml, about 30 mg/ml, about 40 mg/ml, about 50 mg/ml, about 60 mg/ml) of the antibody described herein, about 20 mM to about 30 mM sodium phosphate, about 20 mM to about 30 mM sodium chloride, about 80 mg/ml to about 100 mg/ml Trehalose, and about 0.1% w/v to about 0.005% w/v Polysorbate 80 at pH 6 to pH 7. In some embodiments, the infusion is an infusion of a composition comprising about 15 mg/ml to about 60 mg/ml (or about 15 mg/ml, about 20 mg/ml, about 30 mg/ml, about 40 mg/ml, about 50 mg/ml, about 60 mg/ml) of the antibody described herein, about 20 mM to about 30 mM sodium phosphate, about 20 mM to about 30 mM sodium chloride, about 80 mg/ml to about 100 mg/ml Trehalose, and about 0.1% w/v to about 0.005% w/v Polysorbate 80 at pH 5 to pH 7.

In some embodiments of all the methods described herein, the antibody is administered at about 15 mg/kg to about 30 mg/kg. In some embodiments of all the methods described herein, the antibody is administered at about 30 mg/kg to about 60 mg/kg. In some embodiments of all the methods described herein, the concentration of antibody in the intravenous infusion is about 15 mg/ml to about 30 mg/ml. In some embodiments of all the methods described herein, the concentration of antibody in the intravenous infusion is about 30 mg/ml to about 60 mg/ml. In some embodiments of all the methods described herein, the concentration of antibody in the subcutaneous infusion is about 15 mg/ml to about 30 mg/ml. In some embodiments of all the methods described herein, the concentration of antibody in the subcutaneous infusion is about 30 mg/ml to about 60 mg/ml.

In some embodiments of all the methods described herein, the second fusion and the third fusion times are identical, takes place over 60 minutes or less, 45 minutes or less, 30 minutes or less, 15 minutes or less, or 7 minutes or less, and subsequent infusion times are reduced.

In some embodiments of all the methods described herein, the first infusion and the second fusion times are identical, take place over 90 minutes or less, 60 minutes or less, 45 minutes or less, 30 minutes or less, 15 minutes or less, and subsequent infusion times are reduced. In some embodiments of all the methods described herein, the first infusion and the second fusion both take place over 60 minutes and subsequent infusions take place over 45 minutes or less, 30 minutes or less, or 15 minutes or less; or the first infusion and the second fusion both take place over 45 minutes and subsequent infusions take place over 30 minutes or less or 15 minutes or less; or the first infusion and the second fusion both take place over 30 minutes and subsequent infusions take place over 15 minutes or less. In some embodiments, the infusion times are identical and takes place over 90 minutes or less, 60 minutes or less, 45 minutes or less, 30 minutes or less, 15 minutes or less, or 7 minutes or less. In various aspects of all methods, the first infusion takes place over 90 minutes or less, 60 minutes or less, 45 minutes or less, 30 minutes or less, 15 minutes or less, and subsequent infusion times are reduced. In some embodiments, the second fusion and the third fusion times are identical, takes place over 60 minutes or less, 45 minutes or less, 30 minutes or less, 15 minutes or less, or 7 minutes or less, and subsequent infusion times are reduced. In various aspects of all methods, the first infusion and the second fusion times are identical, take place over 90 minutes or less, 60 minutes or less, 45 minutes or less, 30 minutes or less, 15 minutes or less, and subsequent infusion times are reduced. In various aspects of all methods, the first infusion takes place over 60 minutes and subsequent infusions take place over 45 minutes or less, 30 minutes or less, or 15 minutes or less; or the first infusion takes place over 45 minutes and subsequent infusions takes place over 30 minutes or less or 15 minutes or less; or the first infusion takes place over 30 minutes and subsequent infusions takes place over 15 minutes or less. In various aspects of all methods, the first infusion and the second fusion both take place over 60 minutes and subsequent infusions take place over 45 minutes or less, 30 minutes or less, or 15 minutes or less; or the first infusion and the second fusion both take place over 45 minutes and subsequent infusions take place over 30 minutes or less or 15 minutes or less; or the first infusion and the second fusion both take place over 30 minutes and subsequent infusions take place over 15 minutes or less.

In some embodiments, the composition is administered parenterally. In some embodiments, the composition is administered intravenously or subcutaneously. In some embodiments, the composition is administered intraperitoneal, intradermally, or intramuscularly. In some embodiments, the composition is administered intravenously. In some embodiments, the composition is administered subcutaneously. In some embodiments, the composition is administered using an infusion pump. In some embodiments, the composition administered using an autoinjector. In some embodiments, the composition is administered using a patch pump injector. In some embodiments, the composition is administered using a wearable injector. In some embodiments, the composition is administered using a Sorrel™ pump. In some embodiments, the composition is administered using a pump, such as those in U.S. Pat. No. 9,943,642, which is hereby incorporated in its entirety.

In some embodiments, the anti-FcRn antibodies are administered at the rate disclosed herein without the subject experiencing serious adverse events or reactions.

VI. Methods of Treatment and Indications

The blockade of human FcRn by anti-FcRn antibodies may be of therapeutic benefit in diseases that are driven by IgG autoantibodies. The ability of FcRn blockade to induce overall IgG catabolism and removal of multiple species of autoantibodies without perturbing serum albumin, small circulating metabolites, or lipoproteins offers a method to expand the utility and accessibility of an autoantibody removal strategy to patients with autoantibody-driven autoimmune disease pathology. While the disclosure is not bound by theory, the dominant mechanism of action of an anti-FcRn antibody may be to increase the catabolism of pathogenic autoantibodies in circulation and decrease autoantibody and immune complex deposition in affected tissues.

In some embodiments of all aspects, the method treats the pregnant subject, a fetus of the pregnant subject, and/or a combination thereof.

Also described is a method of reducing the risk of or reducing the risk of developing an autoimmune or alloimmune disorder, comprising, consisting of, or consisting essentially of IV administration of an FcRn antibody described herein to a pregnant subject.

In some cases the method includes ceasing administration if the subject exhibits hypoalbuminemia (e.g., a serum albumin level below 30 g/l, 25 g/l, 20 g/l). In some cases the serum albumin level is reduced from baseline during treatment by less than or equal to 25%.

The pharmaceutical compositions and methods containing one or more anti-FcRn antibodies are useful to promote catabolism and clearance of pathogenic antibodies, e.g., IgG and IgG autoantibodies in a subject, to reduce the immune response, e.g., to block immune complex-based activation of the immune response in a subject, and to treat immunological conditions or diseases in a subject. In particular, the pharmaceutical compositions and methods are useful to reduce or treat an immune complex-based activation of an acute or chronic immune response. The acute immune response may be activated by a medical condition selected from the group consisting of pemphigus vulgaris, lupus nephritis, myasthenia gravis, Guillain-Barre syndrome, antibody-mediated rejection, catastrophic anti-phospholipid antibody syndrome, immune complex-mediated vasculitis, glomerulitis, a channelopathy, neuromyelitis optica, autoimmune hearing loss, idiopathic thrombocytopenia purpura (ITP), autoimmune haemolytic anaemia (AIHA), immune neutropenia, dilated cardiomyopathy, and serum sickness. For example, in some embodiments, the acute immune response is activated by a medical condition in the pregnant subject. For example, in some embodiments, the acute immune response is activated in the fetus or neonate by a medical condition in the pregnant subject. In some embodiments of all aspects, the acute immune response is activated by a medical condition in the pregnant subject. In some embodiments of all aspects, the acute immune response is activated in the fetus or neonate by a medical condition in the pregnant subject. In some embodiments of all aspects, the acute immune response is activated by idiopathic thrombocytopenia purpura. In some embodiments of all aspects, the acute immune response is activated by pemphigus vulgaris. In some embodiments of all aspects, the acute immune response is activated by catastrophic anti-phospholipid antibody syndrome. In some embodiments of all aspects, the acute immune response is activated by neuromyelitis optica. In some embodiments of all aspects, the acute immune response is activated by antibody-mediated rejection. In some embodiments of all aspects, the acute immune response is activated by myasthenia gravis. The chronic immune response may be activated by a medical condition selected from the group consisting of chronic inflammatory demyelinating polyneuropathy (CIDP), systemic lupus, a chronic form of a disorder indicated for acute treatment, reactive arthropathies, primary biliary cirrhosis, ulcerative colitis, and antineutrophil cytoplasmic antibody (ANCA)-associated vasculitis. In some embodiments of all aspects, the chronic immune response is activated by chronic inflammatory demyelinating polyneuropathy.

In some embodiments, the pharmaceutical compositions and methods are useful to reduce or treat a disorder selected from the group consisting of Lupus nephritis (LN), Myasthenia gravis (MG), Idiopathic thrombocytopenia purpura, Autoimmune haemolytic anaemia, Chronic inflammatory demyelinating polyneuropathy (CIPD), Bullous pemphigoid (BP), Dermatomyositis Polymyositis, Rheumatoid arthritis (RA), Sjögren's syndrome, Systemic lupus erythematosus (SLE), Hemolytic disease of the fetus and newborn (HDFN), Warm Autoimmune Hemolytic Anemia (wAIHA), maternal fetal medicine (MFM), or Polymyositis and Dermatomyositis (PMDM).

In some embodiments, the pharmaceutical compositions and methods are useful to reduce or treat Lupus nephritis (LN).

In some embodiments, the pharmaceutical compositions and methods are useful to reduce or treat Myasthenia gravis (MG).

In some embodiments, the pharmaceutical compositions and methods are useful to reduce or treat Chronic inflammatory demyelinating polyneuropathy (CIPD).

In some embodiments, the pharmaceutical compositions and methods are useful to reduce or treat Bullous pemphigoid (BP).

In some embodiments, the pharmaceutical compositions and methods are useful to reduce or treat Rheumatoid arthritis (RA).

In some embodiments, the pharmaceutical compositions and methods are useful to reduce or treat Sjögren's syndrome.

In some embodiments, the pharmaceutical compositions and methods are useful to reduce or treat Systemic lupus erythematosus (SLE).

In some embodiments, the pharmaceutical compositions and methods are useful to reduce or treat Hemolytic disease of the fetus and newborn (HDFN).

In some embodiments, the pharmaceutical compositions and methods are useful to reduce or treat Warm Autoimmune Hemolytic Anemia (wAIHA).

In some embodiments, the pharmaceutical compositions and methods are useful to reduce or treat maternal fetal medicine (MFM).

In some embodiments, the pharmaceutical compositions and methods are useful to reduce or treat Polymyositis and Dermatomyositis (PMDM).

In some embodiments, the pharmaceutical compositions and methods are useful to reduce or treat a disorder selected from the group consisting of alopecia areata, ankylosing spondylitis, antiphospholipid syndrome, Addison's disease, autoimmune hemolytic anemia (AIHA) (including warm AIHA), hemolytic anemia, autoimmune hepatitis, hepatitis, Behcets disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, membranous glomerulonephritis, myasthenia gravis, hemolytic disease of the fetus and newborn (HDFN), chronic inflammatory demyelinating polyneuropathy (CIDP), membranous nephropathy, good pasture, polymyositis, Idiopathic thrombocytopenic purpura (ITP; also called "immune thrombocytopenia"), scleroderma, palindromic rheumatism, graves' disease, autoimmune thyroiditis, polyglandular autoimmune syndrome, glomerular nephritis, lupus nephritis, systemic lupus erythematosus (SLE), Type-1 diabetes, and Wegener's granulomatosis.

In some embodiments, the pharmaceutical compositions and methods are useful to reduce or treat an immune response activated by systemic lupus erythematosus, antiphospholipid syndrome, pemphigus vulgaris/bullous pemphigoid, antineutrophil cytoplasmic antibody (ANCA)-associated vasculitis, myasthenia gravis, or neuromyelitis optica.

In some embodiments, the pharmaceutical compositions and methods are useful to decrease the risk of or decrease the risk of developing anemia in the fetus. In some embodiments, the pharmaceutical compositions and methods are useful to decrease or obviate the need for IUT (intrauterine transfusion). In some embodiments, the pharmaceutical compositions and methods are useful to decrease or obviate the need for antenatal PP+IVIg, postnatal transfusion, IVIg, and/or phototherapy.

In some embodiments, the pharmaceutical compositions and methods are useful to reduce or treat an immune response activated by an autoimmune disease. The autoimmune disease may be selected from the group consisting of alopecia areata, ankylosing spondylitis, antiphospholipid syndrome (e.g., antiphospholipid antibody syndrome), Addison's disease, hemolytic anemia (e.g., warm autoimmune hemolytic anemia), autoimmune hepatitis, hepatitis, Behcets disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, epidermolysis bullosa; fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, membranous nephropathy, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, and Wegener's granulomatosis. In some embodiments, the pharmaceutical compositions and methods are useful to reduce or treat an immune response in a fetus or neonate. In some embodiments, the pharmaceutical compositions and methods are useful to reduce or treat an immune response in a fetus or neonate activated by an autoimmune disease in the pregnant mother.

In some embodiments, the pharmaceutical compositions and methods are useful to reduce or treat an immune response activated by systemic lupus erythematosus, antiphospholipid syndrome, pemphigus vulgaris/bullous pemphigoid, antineutrophil cytoplasmic antibody (ANCA)-associated vasculitis, myasthenia gravis, or neuromyelitis optica. In some embodiments, the pharmaceutical compositions and methods are useful to reduce or treat an immune response in a fetus or neonate. In some embodiments, the pharmaceutical compositions and methods are useful to reduce or treat an immune response activated by systemic lupus erythematosus, antiphospholipid syndrome, pemphigus vulgaris/bullous pemphigoid, antineutrophil cytoplasmic antibody (ANCA)-associated vasculitis, myasthenia gravis, or neuromyelitis optica in the pregnant mother.

The pharmaceutical compositions and methods are useful in methods of decreasing pathogenic antibody transport (e.g., pathogenic maternal IgG antibody transport) across the placenta of a pregnant subject, increasing pathogenic antibody catabolism in a pregnant subject, and treating an antibody-mediated enhancement of viral disease in a fetus or a neonate by administering to a pregnant subject an isolated antibody that binds to human FcRn. Diseases and disorders that may benefit from FcRn inhibition by the isolated anti-FcRn antibodies described herein include diseases and disorders in a fetus and/or neonate that are caused by the transfer of maternal pathogenic antibodies (e.g., maternal pathogenic IgG antibodies) across the placenta from a pregnant subject to the fetus and/or neonate.

In some embodiments, the diseases and disorders that may benefit from FcRn inhibition by the isolated anti-FcRn antibodies described herein are fetal and neonatal alloimmune and/or autoimmune disorders. Fetal and neonatal alloimmune disorders are disorders in a fetus and/or neonate that is caused by pathogenic antibodies in the pregnant subject. The pathogenic antibodies in the pregnant subject may attack the antigens of the fetus (e.g., antigens the fetus inherited from the fetus' father), causing the fetus or the neonate to have a fetal and neonatal alloimmune and/or autoimmune disorder.

In some embodiments of all aspects, an antibody associated with an immune disease is detected in a biological sample obtained from the pregnant subject. In some embodiments of all aspects, the biological sample is a blood or urine sample. In some embodiments of all aspects, the biological sample is a blood sample.

In some embodiments, the disclosure features a method for treating or reducing the risk of developing a fetal and neonatal alloimmune and/or autoimmune disorder, the method including: IV administration to a pregnant woman of a composition comprising an antibody comprising a light chain having the amino acid sequence of SEQ ID NO:1 and a heavy chain having the amino acid sequence of SEQ ID NO:2 (antibody referred to as M281), wherein the administration of M281 ceases after week 34 gestational age.

In some embodiments, the disclosure features a method for treating or reducing the risk of developing a fetal and neonatal alloimmune and/or autoimmune disorder comprising administering to a pregnant woman a composition comprising an antibody comprising a light chain having the amino acid sequence of SEQ ID NO:1 and a heavy chain having the amino acid sequence of SEQ ID NO:2 (antibody referred to as M281), wherein the administration of M281 ceases at least one week prior to birth.

Examples of fetal and neonatal alloimmune and/or autoimmune disorders that may be treated by the methods described herein include, but are not limited to, fetal and neonatal alloimmune thrombocytopenia (FNAIT), hemolytic disease of the fetus and newborn (HDFN), alloimmune pan-thrombocytopenia, congenital heart block, fetal arthrogryposis, neonatal myasthenia gravis, neonatal autoimmune hemolytic anemia, neonatal anti-phospholipid syndrome, neonatal polymyositis, dermatomyositis, neonatal lupus, neonatal scleroderma. Behcet's disease, neonatal Graves' disease, neonatal Kawasaki disease, neonatal autoimmune thyroid disease, and neonatal type I diabetes mellitus. In some embodiments of all aspects, the fetal and neonatal autoimmune and/or autoimmune disorder is hemolytic disease of the fetus and newborn. In some embodiments of all aspects, the fetal and neonatal autoimmune and/or autoimmune disorder is fetal and neonatal alloimmune thrombocytopenia. In some embodiments of all aspects, the fetal and neonatal autoimmune and/or autoimmune disorder is congenital heart block. In some embodiments, treatment reduces the risk of a miscarriage. In some embodiments of all aspects, the subject has a history of having had a previous fetal and neonatal alloimmune and/or autoimmune disorder. For example, in some embodiments, the pregnant subject has had a previous pregnancy wherein the fetus or neonate had a fetal and neonatal alloimmune and/or autoimmune disorder. In some embodiments of all aspects, the subject is at risk of having a fetal and neonatal alloimmune and/or autoimmune disorder.

In some embodiments, the diseases and disorders that may benefit from FcRn inhibition by the isolated anti-FcRn antibodies described herein (are viral diseases wherein antibodies facilitate viral entry into host cells, leading to increased or enhanced infectivity in the cells, e.g., antibody-mediated enhancement of viral disease. In some embodiments, an antibody may bind to a viral surface protein and the antibody/virus complex may bind to an FcRn on a cell surface through interaction between the antibody and the receptor. Subsequently, the antibody/virus complex may get internalized into the cell. For example, a virus may gain entry into the cells and/or tissues of a fetus through forming a complex with a maternal IgG antibody. A maternal IgG antibody may bind to a viral surface protein and the IgG/virus complex may bind to an FcRn in the syncytiotrophoblasts of the placenta, which then transfers the complex into the fetus.

In some embodiments, the methods described herein may be used to treat an antibody-mediated enhancement of viral disease. In some embodiments, the viral diseases that are enhanced by pathogenic antibodies (e.g., pathogenic IgG antibodies) include, but are not limited to, viral diseases caused by an alpha virus infection, flavivirus infection, Zika virus infection, Chikungunya virus infection, Ross River virus infection, severe acute respiratory syndrome coronavirus infection, Middle East respiratory syndrome, avian influenza infection, influenza virus infection, human respiratory syncytial virus infection, Ebola virus infection, yellow fever virus infection, dengue virus infection, human immunodeficiency virus infection, respiratory syncytial virus infection, Hantavirus infection, Getah virus infection, Sindbis virus infection, Bunyamwera virus infection, West Nile virus infection, Japanese encephalitis virus B infection, rabbitpox virus infection, lactate dehydrogenase elevating virus infection, reovirus infection, rabies virus infection, foot-and-mouth disease virus infection, porcine reproductive and respiratory syndrome virus infection, simian hemorrhagic fever virus infection, equine infectious anemia virus infection, caprine arthritis virus infection, African swine fever virus infection, lentivirus infection, BK papovavirus infection, Murray Valley encephalitis virus infection, enterovirus infection, cytomegalovirus infection, pneumovirus infection, morbillivirus infection, and measles virus infection.

In some embodiments of all aspects, the viral disease is caused by a virus selected from the group consisting of an alpha virus infection, flavivirus infection, Zika virus infection, Chikungunya virus infection, Ross River virus infection, severe acute respiratory syndrome coronavirus infection, Middle East respiratory syndrome, avian influenza infection, influenza virus infection, human respiratory syncytial virus infection, Ebola virus infection, yellow fever virus infection, dengue virus infection, human immunodeficiency virus infection, respiratory syncytial virus infection, Hantavirus infection, Getah virus infection, Sindbis virus infection, Bunyamwera virus infection, West Nile virus infection, Japanese encephalitis virus B infection, rabbitpox virus infection, lactate dehydrogenase elevating virus infection, reovirus infection, rabies virus infection, foot-and-mouth disease virus infection, porcine reproductive and respiratory syndrome virus infection, simian hemorrhagic fever virus infection, equine infectious anemia virus infection, caprine arthritis virus infection, African swine fever virus infection, lentivirus infection, BK papovavirus infection, Murray Valley encephalitis virus infection, enterovirus infection, cytomegalovirus infection, pneumovirus infection, morbillivirus infection, and measles virus infection.

The blockade of human FcRn by anti-FcRn antibodies may be of therapeutic benefit in diseases that are driven by pathogenic antibodies (e.g., pathogenic IgG antibodies). The ability of FcRn blockade to induce overall pathogenic antibody catabolism and removal of multiple species of pathogenic antibodies, small circulating metabolites, or lipoproteins offers a method to expand the utility and accessibility of a pathogenic antibody removal strategy to patients with pathogenic antibody-driven autoimmune disease pathology. While not bound by theory, the dominant mechanism of action of an anti-FcRn antibody may be to increase the catabolism of pathogenic antibodies in circulation and decrease pathogenic antibody and immune complex deposition in affected tissues.

The anti-FcRn antibodies described herein may be administered to a pregnant subject who has or is at risk of having a medical condition that activates an immune response in the pregnant subject. In some embodiments, the pregnant subject may have had, in the past, a medical condition that activated an immune response in the pregnant subject. In some embodiments, the pregnant subject has a history of having had a previous fetus or neonate that had a fetal and neonatal alloimmune and/or autoimmune disorder. In some embodiments, the anti-FcRn antibodies described herein may be administered to a pregnant subject if a pathogenic antibody associated with an immune disease is detected in a biological sample (e.g., a blood or urine sample) obtained from the pregnant subject. In some embodiments, the pathogenic antibody detected in the biological sample of the pregnant subject is known to bind to an antigen from the fetus in the pregnant subject (e.g., an antigen that the fetus inherited from the fetus' father).

In some embodiments, the anti-FcRn antibodies described herein may be administered to a subject who is planning to become pregnant and who has or is at risk of having a medical condition that activates an immune response in the pregnant subject, and/or who has had, in the past, a medical condition that activated an immune response in the pregnant subject. In some embodiments, a subject is planning to become pregnant and has a history of having had a previous fetus or neonate that had a fetal and neonatal alloimmune and/or autoimmune disorder. In some embodiments, the anti-FcRn antibodies described herein may be administered to a subject who is planning to become pregnant and whose biological sample contains a pathogenic antibody associated with an immune disease.

In some embodiments, the anti-FcRn antibodies described herein may be administered to a subject (e.g., a pregnant subject) to reduce or treat an immune complex-based activation of an acute or chronic immune response in the subject. The acute immune response may be activated by a medical condition (e.g., pemphigus vulgaris, lupus nephritis, myasthenia gravis, Guillain-Barre syndrome, antibody-mediated rejection, catastrophic anti-phospholipid antibody syndrome, immune complex-mediated vasculitis, glomerulitis, a channelopathy, neuromyelitis optica, autoimmune hearing loss, idiopathic thrombocytopenia purpura, autoimmune haemolytic anaemia, immune neutropenia, dilated cardiomyopathy, serum sickness, chronic inflammatory demyelinating polyneuropathy, systemic lupus, reactive arthropathies, primary biliary cirrhosis, ulcerative colitis, or antineutrophil cytoplasmic antibody (ANCA)-associated vasculitis).

In some embodiments, the anti-FcRn antibodies described herein may be administered to a subject (e.g., a pregnant subject) to reduce or treat an immune response activated by an autoimmune disease. The autoimmune disease may be, for example, alopecia areata, ankylosing spondylitis, antiphospholipid syndrome, Addison's disease, hemolytic anemia, warm autoimmune hemolytic anemia (wAIHA), anti-factor antibodies, heparin induced thrombocytopenia (HICT), sensitized transplant, autoimmune hepatitis, hepatitis, Behcet's disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, or Wegener's granulomatosis.

In some embodiments, the subject is a pregnant woman. In certain embodiments, the maintenance dose is based on the weight of the pregnant woman at the time of the first loading dosing and is not adjusted upward based on weight gain by the pregnant woman. In certain embodiments, the maintenance dose is determined per administration and is based on the weight of the pregnant woman at the time of dosing and may be an adjustment upward based on weight gain by the pregnant woman. In certain embodiments, the maintenance dose is administered at least every other week; the maintenance dose is administered every other week; the maintenance dose is administered at least every week; the maintenance dose is administered every week. In certain embodiments, the subject is a pregnant woman and the first loading dose is administered during the first trimester of pregnancy; the subject is a pregnant woman and the first loading dose is administered during the second trimester of pregnancy; the subject is a pregnant woman and the first loading dose is administered during the third trimester of pregnancy. In certain embodiments, the subject is a pregnant woman and the pregnant woman has an obstetrical history of severe fetal anemia; the subject is a pregnant woman and the pregnant woman has an obstetrical history of hemolytic disease of the fetus and newborn; the subject is a pregnant woman and the pregnant woman has an elevated anti RhD, anti-Rhc or anti Kell immunoglobulin alloantibody titer; the subject is a pregnant woman and the pregnant woman has an elevated anti-Rhc or anti-Kell immunoglobulin alloantibody titer; the subject is a pregnant woman and the pregnant woman has an elevated immunoglobulin alloantibody titer for one or more antibodies selected from the group consisting of anti-Lua, Lub, Bg, Kna, Yta, E. c. K. Cw, Fya, cE, ce, D, Ce, cE, K, Kpa, Kpb, Fya, M, N, S, Lea, Leb, Fy, Jka. Diego, P and Mia/Mur; the subject is a pregnant woman and the pregnant woman has an obstetrical history of severe fetal anemia or stillbirth at ≤24 weeks gestation and elevated anti-D or anti-Kell IgG alloantibody titers and is pregnant with an antigen-positive fetus; the subject is a pregnant woman and the first dosing is weeks 12 to 16 of pregnancy; and the subject is a pregnant woman and the first dosing is during week 14 of pregnancy.

In some embodiments, methods of treating myasthenia gravis in a patient are provided. In some embodiments, the myasthenia gravis is generalized myasthenia gravis. In some embodiments, the patient is an adult patient or a pediatric patient. In some embodiments, the method comprise administering a pharmaceutical composition comprising an anti-FcRn antibody to the subject.

In some embodiments, methods of treating myasthenia gravis in a patient in need thereof, the method comprising administering an initial loading dose of about 30 mg/kg mg/kg to about 60 mg/kg of an anti-FcRn antibody followed by administering a maintenance dose of about 15 mg/kg to about 30 mg/kg of the anti-FcRn antibody, wherein the anti-FcRn antibody comprises a heavy chain comprising a HCDR1 of SEQ ID NO: 6, a HCDR2 of SEQ ID NO: 7, and a HCDR3 of SEQ ID NO: 8; and a light chain comprising a LCDR1 of SEQ ID NO: 3, a LCDR2 of SEQ ID NO: 4, and a LCDR3 of SEQ ID NO: 5; wherein the administration reduces serum IgG in the patient by at least 10%, at least 20%, at least 30%, at least 40%, at least 50%, at least 60%, at least 70%, at least 80%, or at least 90% of baseline serum IgG are provided.

In some embodiments, methods of treating myasthenia gravis in a patient in need thereof, the method comprising administering an initial loading dose of about 30 mg/kg mg/kg to about 60 mg/kg of an anti-FcRn antibody followed by administering a maintenance dose of about 15 mg/kg to about 30 mg/kg of the anti-FcRn antibody, wherein the anti-FcRn antibody comprises a heavy chain comprising a HCDR1 of SEQ ID NO: 6, a HCDR2 of SEQ ID NO: 7, and a HCDR3 of SEQ ID NO: 8; and a light chain comprising a LCDR1 of SEQ ID NO: 3, a LCDR2 of SEQ ID NO: 4, and a LCDR3 of SEQ ID NO: 5; wherein the administration reduces serum autoantibodies by at least 95%, at least 90%, at least 85%, at least 80%, at least 75%, at least 50%, or at least 25% of baseline serum autoantibodies are provided.

In some embodiments, methods of treating or reducing severity of myasthenia gravis in a subject, the method comprising administering to the subject an initial loading dose of about 5 mg/kg mg/kg to about 120 mg/kg of an anti-FcRn antibody followed by administering a maintenance dose of about 5 mg/kg to about 60 mg/kg of an anti-FcRn antibody, wherein the anti-FcRn antibody comprises a heavy chain comprising a HCDR1 of SEQ ID NO: 6, a HCDR2 of SEQ ID NO: 7, and a HCDR3 of SEQ ID NO: 8; and a light chain comprising a LCDR1 of SEQ ID NO: 3, a LCDR2 of SEQ ID NO: 4, and a LCDR3 of SEQ ID NO: 5, are provided.

In some embodiments, the anti-FcRn antibody is as provided herein. In some embodiments, the anti-FcRn antibody is nipocalimab, RVT-1401 (HL161), rozanolixizumab (UCB7665), ALXN1830, ABY-039, or efgartigimod. RVT-1401 (also referred to as HL161BKN) is described in WO2020097099, rozanolixizumab is described in WO2014019727, and efgartigimod (ARGX-113) is described in WO2015100299, each of which is hereby incorporated by reference in its entirety. In some embodiments, the anti-FcRN antibody is a biosimilar of any of anti-FcRN antibodies provided for herein. In preferred embodiments, the anti-FcRn antibody is nipocalimab.

In some embodiments, the anti-FcRn antibody comprising a heavy chain and a light chain, wherein the heavy chain comprises a HCDR1 of SEQ ID NO: 6, a HCDR2 of SEQ ID NO: 7, and a HCDR3 of SEQ ID NO: 8; and wherein the light chain comprises a LCDR1 of SEQ ID NO: 3, a LCDR2 of SEQ ID NO: 4, and a LCDR3 of SEQ ID NO: 5. In some embodiments, the heavy chain comprises a variable region heavy chain comprising an amino acid sequence having at least 90% identity to the sequence of SEQ ID NO: 10 and the light chain comprises a variable region light chain comprising an amino acid sequence having at least 90% identity to the sequence of SEQ ID NO: 9. In some embodiments, the heavy chain comprises a variable region heavy chain comprising an amino acid sequence having at least 95% identity to the sequence of SEQ ID NO: 10 and the light chain comprises a variable region light chain comprising an amino acid sequence having at least 95% identity to the sequence of SEQ ID NO: 9. In some embodiments, the heavy chain comprises a variable region heavy chain comprising an amino acid sequence having at least 99% identity to the sequence of SEQ ID NO: 10 and the light chain comprises a variable region light chain comprising an amino acid sequence having at least 99% identity to the sequence of SEQ ID NO: 9. In some embodiments, the heavy chain comprises an amino acid sequence having at least 90% identity to the sequence of SEQ ID NO: 2 and the light chain comprises an amino acid sequence having at least 90% identity to the sequence of SEQ ID NO: 1. In some embodiments, the heavy chain comprises an amino acid sequence having at least 95% identity to the sequence of SEQ ID NO: 2 and the light chain comprises an amino acid sequence having at least 95% identity to the sequence of SEQ ID NO: 1. In some embodiments, the heavy chain comprises an amino acid sequence having at least 99% identity to the sequence of SEQ ID NO: 2 and the light chain comprises an amino acid sequence having at least 99% identity to the sequence of SEQ ID NO: 1. In some embodiments, the heavy chain comprises a variable region heavy chain comprising the amino acid sequence of SEQ ID NO: 10 and the light chain comprises a variable region light chain comprising the amino acid sequence of SEQ ID NO: 9. In some embodiments, the heavy chain comprises the amino acid sequence of SEQ ID NO: 2 and the light chain comprises the amino acid sequence of SEQ ID NO: 1.

In some embodiments, methods of treating myasthenia gravis in a subject comprise administering a pharmaceutical composition comprising about 10 mg/ml to about 60 mg/ml of an anti-FcRn antibody, about 20 mM to about 30 mM sodium phosphate, about 20 mM to about 30 mM sodium chloride, about 80 mg/ml to about 100 mg/ml Trehalose, and about 0.1% w/v to about 0.005% w/v Polysorbate 80.

In some embodiments, method of treating myasthenia gravis in a subject comprise administering the initial dose and the maintenance dose of an anti-FcRn antibody. In some embodiments, the initial loading dose is about 60 mg/kg. In some embodiments, the initial loading dose is about 30 mg/kg. In some embodiments, the maintenance dose is about 15 mg/kg, about 30 mg/kg, about 45 mg/kg, or about 60 mg/kg. In some embodiments, the maintenance dose is about 15 mg/kg. In some embodiments, the maintenance dose is about 30 mg/kg. In some embodiments, the maintenance dose is 45 mg/kg. In some embodiments, the administering of the maintenance dose occurs 1 week, 2 weeks, 3 weeks, or 4 weeks after the administration of the initial loading dose. In some embodiments, the administering of the maintenance dose occurs 1 week, 2 weeks, 3 weeks, or 4 weeks after the administration of the preceding maintenance dose. In some embodiments, the initial loading dose is infused into the subject in about 30 minutes to about 90 minutes. In some embodiments, the maintenance dose is infused into the subject in about 15 to about 60 minutes.

In some embodiments, the subject being treated for myasthenia gravis has or shows a reduction in one or more immunoglobulin isotypes or total IgG. In some embodiments, the subject being treated for myasthenia gravis, or moderate to severe active myasthenia gravis has or shows a reduction in one or more immunoglobulin isotypes or total IgG. In some embodiments, the reduction is about 1%, 2%, 3%, 4%, 5%, 6%, 7%, 8%, 9%, 10%, 1-20%, 5-20%, 5-25%, 10-30%, 15-35%, 20-40%, 40-60%, or, about, or at least, 5%, 10%, 15%, 20%, 25%, 30%, 35%, 40%, 45%, 50%, 60%, 70%, 80%, or 90%. In some embodiments, the administration of the anti-FcRn antibody reduces serum IgG by at least 10%, at least 20%, at least 30%, at least 40%, at least 50%, at least 60%, at least 70%, at least 80%, or at least 90% of baseline serum IgG. In some embodiments, the administration of the anti-FcRn antibody reduced serum IgG in the patient by at least 90% of baseline. In some embodiments, the administration of the anti-FcRn antibody reduces serum IgG in the patient by at least 80% of baseline. In some embodiments, the administration of the anti-FcRn antibody reduces serum IgG in the patient by at least 70% of baseline. In some embodiments, the isotype of immunoglobulins reduced is IgG1, IgG2, IgG3, IgG4, or any combination thereof. In some embodiments, the administration of the anti-FcRn antibody reduces serum IgG1 by at least 10%, at least 20%, at least 30%, at least 40%, at least 50%, at least 60%, at least 70%, at least 80%, or at least 90% of baseline serum IgG1. In some embodiments, the administration of the anti-FcRn antibody reduced serum IgG1 in the patient by at least 90% of baseline. In some embodiments, the administration of the anti-FcRn antibody reduces serum IgG1 in the patient by at least 80% of baseline. In some embodiments, the administration of the anti-FcRn antibody reduces serum IgG1 in the patient by at least 70% of baseline. In some embodiments, the administration of the anti-FcRn antibody reduces serum IgG2 by at least 10%, at least 20%, at least 30%, at least 40%, at least 50%, at least 60%, at least 70%, at least 80%, or at least 90% of baseline serum IgG2. In some embodiments, the administration of the anti-FcRn antibody reduced serum IgG2 in the patient by at least 90% of baseline. In some embodiments, the administration of the anti-FcRn antibody reduces serum IgG2 in the patient by at least 80% of baseline. In some embodiments, the administration of the anti-FcRn antibody reduces serum IgG2 in the patient by at least 70% of baseline. In some embodiments, the administration of the anti-FcRn antibody reduces serum IgG3 by at least 10%, at least 20%, at least 30%, at least 40%, at least 50%, at least 60%, at least 70%, at least 80%, or at least 90% of baseline serum IgG3. In some embodiments, the administration of the anti-FcRn antibody reduces serum IgG3 in the patient by at least 90% of baseline. In some embodiments, the administration of the anti-FcRn antibody reduces serum IgG3 in the patient by at least 80% of baseline. In some embodiments, the administration of the anti-FcRn antibody reduces serum IgG3 in the patient by at least 70% of baseline. In some embodiments, the administration of the anti-FcRn antibody reduces serum IgG4 by at least 10%, at least 20%, at least 30%, at least 40%, at least 50%, at least 60%, at least 70%, at least 80%, or at least 90% of baseline serum IgG4. In some embodiments, the administration of the anti-FcRn antibody reduced serum IgG4 in the patient by at least 90% of baseline. In some embodiments, the administration of the anti-FcRn antibody reduces serum IgG4 in the patient by at least 80% of baseline. In some embodiments, the administration of the anti-FcRn antibody reduces serum IgG4 in the patient by at least 70% of baseline.

In some embodiments, the administration of the anti-FcRn antibody reduces serum albumin by at most 18%, at most 16%, at most 14%, at most 12%, at most 10%, at most 8%, at most 6%, at most 4%, or at most 2% of baseline of serum albumin. In some embodiments, the administration of the anti-FcRn antibody reduces serum albumin by at most 18% of baseline of serum albumin. In some embodiments, the administration of the anti-FcRn antibody reduces serum albumin by at most 16% of baseline of serum albumin. In some embodiments, the administration of the anti-FcRn antibody reduces serum albumin by at most 14% of baseline of serum albumin. In some embodiments, the administration of the anti-FcRn antibody reduces serum albumin by at most 12% of baseline of serum albumin. In some embodiments, the administration of the anti-FcRn antibody reduces serum albumin by at most 10% of baseline of serum albumin. In some embodiments, the administration of the anti-FcRn antibody reduces serum albumin by at most 8% of baseline of serum albumin. In some embodiments, the administration of the anti-FcRn antibody reduces serum albumin by at most 6% of baseline of serum albumin. In some embodiments, the administration of the anti-FcRn antibody reduces serum albumin by at most 4% of baseline of serum albumin. In some embodiments, the administration of the anti-FcRn antibody reduces serum albumin by at most 2% of baseline of serum albumin.

In some embodiments, the subject being treated for myasthenia gravis has or shows a reduction in autoantibodies. In some embodiments, the reduction is about 1%, 2%, 3%, 4%, 5%, 6%, 7%, 8%, 9%, 10%, 1-20%, 5-20%, 5-25%, 10-30%, 15-35%, 20-40%, 40-60%, or, about, or at least, 5%, 10%, 15%, 20%, 25%, 30%, 35%, 40%, 45%, 50%, 60%, 70%, 80%, 90%, or 95%. In some embodiments, the autoantibodies reduced are selected from the group consisting of: anti-acetylcholine receptors (AChRs), anti-muscle-specific kinase (MuSK) anti-low-density lipoprotein receptor-related protein 4 (LRP4), anti-agrin, anti-titin, anti-Kv1.4, anti-ryanodine receptors, anti-collagen Q, and anti-cortactin. In some embodiments, the autoantibodies are anti-AChR or an anti-MuSK antibodies. In some embodiments, the administration of the anti-FcRn antibody reduces anti-AChR antibodies by at least 95%, at least 90%, at least 85%, at least 80%, at least 75%, at least 50%, or at least 25% of baseline anti-AChR antibodies. In some embodiments, the administration of the anti-FcRn antibody reduces anti-AChR antibodies by at least 95% of baseline anti-AChR antibodies. In some embodiments, the administration of the anti-FcRn antibody reduces anti-AChR antibodies by at least 90% of baseline anti-AChR antibodies. In some embodiments, the administration of the anti-FcRn antibody reduces anti-AChR antibodies by at least 85% of baseline anti-AChR antibodies. In some embodiments, the administration of the anti-FcRn antibody reduces anti-AChR antibodies by at least 80% of baseline anti-AChR antibodies. In some embodiments, the administration of the anti-FcRn antibody reduces anti-AChR antibodies by at least 75% of baseline anti-AChR antibodies. In some embodiments, the administration of the anti-FcRn antibody reduces anti-AChR antibodies by at least 50% of baseline anti-AChR antibodies. In some embodiments, the administration of the anti-FcRn antibody reduces anti-AChR antibodies by at least 25% of baseline anti-AChR antibodies. In some embodiments, the administration of the anti-FcRn antibody reduces anti-MuSK antibodies by at least 95%, at least 90%, at least 85%, at least 80%, at least 75%, at least 50%, or at least 25% of baseline anti-MuSK antibodies. In some embodiments, the administration of the anti-FcRn antibody reduces anti-MuSK antibodies by at least 95% of baseline anti-MuSK antibodies. In some embodiments, the administration of the anti-FcRn antibody reduces anti-MuSK antibodies by at least 90% of baseline anti-MuSK antibodies. In some embodiments, the administration of the anti-FcRn antibody reduces anti-MuSK antibodies by at least 85% of baseline anti-MuSK antibodies. In some embodiments, the administration of the anti-FcRn antibody reduces anti-MuSK antibodies by at least 80% of baseline anti-MuSK antibodies. In some embodiments, the administration of the anti-FcRn antibody reduces anti-MuSK antibodies by at least 75% of baseline anti-MuSK antibodies. In some embodiments, the administration of the anti-FcRn antibody reduces anti-MuSK antibodies by at least 50% of baseline anti-MuSK antibodies. In some embodiments, the administration of the anti-FcRn antibody reduces anti-MuSK antibodies by at least 25% of baseline anti-MuSK antibodies. In some embodiments, the administration of the anti-FcRn antibody reduces anti-AChR antibodies by at least 95%, at least 90%, at least 85%, at least 80%, at least 75%, at least 50%, or at least 25% of baseline anti-AChR antibodies; and anti-MuSK antibodies by at least 95%, at least 90%, at least 85%, at least 80%, at least 75%, at least 50%, or at least 25% of baseline anti-MuSK antibodies.

In some embodiments, the method comprise administering a pharmaceutical composition comprising administering an anti-FcRn antibody to the subject. In some embodiments, the anti-FcRn antibody is nipocalimab, RVT-1401 (HL161), rozanolixizumab (UCB7665), ALXN1830, ABY-039, or efgartigimod. In some embodiments, the anti-FcRn antibody is as provided for herein. In some embodiments, the subject has or is suspected of having myasthenia gravis. In preferred embodiments, the anti-FcRn antibody is nipocalimab.

In some embodiments, administration of the anti-FcRN antibody to a subject with myasthenia gravis treats or ameliorates ocular myasthenia, ptosis, difficulty chewing, dysphagia, dysarthria, hypophonia, dyspnea, an inability to hold the mouth closed, an appearance of sadness or sleepiness, difficulty holding the head upright, diplopia, dysarthria, difficulty swallowing, change in facial expression, shortness of breath, weakness in arms, weakness in hands, weakness in fingers, weakness in legs, weakness in neck.

In some embodiments, the subject treated for myasthenia gravis shows an improvement in one or more of the following assays, scores, or criteria, which can be used to evaluate the improvement or condition of a subject with myasthenia gravis. In some embodiments, the subject shows improvement in one or more of the following: MG-ADL score, QMG score, MG-QoL15r score, Neuro-QoL-Fatigue score, EQ-5D-5L score, MGFA scale, PGI-C score, PGI-S score, C-SSRS score, and PedsQL score.

In some embodiments, treatment of MG includes the improvement of a clinical marker for MG progression. These markers include MG activity of daily living profile (MG-ADL), and quantitative Myasthenia Gravis (QMG) score for disease severity. In certain embodiments, MG-ADL is the primary score for measuring improvement of MG.

The MG-ADL is an 8-point questionnaire that focuses on relevant symptoms and functional performance of activities of daily living (ADL) in MG subjects. The 8 items of the MG-ADL are derived from symptom-based components of the original 13-item QMG to assess disability secondary to ocular (2 items), bulbar (3 items), respiratory (1 item), and gross motor or limb (2 items) impairment related to effects from MG. In this functional status instrument, each response is graded 0 (normal) to 3 (most severe). The range of total MG-ADL score is 0-24. A clinically meaningful improvement in a patient's MG-ADL would be a 2 point or greater reduction in score after 57 days of treatment.

In some embodiments, the patient being treated by the methods provided herein experiences a change from baseline in Myasthenia Gravis Activities of Daily Living (MG-ADL) score over time or after 57 days of treatment. In some embodiments, the change from baseline of MG-ADL score is greater than or equal to 2 points on the MG-ADL scale.

The current QMG scoring system consists of 13 items: ocular (2 items), facial (1 item), bulbar (2 items), gross motor (6 items), axial (1 item), and respiratory (1 item); each graded 0 to 3, with 3 being the most severe. The range of total QMG score is 0-39. The QMG scoring system is considered to be an objective evaluation of therapy for MG and is based on quantitative testing of sentinel muscle groups. Higher scores indicated greater weakness. The QMG was administered by a trained qualified healthcare professional (e.g., physician, physician assistant, nurse practitioner, nurse). The QMG was to be administered by the same healthcare professional for a given subject throughout the study, if possible, and was to be performed at approximately the same time of day throughout the study.

In some embodiments, the patient being treated by the methods provided herein experiences a change from baseline in Myasthenia Gravis Activities of Daily Living (MG-ADL) score over time or after 22, 23, and 24 weeks of treatment. In some embodiments, the change from baseline of MG-ADL score is greater than or equal to 2 points on the MG-ADL scale.

In some embodiments, the patient being treated by the methods provided herein experiences a change from baseline in QMG score after 57 days of treatment. In some embodiments, the patient being treated by the methods provided herein experiences a change from baseline in QMG score over time after administration of the last dose. In some embodiments, the change from baseline is at least a 2, 3, 4, 5, 6, 7, or greater than or equal to 8 point reduction in the patient's QMG score over time after administration of the last dose. In some embodiments, the change from baseline is at least a 2 point reduction in the patient's QMG score over time after administration of the last dose. In some embodiments, the change from baseline is at least a 3 point reduction in the patient's QMG score over time after administration of the last dose. In some embodiments, the change from baseline is at least a 4 point reduction in the patient's QMG score over time after administration of the last dose. In a some embodiments, the change from baseline is at least a 5 point reduction in the patient's QMG score over time after administration of the last dose. In some embodiments, the change from baseline is at least a 6 point reduction in the patient's QMG score over time after administration of the last dose. In some embodiments, the change from baseline is at least a 7 point reduction in the patient's QMG score over time after administration of the last dose. In some embodiments, the change from baseline is greater than or equal to 8 point reduction in the patient's QMG score over time after administration of the last dose. In some embodiments, the patient being treated by the methods provided herein experiences a change from baseline in QMG score after 22, 23, and 24 weeks of treatment. In some embodiments, the patient being treated by the methods provided herein experiences a change from baseline in QMG score over time after administration of the last dose. In some embodiments, the change from baseline is at least a 2, 3, 4, 5, 6, 7, or greater than or equal to 8 point reduction in the patient's QMG score after 22, 23, and 24 weeks of treatment or over time after administration of the last dose. In some embodiments, the change from baseline is at least a 2 point reduction in the patient's QMG score after 22, 23, and 24 weeks of treatment or over time after administration of the last dose. In some embodiments, the change from baseline is at least a 3 point reduction in the patient's QMG score after 22, 23, and 24 weeks of treatment or over time after administration of the last dose. In some embodiments, the change from baseline is at least a 4 point reduction in the patient's QMG score after 22, 23, and 24 weeks of treatment or over time after administration of the last dose. In some embodiments, the change from baseline is at least a 5 point reduction in the patient's QMG score after 22, 23, and 24 weeks of treatment or over time after administration of the last dose. In some embodiments, the change from baseline is at least a 6 point reduction in the patient's QMG score after 22, 23, and 24 weeks of treatment or over time after administration of the last dose. In some embodiments, the change from baseline is at least a 7 point reduction in the patient's QMG score after 22, 23, and 24 weeks of treatment or over time after administration of the last dose. In some embodiments, the change from baseline is greater than or equal to 8 point reduction in the patient's QMG score after 22, 23, and 24 weeks of treatment or over time after administration of the last dose.

The 15-item Myasthenia Gravis Qualify of Life scale (MG-QoL-15r) is a health-related quality of life evaluative instrument specific to subjects with MG. See Table 4. MG-QoL-15r was designed to provide information about subjects' perception of impairment and disability and the degree to which disease manifestations are tolerated and to be easy to administer and interpret. The MG-QoL-15r is completed by the subject. Total scores range from 0 to 60 and higher scores indicate greater extent of and dissatisfaction with MG-related dysfunction. The MG-QoL-15r was used to assess the subject's limitations related to living with MG. Each of the 15 items were rated by the subject on a 3-point scale based on a recall period of "over the past few weeks", with a maximum score of 30. Higher scores indicated more limitation.

In some embodiments, the patient being treated by the methods provided herein experiences a change from baseline in MG-QoL-15r score after 57 days of treatment. In some embodiments, the patient being treated by the methods provided herein experiences a change from baseline in MG-QoL-15r score over time after administration of the last dose. In some embodiments, the patient being treated by the methods provided herein experiences a change from baseline in MG-QoL-15r score after 22, 23, and 24 weeks of treatment. In some embodiments, the patient being treated by the methods provided herein experiences a change from baseline in MG-QoL-15r score over time after administration of the last dose. In some embodiments, the patient achieves a change from baseline on MG-QoL-15r scale that is at least a 3, 4, 5, or 6 point reduction in MG-QoL-15r score. In some embodiments, the patient achieves a change from baseline on MG-QoL-15r scale that is at least a 3 point reduction in MG-QoL-15r score. In some embodiments, the patient achieves a change from baseline on MG-QoL-15r scale that is at least a 6 point reduction in MG-QoL-15r score.

The Myasthenia Gravis Foundation of America Clinical Classification (MGFA) was used to assess the subject's MG severity. The system comprises 5 classes of disease severity ranging from Class I (ocular muscle weakness only) to Class V (the subject is intubated). Classes II through IV are each further divided into 2 subclasses based on which muscle groups are primarily affected. The MGFA was administered by a trained qualified healthcare professional (e.g., physician, physician assistant, nurse practitioner, nurse and was to be assessed by the same person for a given subject throughout the study, if possible.

In some embodiments, the patient being treated by the methods provided herein experiences a shift in MGFA classification after 57 days of treatment. In some embodiments, the patient being treated by the methods provided herein experiences a shift in MGFA classification over time after administration of the last dose. In some embodiments, the shift is about 1%, 2%, 3%, 4%, 5%, 6%, 7%, 8%, 9%, 10%, 1-20%, 5-20%, 5-25%, 10-30%, 15-35%, 20-40%, 40-60%, or, about, or at least, 5%, 10%, 15%, 20%, 25%, 30%, 35%, 40%, 45%, 50%, 60%, 70%, or 80%. In some embodiments, the patient being treated by the methods provided herein experiences a shift in MGFA classification after 22, 23, and 24 weeks of treatment. In some embodiments, the patient being treated by the methods provided herein experiences a shift in MGFA classification over time after administration of the last dose. In some embodiments, the shift is about 1%, 2%, 3%, 4%, 5%, 6%, 7%, 8%, 9%, 10%, 1-20%, 5-20%, 5-25%, 10-30%, 15-35%, 20-40%, 40-60%, or, about, or at least, 5%, 10%, 15%, 20%, 25%, 30%, 35%, 40%, 45%, 50%, 60%, 70%, 80%, 90%, or 95%.

In some embodiments, the patient being treated by the methods provided herein experiences a change on the Quality of Life in Neurological Disorders (Neuro-QoL-Fatigue). Neuro-QoL-Fatigue is a reliable and effective short 19-item fatigue survey that is filled out by the subject on all items. Higher scores indicate greater impact of MG on heavier fatigue and activity. The clinically significant improvement in the patient's Neuro-QoL-Fatigue score is reflected in the decrease in score after 22, 23, and 24 weeks of treatment or over time after administration of the last dose.

In some embodiments, the patient being treated by the methods provided herein experiences a change from baseline on the Neuro-QoL-Fatigue scale after 22, 23, and 24 weeks of treatment. In some embodiments, the patient being treated by the methods provided herein experiences a change from baseline on the Neuro-QoL-Fatigue scale over time after administration of the last dose. In some embodiments, the change from baseline on the Neuro-QoL-Fatigue indicates improvement. In some embodiments, the change is about 1%, 2%, 3%, 4%, 5%, 6%, 7%, 8%, 9%, 10%, 1-20%, 5-20%, 5-25%, 10-30%, 15-35%, 20-40%, 40-60%, or, about, or at least, 5%, 10%, 15%, 20%, 25%, 30%, 35%, 40%, 45%, 50%, 60%, 70%, 80%, 90%, or 95%.

In some embodiments, the patient being treated by the methods provided herein experiences a change on the EuroQol 5-dimension 5-level quality of life questionnaire (5Q-5D-5L). The EQ-5D-5L is a standardized measure of health status developed by the EuroQol Group to provide a simple, generic measure of health for clinical and economic appraisal. The EQ-5D-5L, as a measure of health-related quality of life, defines health in terms of 5 dimensions: mobility, self-care, usual activities, pain/discomfort, anxiety/depression. Each dimension has 3 ordinal levels of severity: "no problem" (1), "some problems" (2), "severe problems" (3). Overall health state is defined as a 5-digit number. Health states defined by the 5-dimensional classification can be converted into corresponding index scores that quantify health status, where −0.594 represents "severe problems" and 1 represents "no problem."

In some embodiments, the patient being treated by the methods provided herein experiences a change from baseline on the EQ-5D-5L scale. In some embodiments, the change from baseline on the EQ-5D-5L scale indicates improvement. In some embodiments, the patient being treated by the methods provided herein experiences a change from baseline on EQ-5D-5L scale after 22, 23, and 24 weeks of treatment or over time after administration of the last dose. In some embodiments, the change is about 1%, 2%, 3%, 4%, 5%, 6%, 7%, 8%, 9%, 10%, 1-20%, 5-20%, 5-25%, 10-30%, 15-35%, 20-40%, 40-60%, or, about, or at least, 5%, 10%, 15%, 20%, 25%, 30%, 35%, 40%, 45%, 50%, 60%, 70%, 80%, 90%, or 95%.

In some embodiments, the patient being treated by the methods provided herein experiences a change on the Patient Global Impression of Change scale (PGI-C). The PGI-C is a patient-rated assessment of response to treatment on a 7-point Likert scale and is completed at week 2, week 4, week 8, week 12, week 16, week 20, week 22, and at the end-of-study (week 24).

In some embodiments, the patient being treated by the methods provided herein experiences a change from baseline on the PGI-C scale. In some embodiments, the change from baseline on the PGI-C scale indicates improvement. In some embodiments, the patient being treated by the methods provided herein experiences a change from baseline on PGI-C scale after 22, 23, and 24 weeks of treatment or over time after administration of the last dose. In some embodiments, the change is about 1%, 2%, 3%, 4%, 5%, 6%, 7%, 8%, 9%, 10%, 1-20%, 5-20%, 5-25%, 10-30%, 15-35%, 20-40%, 40-60%, or, about, or at least, 5%, 10%, 15%, 20%, 25%, 30%, 35%, 40%, 45%, 50%, 60%, 70%, 80%, 90%, or 95%.

In some embodiments, the patient being treated by the methods provided herein experiences a change on the Patient Global Impression of Severity scale (PGI-S). The Patient Global Impression of Severity (PGI-S) is a global index that may be used to rate the severity of a specific condition (a single-state scale). It is a simple, direct, easy to use scale that is intuitively understandable to clinicians. The PGI-S is a single question asking the patient to rate how their urinary tract condition is now on a scale of 1 (normal) to 4 (severe).

In some embodiments, the patient being treated by the methods provided herein experiences a change from baseline on the PGI-S scale. In some embodiments, the change from baseline on the PGI-S scale indicates improvement. In some embodiments, the patient being treated by the methods provided herein experiences a change from baseline on PGI-S scale after 22, 23, and 24 weeks of treatment or over time after administration of the last dose. In some embodiments, the change is about 1%, 2%, 3%, 4%, 5%, 6%, 7%, 8%, 9%, 10%, 1-20%, 5-20%, 5-25%, 10-30%, 15-35%, 20-40%, 40-60%, or, about, or at least, 5%, 10%, 15%, 20%, 25%, 30%, 35%, 40%, 45%, 50%, 60%, 70%, 80%, 90%, or 95%.

In some embodiments, the patient being treated by the methods provided herein experiences a change on the Columbia-Suicide Severity Rating Scale. The C-SSRS is used to rate the patient's degree of suicidal ideation on a scale ranging from "no suicidal ideation" to "active suicidal ideation with specific plan and intent". (Posner 2011) The C-SSRS is completed at screening (Visit 0), day 1, week 2, week 4, week 8, week 12, week 16, week 20, and week 24.

In some embodiments, the patient being treated by the methods provided herein experiences a change from baseline on the C-SSRS scale. In some embodiments, the change from baseline on the C-SSRS scale indicates improvement. In some embodiments, the patient being treated by the methods provided herein experiences a change from baseline on C-SSRS scale after 22, 23, and 24 weeks of treatment or over time after administration of the last dose. In some embodiments, the change is about 1%, 2%, 3%, 4%, 5%, 6%, 7%, 8%, 9%, 10%, 1-20%, 5-20%, 5-25%, 10-30%, 15-35%, 20-40%, 40-60%, or, about, or at least, 5%, 10%, 15%, 20%, 25%, 30%, 35%, 40%, 45%, 50%, 60%, 70%, 80%, 90%, or 95%.

In some embodiments, the pediatric patient being treated by the methods provided herein experiences a change on the Pediatric Quality of Life Inventory scale (PedsQL). The PedsQL Measurement Model is a modular approach to measuring health-related quality of life (HRQOL) in healthy children and adolescents and those with acute and chronic health conditions. The PedsQL Measurement Model integrates seamlessly both generic core scales and disease-specific modules into one measurement system. The 23-item PedsQL Generic Core Scales were designed to measure the core dimensions of health as delineated by the World Health Organization, as well as role (school) functioning. The PedsQL can be completed by children and young people, with versions available for children and young people aged 5-7, 8-12, and 13-18. Parent-rated versions are available for children aged 2-4, 5-7, 8-12, and 13-18. The PedsQL inventory takes around five minutes to complete and can be self-administered by parents, children and young people aged 8 to 18 after being introduced by a trained administrator. For younger children and as an alternative in special circumstances, clinicians can administer the inventory as long as instructions and all items are read word-for-word to the child or young person. Items on the PedsQL Generic Core Scales are reverse scored and transformed to a 0-100 scale. Higher scores indicate better health related quality of life: 0 ("Never")=100; 1 ("Almost Never")=75; 2 ("Sometimes")=50; 3 ("Often")=25; and 4 ("Almost Always")=0. Versions used: Teen report acute version for children ages 13-18; Parent report acute version for children ages 8-12; Parent report acute version for young children ages 5-7 and Parent report acute version for toddlers ages 2-4.

In some embodiments, the pediatric patient being treated by the methods provided herein experiences a change from baseline on PedsQL scale. In some embodiments, the change from baseline on PedsQL scale indicates improvement. In some embodiments, the pediatric patient being treated by the methods provided herein experiences a change from baseline on PedsQL scale after 2, 4, 5, 6, 7, 8, 9, 10, 11, 12, 13, 14, 15, 16, 17, 18, 19, 20, 21, 22, and 24 weeks of treatment or over time after administration of the last dose. In some embodiments, the change is about 1%, 2%, 3%, 4%, 5%, 6%, 7%, 8%, 9%, 10%, 1-20%, 5-20%, 5-25%, 10-30%, 15-35%, 20-40%, 40-60%, or, about, or at least, 5%, 10%, 15%, 20%, 25%, 30%, 35%, 40%, 45%, 50%, 60%, 70%, 80%, 90%, or 95%.

In some embodiments, the subject is also treated with an additional therapeutic in addition to an anti-FcRn antibody. In some embodiments, the additional therapeutic is an acetylcholinesterase inhibitor, pyridostigmine, pyridostigmine bromide (Mestinon), neostigmine, prednisone, azathioprine (Imuran), mycophenylate mofetil (CellCept), tacrolimus (Prograf), methotrexate, cyclosporine (Sandimmune, Neoral), and cyclophosphamide (Cytoxan, Neosar), rituximab (Rituxan), eculizumab (Soliris), IVIg, or any combination thereof. In some embodiments, the additional therapeutic is administered concurrently or sequentially (prior to or after) with the anti-FcRn antibody.

As provided for herein, in some embodiments, pharmaceutical compositions comprising an anti-FcRn antibody are provided. In some embodiments, pharmaceutical compositions comprising an anti-FcRn antibody for administration to a patient suffering from myasthenia gravis wherein the anti-FcRn antibody is administered to the patient in a therapeutically effective amount at an initial loading dose of about 30 mg/kg mg/kg to about 60 mg/kg followed by administering a maintenance dose of about 15 mg/kg to about 30 mg/kg of the anti-FcRn antibody, and the anti-FcRn antibody comprises a heavy chain comprising a HCDR1 of SEQ ID NO: 6, a HCDR2 of SEQ ID NO: 7, and a HCDR3 of SEQ ID NO: 8; and a light chain comprising a LCDR1 of SEQ ID NO: 3, a LCDR2 of SEQ ID NO: 4, and a LCDR3 of SEQ ID NO: 5. are provided. In some embodiments, the patient is an adult patient or a pediatric patient.

In some embodiments, the myasthenia gravis is generalized myasthenia gravis. In some embodiments, the subject is a subject with a suboptimal response to a stable therapy for gMG. In some embodiments, the stable therapy for gMG comprises: acetylcholinesterase inhibitors, glucocorticosteroids, and immunosuppressants. In some embodiments, the immunosuppressants are selected from: azathioprine, mycophenolate mofetil/mycophenolic acid, methotrexate, cyclosporine, tacrolimus, and cyclophosphamide. In some embodiments, the method comprise administering a pharmaceutical composition comprising administering an anti-FcRN antibody to the subject. In some embodiments, the anti-FcRN antibody is nipocalimab, RVT-1401 (HL161), rozanolixizumab (UCB7665), ALXN1830, ABY-039, or efgartigimod.

In some embodiments, the pharmaceutical composition comprises an anti-FcRn antibody comprising a heavy chain and a light chain, wherein the heavy chain comprises a HCDR 1 of SEQ ID NO: 6, a HCDR2 of SEQ ID NO: 7, and a HCDR3 of SEQ ID NO: 8; and wherein the light chain comprises a LCDR 1 of SEQ ID NO: 3, a LCDR2 of SEQ ID NO: 4, and a LCDR3 of SEQ ID NO: 5.

In some embodiments, the pharmaceutical composition comprises an anti-FcRn antibody wherein the heavy chain comprises a variable region heavy chain comprising an amino acid sequence having at least 90% identity to the sequence of SEQ ID NO: 10 and the light chain comprises a variable region light chain comprising an amino acid sequence having at least 90% identity to the sequence of SEQ ID NO: 9. In some embodiments, the pharmaceutical composition comprises an anti-FcRn antibody wherein the heavy chain comprises a variable region heavy chain comprising an amino acid sequence having at least 95% identity to the sequence of SEQ ID NO: 10 and the light chain comprises a variable region light chain comprising an amino acid sequence having at least 95% identity to the sequence of SEQ ID NO: 9. In some embodiments, the pharmaceutical composition comprises an anti-FcRn antibody wherein the heavy chain comprises a variable region heavy chain comprising an amino acid sequence having at least 99% identity to the sequence of SEQ ID NO: 10 and the light chain comprises a variable region light chain comprising an amino acid sequence having at least 99% identity to the sequence of SEQ ID NO: 9. In some embodiments, the pharmaceutical composition comprises an anti-FcRn antibody wherein the heavy chain comprises an amino acid sequence having at least 90% identity to the sequence of SEQ ID NO: 2 and the light chain comprises an amino acid sequence having at least 90% identity to the sequence of SEQ ID NO: 1. In some embodiments, the pharmaceutical composition comprises an anti-FcRn antibody wherein the heavy chain comprises an amino acid sequence having at least 95% identity to the sequence of SEQ ID NO: 2 and the light chain comprises an amino acid sequence having at least 95% identity to the sequence of SEQ ID NO: 1. In some embodiments, the pharmaceutical composition comprises an anti-FcRn antibody wherein the heavy chain comprises an amino acid sequence having at least 99% identity to the sequence of SEQ ID NO: 2 and the light chain comprises an amino acid sequence having at least 99% identity to the sequence of SEQ ID NO: 1. In some embodiments, the pharmaceutical composition comprises an anti-FcRn antibody wherein the heavy chain comprises a variable region heavy chain comprising the amino acid sequence of SEQ ID NO: 10 and the light chain comprises a variable region light chain comprising the amino acid sequence of SEQ ID NO: 9. In some embodiments, the pharmaceutical composition comprises an anti-FcRn antibody wherein the heavy chain comprises the amino acid sequence of SEQ ID NO: 2 and the light chain comprises the amino acid sequence of SEQ ID NO: 1.

In some embodiments, the pharmaceutical composition comprises a therapeutically effective amount of the anti-FcRN antibody. In some embodiments, the pharmaceutical composition comprises a therapeutically effective amount of the anti-FcRN antibody. In some embodiments, the therapeutically effective amount is from about 5 mg/kg to about 60 mg/kg, about 5 mg/kg to about 15 mg/kg, about 15 mg/kg to about 60 mg/kg, or about 30 mg/kg to about 60 mg/kg of the anti-FcRN antibody. In some embodiments, the therapeutically effective amount is about 5 mg/kg, about 15 mg/kg, about 30 mg/kg, or about 60 mg/kg. In some embodiments, the therapeutically effective amount is about 5 mg/kg. In some embodiments, the therapeutically effective amount is about 15 mg/kg. In some embodiments, the therapeutically effective amount is about 30 mg/kg. In some embodiments, the therapeutically effective amount is about 60 mg/kg. In some embodiments, the pharmaceutical composition comprises an initial loading dose and a maintenance dose. In some embodiments, the initial loading dose is about 60 mg/kg. In some embodiments, the initial loading dose is about 30 mg/kg. In some embodiments, the maintenance dose is about 30 mg/kg. In some embodiments, the maintenance dose is about 15 mg/kg. In some embodiments, the pharmaceutical composition is administered at an initial loading dose of about 60 mg/kg and a maintenance dose of about 30 mg/kg. In some embodiments, the pharmaceutical composition is administered at an initial loading dose of about 60 mg/kg and a maintenance dose of about 15 mg/kg. In some embodiments, the pharmaceutical composition is administered at an initial loading dose of about 30 mg/kg and a maintenance dose of about 30 mg/kg. In some embodiments, the pharmaceutical composition is administered at an initial loading dose of about 30 mg/kg and a maintenance dose of about 15 mg/kg.

In some embodiments, the pharmaceutical composition is administered every week, every two weeks, or monthly.

In some embodiments, the administration of the pharmaceutical composition to the patient to treat myasthenia gravis results in the patient showing improvement in MG-ADL score, QMG score, MG-QoL15r score, Neuro-QoL-Fatigue score, EQ-5D-5L score, MGFA scale, PGI-C score, PGI-S score, C-SSRS score, and PedsQL score.

In some embodiments, the administration of the pharmaceutical composition to the patient to treat myasthenia gravis treats or ameliorates ocular myasthenia, ptosis, difficulty chewing, dysphagia, dysarthria, hypophonia, dyspnea, an inability to hold the mouth closed, an appearance of sadness or sleepiness, difficulty holding the head upright, diplopia, dysarthria, difficulty swallowing, change in facial expression, shortness of breath, weakness in arms, weakness in hands, weakness in fingers, weakness in legs, weakness in neck.

In some embodiments, the administration of the pharmaceutical composition to the patient shows a reduction in one or more immunoglobulin isotypes or total IgG in the patient. In some embodiments, the isotype is IgG1, IgG2, IgG3, or IgG4. In some embodiments, the reduction is about 1%, 2%, 3%, 4%, 5%, 6%, 7%, 8%, 9%, 10%, 1-20%, 5-20%, 5-25%, 10-30%, 15-35%, 20-40%, 40-60%, or, about, or at least, 5%, 10%, 15%, 20%, 25%, 30%, 35%, 40%, 45%, 50%, 60%, 70%, or 80%. In some embodiments, the administration of the pharmaceutical composition reduces serum IgG by at least 10%, at least 20%, at least 30%, at least 40%, at least 50%, at least 60%, at least 70%, at least 80%, or at least 90% of baseline serum IgG. In some embodiments, the administration of the pharmaceutical composition reduces serum IgG in the patient by at least 90% of baseline. In some embodiments, the administration of the pharmaceutical composition reduces serum IgG in the patient by at least 80% of baseline. In some embodiments, the administration of the pharmaceutical composition reduces serum IgG in the patient by at least 70% of baseline. In some embodiments, the isotype of immunoglobulins reduced is IgG1, IgG2, IgG3, IgG4, or any combination thereof. In some embodiments, the administration of the pharmaceutical composition reduces serum IgG1 by at least 10%, at least 20%, at least 30%, at least 40%, at least 50%, at least 60%, at least 70%, at least 80%, or at least 90% of baseline serum IgG1. In some embodiments, the administration of the pharmaceutical composition reduces serum IgG1 in the patient by at least 90% of baseline. In some embodiments, the administration of the pharmaceutical composition reduces serum IgG1 in the patient by at least 80% of baseline. In some embodiments, the administration of the pharmaceutical composition reduces serum IgG1 in the patient by at least 70% of baseline. In some embodiments, the administration of the pharmaceutical composition reduces serum IgG2 by at least 10%, at least 20%, at least 30%, at least 40%, at least 50%, at least 60%, at least 70%, at least 80%, or at least 90% of baseline serum IgG2. In some embodiments, the administration of the pharmaceutical composition reduces serum IgG2 in the patient by at least 90% of baseline. In some embodiments, the administration of the pharmaceutical composition reduces serum IgG2 in the patient by at least 80% of baseline. In some embodiments, the administration of the pharmaceutical composition reduces serum IgG2 in the patient by at least 70% of baseline. In some embodiments, the administration of the pharmaceutical composition reduces serum IgG3 by at least 10%, at least 20%, at least 30%, at least 40%, at least 50%, at least 60%, at least 70%, at least 80%, or at least 90% of baseline serum IgG3. In some embodiments, the administration of the pharmaceutical composition reduces serum IgG3 in the patient by at least 90% of baseline. In some embodiments, the administration of the pharmaceutical composition reduces serum IgG3 in the patient by at least 80% of baseline. In some embodiments, the administration of the pharmaceutical composition reduces serum IgG3 in the patient by at least 70% of baseline. In some embodiments, the administration of the pharmaceutical composition reduces serum IgG4 by at least 10%, at least 20%, at least 30%, at least 40%, at least 50%, at least 60%, at least 70%, at least 80%, or at least 90% of baseline serum IgG4. In some embodiments, the administration of the pharmaceutical composition reduces serum IgG4 in the patient by at least 90% of baseline. In some embodiments, the administration of the pharmaceutical composition reduces serum IgG4 in the patient by at least 80% of baseline. In some embodiments, the administration of the pharmaceutical composition reduces serum IgG4 in the patient by at least 70% of baseline.

In some embodiments, the administration of the pharmaceutical composition reduces serum albumin by at most 18%, at most 16%, at most 14%, at most 12%, at most 10%, at most 8%, at least 6%, at most 4%, or at most 2% of baseline of serum albumin. In some embodiments, the administration of the pharmaceutical composition reduces serum albumin by at most 18% of baseline of serum albumin. In some embodiments, the administration of the pharmaceutical composition reduces serum albumin by at most 16% of baseline of serum albumin. In some embodiments, the administration of the pharmaceutical composition reduces serum albumin by at most 14% of baseline of serum albumin. In some embodiments, the administration of the pharmaceutical composition reduces serum albumin by at most 12% of baseline of serum albumin. In some embodiments, the administration of the pharmaceutical composition reduces serum albumin by at most 10% of baseline of serum albumin. In some embodiments, the administration of the pharmaceutical composition reduces serum albumin by at most 8% of baseline of serum albumin. In some embodiments, the administration of the pharmaceutical composition reduces serum albumin by at most 6% of baseline of serum albumin. In some embodiments, the administration of the pharmaceutical composition reduces serum albumin by at most 4% of baseline of serum albumin. In some embodiments, the administration of the pharmaceutical composition reduces serum albumin by at most 2% of baseline of serum albumin.

In some embodiments, the administration of the pharmaceutical composition to the patient shows a reduction in autoantibodies in the patient. In some embodiments, the autoantibodies are selected from the group consisting of: anti-acetylcholine receptors (AChRs), anti-muscle-specific kinase (MuSK) anti-low-density lipoprotein receptor-related protein 4 (LRP4), anti-agrin, anti-titin, anti-Kv1.4, anti-ryanodine receptors, anti-collagen Q, and anti-cortactin. In some embodiments, the reduction is about 1%, 2%, 3%, 4%, 5%, 6%, 7%, 8%, 9%, 10%, 1-20%, 5-20%, 5-25%, 10-30%, 15-35%, 20-40%, 40-60%, or, about, or at least, 5%, 10%, 15%, 20%, 25%, 30%, 35%, 40%, 45%, 50%, 60%, 70%, 80%, 90%, or 95%. In some embodiments, the autoantibodies are anti-AChR or anti-MuSK antibodies. In some embodiments, the administration of the pharmaceutical composition reduces anti-AChR antibodies by at least 95%, at least 90%, at least 85%, at least 80%, at least 75%, at least 50%, or at least 25% of baseline anti-AChR antibodies. In some embodiments, the administration of the pharmaceutical composition reduces anti-AChR antibodies by at least 95% of baseline anti-AChR antibodies. In some embodiments, the administration of the pharmaceutical composition reduces anti-AChR antibodies by at least 90% of baseline anti-AChR antibodies. In some embodiments, the administration of the pharmaceutical composition reduces anti-AChR antibodies by at least 85% of baseline anti-AChR antibodies. In some embodiments, the administration of the pharmaceutical composition reduces anti-AChR antibodies by at least 80% of baseline anti-AChR antibodies. In some embodiments, the administration of the pharmaceutical composition reduces anti-AChR antibodies by at least 75% of baseline anti-AChR antibodies. In some embodiments, the administration of the pharmaceutical composition reduces anti-AChR antibodies by at least 50% of baseline anti-AChR antibodies. In some embodiments, the administration of the pharmaceutical composition reduces anti-AChR antibodies by at least 25% of baseline anti-AChR antibodies. In some embodiments, the administration of the pharmaceutical composition reduces anti-MuSK antibodies by at least 95%, at least 90%, at least 85%, at least 80%, at least 75%, at least 50%, or at least 25% of baseline anti-MuSK antibodies. In some embodiments, the administration of the pharmaceutical composition reduces anti-MuSK antibodies by at least 95% of baseline anti-MuSK antibodies. In some embodiments, the administration of the pharmaceutical composition reduces anti-MuSK antibodies by at least 90% of baseline anti-MuSK antibodies. In some embodiments, the administration of the pharmaceutical composition reduces anti-MuSK antibodies by at least 85% of baseline anti-MuSK antibodies. In some embodiments, the administration of the pharmaceutical composition reduces anti-MuSK antibodies by at least 80% of baseline anti-MuSK antibodies. In some embodiments, the administration of the pharmaceutical composition reduces anti-MuSK antibodies by at least 75% of baseline anti-MuSK antibodies. In some embodiments, the administration of the pharmaceutical composition reduces anti-MuSK antibodies by at least 50% of baseline anti-MuSK antibodies. In some embodiments, the administration of the pharmaceutical composition reduces anti-MuSK antibodies by at least 25% of baseline anti-MuSK antibodies. In some embodiments, the administration of the pharmaceutical composition reduces anti-AChR antibodies by at least 95%, at least 90%, at least 85%, at least 80%, at least 75%, at least 50%, or at least 25% of baseline anti-AChR antibodies; and anti-MuSK antibodies by at least 95%, at least 90%, at least 85%, at least 80%, at least 75%, at least 50%, or at least 25% of baseline anti-MuSK antibodies.

In some embodiments, the administration of the pharmaceutical composition to the patient to treat myasthenia gravis results in the patient showing change from baseline of MG-ADL score. In some embodiments, the administration of the pharmaceutical composition to the patient to treat myasthenia gravis results in a change from baseline of MG-ADL score that is greater than or equal to 2 points on the MG-ADL scale. In some embodiments, the administration of the pharmaceutical composition to the patient to treat myasthenia gravis results in the patient showing change from baseline of MG-ADL score. In some embodiments, the administration of the pharmaceutical composition to the patient to treat myasthenia gravis results in a change from baseline of MG-ADL score that is greater than or equal to 2 points on the MG-ADL scale. In some embodiments, the administration of the pharmaceutical composition to the patient results in an improvement in the patient as measured by ACR score over time or 22, 23, and 24 weeks after administration of the first dose of the pharmaceutical composition to the patient.

In some embodiments, the administration of the pharmaceutical composition to the patient to treat myasthenia gravis results in the patient showing a change from baseline in QMG score after 57 days of treatment. In some embodiments, the administration of the pharmaceutical composition to the patient to treat myasthenia gravis results in the patient showing a change from baseline in QMG score over time after administration of the last dose. In some embodiments, the change from baseline is at least a 2, 3, 4, 5, 6, 7, or greater than or equal to 8 point reduction in the patient's QMG score over time after administration of the last dose of the pharmaceutical composition. In some embodiments, the change from baseline is at least a 2 point reduction in the patient's QMG score over time after administration of the last dose of the pharmaceutical composition. In some embodiments, the change from baseline is at least a 3 point reduction in the patient's QMG score over time after administration of the last dose of the pharmaceutical composition. In some embodiments, the change from baseline is at least a 4 point reduction in the patient's QMG score over time after administration of the last dose of the pharmaceutical composition. In some embodiments, the change from baseline is at least a 5 point reduction in the patient's QMG score over time after administration of the last dose of the pharmaceutical composition. In some embodiments, the change from baseline is at least a 6 point reduction in the patient's QMG score over time after administration of the last dose of the pharmaceutical composition. In some embodiments, the change from baseline is at least a 7 point reduction in the patient's QMG score over time after administration of the last dose of the pharmaceutical composition. In some embodiments, the change from baseline is greater than or equal to 8 point reduction in the patient's QMG score over time after administration of the last dose of the pharmaceutical composition. In some embodiments, the administration of the pharmaceutical composition to the patient to treat myasthenia gravis results in the patient showing a change from baseline in QMG score after 22, 23, and 24 weeks of treatment or over time after administration of the last dose. In some embodiments, the administration of the pharmaceutical composition to the patient to treat myasthenia gravis results in the patient showing a change from baseline in QMG score over time after administration of the last dose. In some embodiments, the change from baseline is at least a 2, 3, 4, 5, 6, 7, or greater than or equal to 8 point reduction in the patient's QMG score after 22, 23, and 24 weeks of treatment or over time after administration of the last dose of the pharmaceutical composition. In some embodiments, the change from baseline is at least a 2 point reduction in the patient's QMG score after 22, 23, and 24 weeks of treatment or over time after administration of the last dose of the pharmaceutical composition. In some embodiments, the change from baseline is at least a 3 point reduction in the patient's QMG score after 22, 23, and 24 weeks of treatment or over time after administration of the last dose of the pharmaceutical composition. In some embodiments, the change from baseline is at least a 4 point reduction in the patient's QMG score after 22, 23, and 24 weeks of treatment or over time after administration of the last dose of the pharmaceutical composition. In some embodiments, the change from baseline is at least a 5 point reduction in the patient's QMG score after 22, 23, and 24 weeks of treatment or over time after administration of the last dose of the pharmaceutical composition. In some embodiments, the change from baseline is at least a 6 point reduction in the patient's QMG score after 22, 23, and 24 weeks of treatment or over time after administration of the last dose of the pharmaceutical composition. In some embodiments, the change from baseline is at least a 7 point reduction in the patient's QMG score after 22, 23, and 24 weeks of treatment or over time after administration of the last dose of the pharmaceutical composition. In some embodiments, the change from baseline is greater than or equal to 8 point reduction in the patient's QMG score after 22, 23, and 24 weeks of treatment or over time after administration of the last dose of the pharmaceutical composition.

In some embodiments, the administration of the pharmaceutical composition to the patient to treat myasthenia gravis results in the patient showing a change from baseline in MG-QoL15 score after 57 days of treatment. In some embodiments, the administration of the pharmaceutical composition to the patient to treat myasthenia gravis results in the patient showing a change from baseline in MG-QoL15 score over time after administration of the last dose. In some embodiments, the administration of the pharmaceutical composition to the patient to treat myasthenia gravis results in the patient showing a change from baseline in MG-QoL15 score after 22, 23, and 24 weeks of treatment or over time after administration of the last dose. In some embodiments, the administration of the pharmaceutical composition to the patient to treat myasthenia gravis results in the patient showing a change from baseline in MG-QoL15 score over time after administration of the last dose. In some embodiments, the patient achieves a change from baseline on MG-QoL-15r scale that is at least a 3, 4, 5, or 6 point reduction in MG-QoL-15r score. In some embodiments, the patient achieves a change from baseline on MG-QoL-15r scale that is at least a 3 point reduction in MG-QoL-15r score. In some embodiments, the patient achieves a change from baseline on MG-QoL-15r scale that is at least a 6 point reduction in MG-QoL-15r score.

In some embodiments, the administration of the pharmaceutical composition to the patient to treat myasthenia gravis results in the patient showing a shift in MGFA classification after 57 days of treatment and over time. In some embodiments, the administration of the pharmaceutical composition to the patient to treat myasthenia gravis results in the patient showing a shift in MGFA classification over time after administration of the last dose of the pharmaceutical composition. In some embodiments, the shift is about 1%, 2%, 3%, 4%, 5%, 6%, 7%, 8%, 9%, 1%, 1-20%, 5-20%, 5-25%, 10-30%, 15-35%, 20-40%, 40-60%, or, about, or at least, 5%, 10%, 15%, 20%, 25%, 30%, 35%, 40%, 45%, 50%, 60%, 70%, or 80%. In some embodiments, the administration of the pharmaceutical composition to the patient to treat myasthenia gravis results in the patient showing a shift in MGFA classification after 22, 23, and 24 weeks of treatment or over time after administration of the last dose. In some embodiments, the administration of the pharmaceutical composition to the patient to treat myasthenia gravis results in the patient showing a shift in MGFA classification over time after administration of the last dose of the pharmaceutical composition. In some embodiments, the shift is about 1%, 2%, 3%, 4%, 5%, 6%, 7%, 8%, 9%, 10%, 1-20%, 5-20%, 5-25%, 10-30%, 15-35%, 20-40%, 40-60%, or, about, or at least, 5%, 10%, 15%, 20%, 25%, 30%, 35%, 40%, 45%, 50%, 60%, 70%, or 80%.

In some embodiments, the administration of the pharmaceutical composition to the patient to treat myasthenia gravis results in a change from baseline on the Neuro-QoL-Fatigue scale after 22, 23, and 24 weeks of treatment. In some embodiments, the administration of the pharmaceutical composition to the patient to treat myasthenia gravis results in a change from baseline on the Neuro-QoL-Fatigue scale over time after administration of the last dose. In some embodiments, the change from baseline on the Neuro-QoL-Fatigue indicates improvement.

In some embodiments, the administration of the pharmaceutical composition to the patient to treat myasthenia gravis results in a change from baseline on the EQ-5D-5L scale. In some embodiments, the change from baseline on the EQ-5D-5L scale indicates improvement. In some embodiments, the administration of the pharmaceutical composition to the patient to treat myasthenia gravis results in a change from baseline on EQ-5D-5L scale after 22, 23, and 24 weeks of treatment or over time after administration of the last dose.

In some embodiments, the administration of the pharmaceutical composition to the patient to treat myasthenia gravis results in a change from baseline on the PGI-C scale. In some embodiments, the change from baseline on the PGI-C scale indicates improvement. In some embodiments, the administration of the pharmaceutical composition to the patient to treat myasthenia gravis results in a change from baseline on PGI-C scale after 22, 23, and 24 weeks of treatment or over time after administration of the last dose.

In some embodiments, the administration of the pharmaceutical composition to the patient to treat myasthenia gravis results in a change from baseline on the PGI-S scale. In some embodiments, the change from baseline on the PGI-S scale indicates improvement. In some embodiments, the administration of the pharmaceutical composition to the patient to treat myasthenia gravis results in a change from baseline on PGI-S scale after 22, 23, and 24 weeks of treatment or over time after administration of the last dose.

In some embodiments the administration of the pharmaceutical composition to the patient to treat myasthenia gravis results in a change from baseline on the C-SSRS scale. In some embodiments, the change from baseline on the C-SSRS scale indicates improvement. In some embodiments, the administration of the pharmaceutical composition to the patient to treat myasthenia gravis results in a change from baseline on C-SSRS scale after 22, 23, and 24 weeks of treatment or over time after administration of the last dose.

In some embodiments, the administration of the pharmaceutical composition to the pediatric patient to treat myasthenia gravis results in a change from baseline on PedsQL scale. In some embodiments, the change from baseline on PedsQL scale indicates improvement. In some embodiments, the administration of the pharmaceutical composition to the pediatric patient to treat myasthenia gravis results in a change from baseline on PedsQL scale after 2, 4, 5, 6, 7, 8, 9, 10, 11, 12, 13, 14, 15, 16, 17, 18, 19, 20, 21, 22, and 24 weeks of treatment or over time after administration of the last dose. In some embodiments, the change is about 1%, 2%, 3%, 4%, 5%, 6%, 7%, 8%, 9%, 10%, 1-20%, 5-20%, 5-25%, 10-30%, 15-35%, 20-40%, 40-60%, or, about, or at least, 5%, 10%, 15%, 20%, 25%, 30%, 35%, 40%, 45%, 50%, 60%, 70%, 80%, 90%, or 95%.

In some embodiments, the subject being treated for myasthenia gravis with an anti-FcRn antibody does not experience significantly increased levels of total cholesterol, high-density lipoprotein (HDL), calculated low-density lipoprotein (LDL), and triglycerides after being treated with the antibody. In some embodiments, the antibody an anti-FcRn antibody. In some embodiments, the anti-FcRn antibody is as provided herein. In some embodiments, the subject being treated for myasthenia gravis with an anti-FcRn antibody does not experience significantly increased levels of total cholesterol after being treated with the antibody. In some embodiments, the subject being treated for myasthenia gravis with an anti-FcRn antibody does not experience significantly increased levels of high-density lipoprotein (HDL) after being treated with the antibody. In some embodiments, the subject being treated for myasthenia gravis with an anti-FcRn antibody does not experience significantly increased levels of calculated low-density lipoprotein (LDL) after being treated with the antibody. In some embodiments, the subject being treated for myasthenia gravis with an anti-FcRn antibody does not experience significantly increased levels of triglycerides after being treated with the antibody. In some embodiments, the subject being treated for myasthenia gravis with an anti-FcRn antibody does not experience significantly increased levels of total cholesterol after being treated with the anti-FcRn antibody. In some embodiments, the subject being treated myasthenia gravis with an anti-FcRn antibody does not experience significantly increased levels of high-density lipoprotein (HDL) after being treated with the anti-FcRn antibody. In some embodiments, the subject being treated for myasthenia gravis with an anti-FcRn antibody does not experience significantly increased levels of calculated low-density lipoprotein (LDL) after being treated with the anti-FcRn antibody. In some embodiments, the subject being treated for myasthenia gravis with an anti-FcRn antibody does not experience significantly increased levels of triglycerides after being treated with the anti-FcRn antibody. In preferred embodiments, the anti-FcRn antibody is nipocalimab.

In some embodiments, the administration of the pharmaceutical composition to the patient does not significantly increase levels of total cholesterol, high-density lipoprotein (HDL), calculated low-density lipoprotein (LDL), and triglycerides after administration of the pharmaceutical composition comprising the antibody. In some embodiments, the antibody is an anti-FcRn antibody. In some embodiments, the anti-FcRn antibody is as provided herein. In some embodiments, the administration of the pharmaceutical composition to the patient does not significantly increase levels of total cholesterol after administration of the pharmaceutical composition comprising the antibody. In some embodiments, the administration of the pharmaceutical composition to the patient does not significantly increase levels of high-density lipoprotein (HDL) after administration of the pharmaceutical composition comprising the antibody. In some embodiments, the administration of the pharmaceutical composition to the patient does not significantly increase levels of calculated low-density lipoprotein (LDL) after administration of the pharmaceutical composition comprising the antibody. In some embodiments, the administration of the pharmaceutical composition to the patient does not significantly increase levels of triglycerides after administration of the pharmaceutical composition comprising the antibody. In some embodiments, the administration of the pharmaceutical composition to the patient does not significantly increase levels of total cholesterol after administration of the pharmaceutical composition comprising the anti-FcRn antibody. In some embodiments, the administration of the pharmaceutical composition to the patient does not significantly increase levels of high-density lipoprotein (HDL) after administration of the pharmaceutical composition comprising the anti-FcRn antibody. In some embodiments, the administration of the pharmaceutical composition to the patient does not significantly increase levels of calculated low-density lipoprotein (LDL) after administration of the pharmaceutical composition comprising the anti-FcRn antibody. In some embodiments, the administration of the pharmaceutical composition to the patient does not significantly increase levels of triglycerides after administration of the pharmaceutical composition comprising the anti-FcRn antibody. In preferred embodiments, the anti-FcRn antibody is nipocalimab.

As used herein, the phrase "does not significantly increase" when used in reference to levels (measurements) of total cholesterol, high-density lipoprotein (HDL), calculated low-density lipoprotein (LDL), or triglycerides" means that any increase is at most 30% as compared to the level(s) prior (baseline) to the administration of the antibody or compositions provided for herein. In some embodiments, the increase is at most 25%, 20%, 15%, 10%, or 5%. In some embodiments, the increase is at most about 1 to about 30%, about 5% to about 25%, about 1% to about 20%, about 1% to about 15%, about 1% to about 10%, about 5% to about 15%, about 5% to about 20%, about 10% to about 20%, about 1%, about 5%, about 10%, about 15%, about 20%, about 25%, or about 30%.

The disclosures of each and every patent, patent application, and publication cited herein are hereby incorporated herein by reference in their entirety. While various embodiments have been disclosed with reference to specific aspects, it is apparent that other aspects and variations of these embodiments may be devised by others skilled in the art without departing from the true spirit and scope of the embodiments. The appended claims are intended to be construed to include all such aspects and equivalent variations.

OTHER EMBODIMENTS

While the disclosure has been described in connection with specific embodiments thereof, it will be understood that it is capable of further modifications and this application is intended to cover any variations, uses, or adaptations following, in general, the principles and including such departures from the present disclosure come within known or customary practice within the art to which the disclosure pertains and may be applied to the essential features hereinbefore set forth.

In some embodiments, embodiments provided herein also include, but are not limited to:

1. A method of treating myasthenia gravis in a patient in need thereof, the method comprising administering an initial loading dose of about 30 mg/kg mg/kg to about 60 mg/kg of an anti-FcRn antibody followed by administering a maintenance dose of about 15 mg/kg to about 30 mg/kg of the anti-FcRn antibody, wherein the anti-FcRn antibody comprises:

a heavy chain comprising a HCDR1 of SEQ ID NO: 6, a HCDR2 of SEQ ID NO: 7, and a HCDR3 of SEQ ID NO: 8; and a light chain comprising a LCDR1 of SEQ ID NO: 3, a LCDR2 of SEQ ID NO: 4, and a LCDR3 of SEQ ID NO: 5;

wherein the administration reduces serum IgG in the patient by at least 10%, at least 20%, at least 30%, at least 40%, at least 50%, at least 60%, at least 70%, at least 80%, or at least 90% of baseline serum IgG.

2. The method of embodiment 1, wherein the heavy chain comprises an amino acid sequence having at least 90% identity to the sequence of SEQ ID NO: 2 and the light chain comprises an amino acid sequence having at least 90% identity to the sequence of SEQ ID NO: 1.

3. The method of embodiment 1, wherein the heavy chain comprises an amino acid sequence having at least 95% identity to the sequence of SEQ ID NO: 2 and the light chain comprises an amino acid sequence having at least 95% identity to the sequence of SEQ ID NO: 1.

4. The method of embodiment 1, wherein the heavy chain comprises an amino acid sequence having at least 99% identity to the sequence of SEQ ID NO: 2 and the light chain comprises an amino acid sequence having at least 99% identity to the sequence of SEQ ID NO: 1.

5. The method of embodiment 1, wherein the heavy chain comprises a variable region heavy chain comprising an amino acid sequence having at least 90% identity to the sequence of SEQ ID NO: 10 and the light chain comprises a variable region light chain comprising an amino acid sequence having at least 90% identity to the sequence of SEQ ID NO: 9.

6. The method of embodiment 1, wherein the heavy chain comprises a variable region heavy chain comprising an amino acid sequence having at least 95% identity to the sequence of SEQ ID NO: 10 and the light chain comprises a variable region light chain comprising an amino acid sequence having at least 95% identity to the sequence of SEQ ID NO: 9.

7. The method of embodiment 1, wherein the heavy chain comprises a variable region heavy chain comprising an amino acid sequence having at least 99% identity to the sequence of SEQ ID NO: 10 and the light chain comprises a variable region light chain comprising an amino acid sequence having at least 99% identity to the sequence of SEQ ID NO: 9.

8. The method of embodiment 1, wherein the heavy chain comprises the amino acid sequence of SEQ ID NO: 2 and the light chain comprises the amino acid sequence of SEQ ID NO: 1.

9. The method of embodiment 1, wherein the heavy chain comprises a variable region heavy chain comprising the amino acid sequence of SEQ ID NO: 10 and the light chain comprises a variable region light chain comprising the amino acid sequence of SEQ ID NO: 9.

10. The method of any one of embodiments 1-9, wherein the patient is suffering from generalized myasthenia gravis.

11. The method of any one of embodiment 1-10, wherein the patient is an adult patient or a pediatric patient.

12. The method of any one of embodiments 1-11, wherein the administration is intravenous or subcutaneous.

13. The method of any one of embodiments 1-12, wherein the administration comprises administering a pharmaceutical composition comprising about 10 mg/ml to about 60 mg/ml of the anti-FcRn antibody, about 20 mM to about 30 mM sodium phosphate, about 20 mM to about 30 mM sodium chloride, about 80 mg/ml to about 100 mg/ml Trehalose, and about 0.1% w/v to about 0.005% w/v Polysorbate 80.

14. The method of any one of embodiments 1-13, wherein the initial loading dose is about 60 mg/kg or about 30 mg/kg.

15. The method of any one of embodiments 1-14, wherein the initial loading dose is about 60 mg/kg.

16. The method of any one of embodiments 1-14, wherein the initial loading dose is about 30 mg/kg.

17. The method of any one of embodiments 1-16, wherein the maintenance dose is about 15 mg/kg, about 30 mg/kg, about 45 mg/kg, or about 60 mg/kg.

18. The method of any one of embodiments 1-17, wherein the maintenance dose is about 15 mg/kg.

19. The method of any one of embodiments 1-17, wherein the maintenance dose is about 30 mg/kg.

20. The method of any one of embodiments 1-19, wherein the maintenance dose is administered:

1 week, 2 weeks, 3 weeks, or 4 weeks after the administration of the initial loading dose; and 1 week, 2 weeks, 3 weeks, 4 weeks, or monthly after the administration of the preceding maintenance dose.

21. The method of any one of embodiments 1-20, wherein the maintenance dose is administered 1 week, 2 weeks, 3 weeks, or 4 weeks after the administration of the initial loading dose.

22. The method of any one of embodiments 1-21, wherein the maintenance dose is administered 1 week, 2 weeks, 3 weeks, or 4 weeks after the administration of the preceding maintenance dose.

23. The method of any one of embodiments 1-22, wherein:

the initial loading dose is infused into the subject in about 30 minutes to about 90 minutes; and the maintenance dose is infused into the subject in about 15 to about 60 minutes.

24. The method of any one of embodiments 1-23, wherein the initial loading dose is infused into the subject in about 30 minutes to about 90 minutes.

25. The method of any one of embodiments 1-24, wherein the maintenance dose is infused into the subject in about 15 to about 60 minutes.

26. The method of any one of embodiments 1-25, wherein the serum IgG is IgG1, IgG2, IgG3, or IgG4, or any combination thereof, and wherein the reduction is at least 80% of baseline, or at least 70% of baseline.

27. The method of any one of embodiments 1-26, wherein the administration of the anti-FcRn antibody reduces serum IgG in the patient by at least 20% of baseline.

28. The method of any one of embodiments 1-26, wherein the administration of the anti-FcRn antibody reduces serum IgG in the patient by at least 30% of baseline.

29. The method of any one of embodiments 1-28, wherein the administration of the anti-FcRn antibody reduces serum albumin by at most 18%, at most 16%, at most 14%, at most 12%, at most 10%, at most 8%, at most 6%, at most 4%, or at most 2% of baseline of serum albumin.

30. The method of any one of embodiments 1-29, wherein the administration reduces serum autoantibodies, wherein:

the autoantibodies are selected from the group consisting of: anti-acetylcholine receptors (AChRs), anti-muscle-specific kinase (MuSK) anti-low-density lipoprotein receptor-related protein 4 (LRP4), anti-agrin, anti-titin, anti-Kv1.4, anti-ryanodine receptors, anti-collagen Q, and anti-cortactin; and the reduction is by at least 95%, at least 90%, at least 85%, at least 80%, at least 75%, at least 50%, or at least 25% of baseline serum autoantibodies.

31. The method of embodiment 30, wherein the administration of the anti-FcRn antibody reduces anti-AChR antibodies by at least 95%, at least 90%, at least 85%, at least 80%, at least 75%, at least 50%, or at least 25% of baseline anti-AChR antibodies.

32. The method of any one of embodiments 30-31, wherein the administration of the anti-FcRn antibody reduces anti-MuSK antibodies by at least 95%, at least 90%, at least 85%, at least 80%, at least 75%, at least 50%, or at least 25% of baseline anti-MuSK antibodies.

33. The method of any one of embodiments 1-32, wherein the patient achieves a change from baseline in MG-ADL score, QMG score, MG-QoL-15r score, MGFA score, or any combination thereof.

34. The method of any one of embodiments 1-33, wherein the administration of the anti-FcRn antibody to the subject does not significantly increase levels of total cholesterol, HDL, calculated LDL, and triglycerides in the subject as compared to the levels prior to the administration of the anti-FcRn antibody.

35. A method of treating myasthenia gravis in a patient in need thereof, the method comprising administering an initial loading dose of about 30 mg/kg mg/kg to about 60 mg/kg of an anti-FcRn antibody followed by administering a maintenance dose of about 15 mg/kg to about 30 mg/kg of the anti-FcRn antibody, wherein the anti-FcRn antibody comprises:

a heavy chain comprising a HCDR1 of SEQ ID NO: 6, a HCDR2 of SEQ ID NO: 7, and a HCDR3 of SEQ ID NO: 8; and a light chain comprising a LCDR1 of SEQ ID NO: 3, a LCDR2 of SEQ ID NO: 4, and a LCDR3 of SEQ ID NO: 5;

wherein the administration reduces serum autoantibodies by at least 95%, at least 90%, at least 85%, at least 80%, at least 75%, at least 50%, or at least 25% of baseline serum autoantibodies.

36. The method of embodiment 35, wherein the heavy chain comprises an amino acid sequence having at least 90% identity to the sequence of SEQ ID NO: 2 and the light chain comprises an amino acid sequence having at least 90% identity to the sequence of SEQ ID NO: 1.

37. The method of embodiment 35, wherein the heavy chain comprises an amino acid sequence having at least 95% identity to the sequence of SEQ ID NO: 2 and the light chain comprises an amino acid sequence having at least 95% identity to the sequence of SEQ ID NO: 1.

38. The method of embodiment 35, wherein the heavy chain comprises an amino acid sequence having at least 99% identity to the sequence of SEQ ID NO: 2 and the light chain comprises an amino acid sequence having at least 99% identity to the sequence of SEQ ID NO: 1.

39. The method of embodiment 35, wherein the heavy chain comprises a variable region heavy chain comprising an amino acid sequence having at least 90% identity to the sequence of SEQ ID NO: 10 and the light chain comprises a variable region light chain comprising an amino acid sequence having at least 90% identity to the sequence of SEQ ID NO: 9.

40. The method of embodiment 35, wherein the heavy chain comprises a variable region heavy chain comprising an amino acid sequence having at least 95% identity to the sequence of SEQ ID NO: 10 and the light chain comprises a variable region light chain comprising an amino acid sequence having at least 95% identity to the sequence of SEQ ID NO: 9.

41. The method of embodiment 35, wherein the heavy chain comprises a variable region heavy chain comprising an amino acid sequence having at least 99% identity to the sequence of SEQ ID NO: 10 and the light chain comprises a variable region light chain comprising an amino acid sequence having at least 99% identity to the sequence of SEQ ID NO: 9.

42. The method of embodiment 35, wherein the variable region heavy chain comprises the amino acid sequence of SEQ ID NO: 10 and the variable region light chain comprises the amino acid sequence of SEQ ID NO: 9.

43. The method of embodiment 35, wherein the heavy chain comprises the amino acid sequence of SEQ ID NO: 2 and the light chain comprises the amino acid sequence of SEQ ID NO: 1.

44. The method of any one of embodiments 35-43, wherein the patient is suffering from generalized myasthenia gravis.

45. The method of any one of embodiments 35-44, wherein the patient is an adult patient or a pediatric patient.

46. The method of any one of embodiments 35-45, wherein the administration is intravenous or subcutaneous.

47. The method of any one of embodiments 35-46, wherein the administration comprises administering a pharmaceutical composition comprising about 10 mg/ml to about 60 mg/ml of the anti-FcRn antibody, about 20 mM to about 30 mM sodium phosphate, about 20 mM to about 30 mM sodium chloride, about 80 mg/ml to about 100 mg/ml Trehalose, and about 0.1% w/v to about 0.005% w/v Polysorbate 80.

48. The method of any one of embodiments 35-47, wherein the initial loading dose is about 60 mg/kg.

49. The method of any one of embodiments 35-47, wherein the initial loading dose is about 30 mg/kg.

50. The method of any one of embodiments 35-49, wherein the maintenance dose is about 15 mg/kg, about 30 mg/kg, about 45 mg/kg, or about 60 mg/kg.

51. The method of any one of embodiments 35-50, wherein the maintenance dose is about 15 mg/kg.

52. The method of any one of embodiments 35-50, wherein the maintenance dose is about 30 mg/kg.

53. The method of any one of embodiments 35-52, wherein the maintenance dose is administered 1 week, 2 weeks, 3 weeks, or 4 weeks after the administration of the initial loading dose.

54. The method of any one of embodiments 35-53, wherein the initial loading dose is infused into the subject in about 30 minutes to about 90 minutes.

55. The method of any one of embodiments 35-54, wherein the maintenance dose is infused into the subject in about 15 minutes to about 60 minutes.

56. The method of any one of embodiments 35-55, wherein the autoantibodies are selected from the group consisting of: anti-acetylcholine receptors (AChRs), anti-muscle-specific kinase (MuSK) anti-low-density lipoprotein receptor-related protein 4 (LRP4), anti-agrin, anti-titin, anti-Kv1.4, anti-ryanodine receptors, anti-collagen Q, and anti-cortactin.

57. The method of any one of embodiments 35-56, wherein the autoantibodies are anti-AChR or anti-MuSK antibodies.

58. The method of any one of embodiments 35-57, wherein the administration of the anti-FcRn antibody reduces anti-AChR antibodies by at least 95%, at least 90%, at least 85%, at least 80%, at least 75%, at least 50%, or at least 25% of baseline anti-AChR antibodies.

59. The method of any one of embodiments 35-57, wherein the administration of the anti-FcRn antibody reduces anti-MuSK antibodies by at least 95%, at least 90%, at least 85%, at least 80%, at least 75%, at least 50%, or at least 25% of baseline anti-MuSK antibodies.

60. The method of any one of embodiments 35-59, wherein the administration reduces serum IgG by at least 10%, at least 20%, at least 30%, at least 40%, at least 50%, at least 60%, at least 70%, at least 80%, or at least 90% of baseline serum IgG.

61. The method of any one of embodiments 35-60, wherein the serum IgG is IgG1, IgG2, IgG3, or IgG4.

62. The method of any one of embodiments 35-61, wherein the administration reduces serum albumin by at most 18%, at most 16%, at most 14%, at most 12%, at most 10%, at most 8%, at most 6%, at most 4%, or at most 2% of baseline serum albumin.

63. A method of treating or reducing severity of myasthenia gravis in a subject, the method comprising administering to the subject an initial loading dose of about 30 mg/kg mg/kg to about 60 mg/kg of the anti-FcRn antibody followed by administering a maintenance dose of about 15 mg/kg to about 30 mg/kg of an anti-FcRn antibody, wherein the anti-FcRn antibody comprises:

a heavy chain comprising a HCDR1 of SEQ ID NO: 6, a HCDR2 of SEQ ID NO: 7, and a HCDR3 of SEQ ID NO: 8; and a light chain comprising a LCDR1 of SEQ ID NO: 3, a LCDR2 of SEQ ID NO: 4, and a LCDR3 of SEQ ID NO: 5.

64. The method of embodiment 63, wherein the heavy chain comprises an amino acid sequence having at least 90% identity to the sequence of SEQ ID NO: 2 and the light chain comprises an amino acid sequence having at least 90% identity to the sequence of SEQ ID NO: 1.

65. The method of embodiment 63, wherein the heavy chain comprises an amino acid sequence having at least 95% identity to the sequence of SEQ ID NO: 2 and the light chain comprises an amino acid sequence having at least 95% identity to the sequence of SEQ ID NO: 1.

66. The method of embodiment 63, wherein the heavy chain comprises an amino acid sequence having at least 99% identity to the sequence of SEQ ID NO: 2 and the light chain comprises an amino acid sequence having at least 99% identity to the sequence of SEQ ID NO: 1.

67. The method of embodiment 63, wherein the heavy chain comprises a variable region heavy chain comprising an amino acid sequence having at least 90% identity to the sequence of SEQ ID NO: 10 and the light chain comprises a variable region light chain comprising an amino acid sequence having at least 90% identity to the sequence of SEQ ID NO: 9.

68. The method of embodiment 63, wherein the heavy chain comprises a variable region heavy chain comprising an amino acid sequence having at least 95% identity to the sequence of SEQ ID NO: 10 and the light chain comprises a variable region light chain comprising an amino acid sequence having at least 95% identity to the sequence of SEQ ID NO: 9.

69. The method of embodiment 63, wherein the heavy chain comprises a variable region heavy chain comprising an amino acid sequence having at least 99% identity to the sequence of SEQ ID NO: 10 and the light chain comprises a variable region light chain comprising an amino acid sequence having at least 99% identity to the sequence of SEQ ID NO: 9.

70. The method of embodiment 63, wherein the heavy chain comprises the amino acid sequence of SEQ ID NO: 2 and the light chain comprises the amino acid sequence of SEQ ID NO: 1.

71. The method of embodiment 63, wherein the heavy chain comprises a variable region heavy chain comprising the amino acid sequence of SEQ ID NO: 10 and the light chain comprises a variable region light chain comprising the amino acid sequence of SEQ ID NO: 9.

72. The method of any one of embodiments 63-71, wherein the patient is suffering from generalized myasthenia gravis.

73. The method of any one of embodiments 63-72, wherein the patient is an adult patient or a pediatric patient.

74. The method of any one of embodiments 63-73, wherein the administration is intravenous or subcutaneous.

75. The method of any one of embodiments 63-74, wherein the administration comprises administering a pharmaceutical composition comprising about 10 mg/ml to about 60 mg/ml of the anti-FcRn antibody, about 20 mM to about 30 mM sodium phosphate, about 20 mM to about 30 mM sodium chloride, about 80 mg/ml to about 100 mg/ml Trehalose, and about 0.1% w/v to about 0.005% w/v Polysorbate 80.

76. The method of any one of embodiments 63-75, wherein the initial loading dose is about 60 mg/kg.

77. The method of any one of embodiments 63-75, wherein the initial loading dose is about 30 mg/kg.

78. The method of any one of embodiments 63-77, wherein the maintenance dose is about 15 mg/kg, about 30 mg/kg, about 45 mg/kg, or about 60 mg/kg.

79. The method of any one of embodiments 63-78, wherein the maintenance dose is about 15 mg/kg.

80. The method of any one of embodiments 63-78, wherein the maintenance dose is about 30 mg/kg.

81. The method of any one of embodiments 63-80, wherein the maintenance dose is administered 1 week, 2 weeks, 3 weeks, or 4 weeks after the administration of the initial loading dose.

82. The method of any one of embodiments 63-81, wherein the initial loading dose is infused into the subject in about 30 minutes to about 90 minutes.

83. The method of any one of embodiments 63-82, wherein the maintenance dose is infused into the subject in about 15 to about 60 minutes.

84. The method of any one of embodiments 63-83, wherein the subject shows a reduction in one or more serum immunoglobulin isotypes or total IgG.

85. The method of any one of embodiments 63-84, wherein the isotype is IgG1, IgG2, IgG3, or IgG4.

86. The method of any one of embodiments 63-85, wherein the reduction in serum IgG is at least 10%, at least 20%, at least 30%, at least 40%, at least 50%, at least 60%, at least 70%, at least 80%, or at least 90% of baseline serum IgG.

87. The method of any one of embodiments 63-86, wherein the administration reduces serum albumin by at most 18%, at most 16%, at most 14%, at most 12%, at most 10%, at most 8%, at most 6%, at most 4%, or at most 2% of baseline serum albumin.

88. The method of any one of embodiments 63-87, wherein the subject has a reduction in autoantibodies.

89. The method of any one of embodiments 63-88, wherein autoantibodies are selected from the group consisting of: anti-acetylcholine receptors (AChRs), anti-muscle-specific kinase (MuSK) anti-low-density lipoprotein receptor-related protein 4 (LRP4), anti-agrin, anti-titin, anti-Kv1.4, anti-ryanodine receptors, anti-collagen Q, and anti-cortactin.

90. The method of any one of embodiments 63-89, wherein the autoantibodies are anti-AChR or anti-MuSK antibodies.

91. The method of any one of embodiments 63-90, wherein the administration of the anti-FcRn antibody reduces anti-AChR antibodies by at least 95%, at least 90%, at least 85%, at least 80%, at least 75%, at least 50%, or at least 25% of baseline anti-AChR antibodies.

92. The method of any one of embodiments 63-90, wherein the administration of the anti-FcRn antibody reduces anti-MuSK antibodies by at least 95%, at least 90%, at least 85%, at least 80%, at least 75%, at least 50%, or at least 25% of baseline anti-MuSK antibodies.

93. The method of any one of embodiments 63-92, wherein the treatment of myasthenia gravis treats or ameliorates ocular myasthenia, ptosis, difficulty chewing, dysphagia, dysarthria, hypophonia, dyspnea, an inability to hold the mouth closed, an appearance of sadness or sleepiness, difficulty holding the head upright, diplopia, dysarthria, difficulty swallowing, change in facial expression, shortness of breath, weakness in arms, weakness in hands, weakness in fingers, weakness in legs, weakness in neck.

93. The method of any one of embodiments 63-92, wherein the patient achieves a change from baseline in MG-ADL, QMG, or MG-QoL15 scale, Neuro-QoL-Fatigue score, EQ-5D-5L score, MGFA score, PGI-C score, PGI-S score, C-SSRS score, and PedsQL score.

94. The method of any one of embodiments 63-93, wherein the patient achieves a change from baseline on MG-ADL scale.

95. The method of any one of embodiments 63-94, wherein the patient achieves a change from baseline on MG-ADL scale that is greater than or equal to 2.0 points on MG-ADL scale.

96. The method of any one of embodiments 63-95, wherein the patient achieves a change from baseline on MG-ADL scale that is greater than or equal to 3.0 points on MG-ADL scale.

97. The method of any one of embodiments 63-96, wherein the change form baseline on MG-ADL scale persists for at least 4 weeks.

98. The method of any one of embodiments 63-97, wherein the patient achieves a change from baseline on QMG scale.

99. The method of any one of embodiments 63-98, wherein the patient achieves a change from baseline on QMG scale that is at least a 2, 3, 4, 5, 6, 7, or greater than or equal to 8 point reduction in QMG score.

100. The method of any one of embodiments 63-99, wherein the patient achieves a change from baseline on QMG scale that is at least a 3 point reduction in QMG score.

101. The method of any one of embodiments 63-99, wherein the patient achieves a change from baseline on QMG scale that is at least a 4 point reduction in QMG score.

102. The method of any one of embodiments 63-99, wherein the patient achieves a change from baseline on QMG scale that is at least a 5 point reduction in QMG score.

103. The method of any one of embodiments 63-102, wherein the patient achieves a change from baseline on MG-QoL-15r scale.

104. The method of any one of embodiments 63-103, wherein the patient achieves a change from baseline on MG-QoL-15r scale that is at least a 3, 4, 5, or 6 point reduction in MG-QoL-15r score.

105. The method of any one of embodiments 63-104, wherein the patient achieves a change from baseline on MG-QoL-15r scale that is at least a 3 point reduction in MG-QoL-15r score.

106. The method of any one of embodiments 63-104, wherein the patient achieves a change from baseline on MG-QoL-15r scale that is at least a 6 point reduction in MG-QoL-15r score.

107. The method of any one of embodiments 63-106, wherein the patient achieves a change from baseline in MGFA classification.

108. The method of any one of embodiments 63-107, wherein the change from baseline in MGFA classification indicates improvement.

109. The method of any one of embodiments 63-108, wherein the patient achieves a change from baseline on Neuro-QoL-Fatigue scale after 22, 23, and 24 weeks following treatment.

110. The method of any one of embodiments 63-109, wherein the change from baseline on Neuro-QoL-Fatigue scale indicates improvement.

111. The method of any one of embodiments 63-110, wherein the patient achieves a change from baseline on EQ-5D-5L scale after 22, 23, and 24 weeks following treatment.

112. The method of any one of embodiments 63-111, wherein the change from baseline on EQ-5D-5L scale indicates improvement.

113. The method of any one of embodiments 63-112, wherein the patient achieves a change from baseline on PGI-C scale after 22, 23, and 24 weeks following treatment.

114. The method of any one of embodiments 63-113, wherein the change from baseline on PGI-C scale indicates improvement.

115. The method of any one of embodiments 63-114, wherein the patient achieves a change from baseline on PGI-S scale after 22, 23, and 24 weeks following treatment.

116. The method of any one of embodiments 63-115, wherein the change from baseline on PGI-S scale indicates improvement.

117. The method of any one of embodiments 63-116, wherein the patient achieves a change from baseline on C-SSRS after 22, 23, and 24 weeks following treatment.

118. The method of any one of embodiments 63-117, wherein the change from baseline on C-SSRS scale indicates improvement.

119. The method of any one of embodiments 63-118, wherein the pediatric patient achieves a change from baseline on PedsQL scale after treatment.

120. The method of any one of embodiments 63-119, wherein the change form baseline on PedsQL scale indicates improvement.

121. The method of any one of embodiments 63-120, wherein the administration of the anti-FcRn antibody to the subject does not significantly increase levels of total cholesterol, HDL, calculated LDL, and triglycerides in the subject as compared to the levels prior to the administration of the anti-FcRn antibody.

122. The method of embodiment 121, wherein the administration does not significantly increase levels of total cholesterol.

123. The method of embodiment 121, wherein the administration does not significantly increase levels of total HDL.

124. The method of embodiment 121, wherein the administration does not significantly increase levels of calculated LDL.

125. The method of embodiment 121, wherein the administration does not significantly increase levels of triglycerides.

126. The method of any one of embodiments 121-125, wherein the method further comprises administering an additional therapeutic to the subject.

127. The method of any one of embodiments 63-126, wherein the additional therapeutic is a acetylcholinesterase inhibitor, pyridostigmine, pyridostigmine bromide (Mestinon), neostigmine, prednisone, azathioprine (Imuran), mycophenylate mofetil (CellCept), tacrolimus (Prograf), methotrexate, cyclosporine (Sandimmune, Neoral), and cyclophosphamide (Cytoxan, Neosar), rituximab (Rituxan), eculizumab (Soliris), IVIg, or any combination thereof.

128. The method of any one of embodiments 63-127, wherein the additional therapeutic is administered concurrently or sequentially (prior to or after) with the anti-FcRn antibody.

129. A pharmaceutical composition comprising an anti-FcRn antibody for administration to a patient suffering from myasthenia gravis, wherein:

the anti-FcRn antibody is administered to the patient at an initial loading dose of about 30 mg/kg mg/kg to about 60 mg/kg followed by administering a maintenance dose of about 15 mg/kg to about 30 mg/kg of the anti-FcRn antibody; and the anti-FcRn antibody comprises:

a heavy chain comprising a HCDR1 of SEQ ID NO: 6, a HCDR2 of SEQ ID NO: 7, and a HCDR3 of SEQ ID NO: 8; and a light chain comprising a LCDR1 of SEQ ID NO: 3, a LCDR2 of SEQ ID NO: 4, and a LCDR3 of SEQ ID NO: 5.

130. The pharmaceutical composition of embodiment 129, wherein the heavy chain comprises an amino acid sequence having at least 90% identity to the sequence of SEQ ID NO: 2 and the light chain comprises an amino acid sequence having at least 90% identity to the sequence of SEQ ID NO: 1.

131. The pharmaceutical composition of embodiment 129, wherein the heavy chain comprises an amino acid sequence having at least 95% identity to the sequence of SEQ ID NO: 2 and the light chain comprises an amino acid sequence having at least 95% identity to the sequence of SEQ ID NO: 1.

132. The pharmaceutical composition of embodiment 129, wherein the heavy chain comprises an amino acid sequence having at least 99% identity to the sequence of SEQ ID NO: 2 and the light chain comprises an amino acid sequence having at least 99% identity to the sequence of SEQ ID NO: 1.

133. The pharmaceutical composition of embodiment 129, wherein the heavy chain comprises a variable region heavy chain comprising an amino acid sequence having at least 90% identity to the sequence of SEQ ID NO: 10 and the light chain comprises a variable region light chain comprising an amino acid sequence having at least 90% identity to the sequence of SEQ ID NO: 9.

134. The pharmaceutical composition of embodiment 129, wherein the heavy chain comprises a variable region heavy chain comprising an amino acid sequence having at least 95% identity to the sequence of SEQ ID NO: 10 and the light chain comprises a variable region light chain comprising an amino acid sequence having at least 95% identity to the sequence of SEQ ID NO: 9.

135. The pharmaceutical composition of embodiment 129, wherein the heavy chain comprises a variable region heavy chain comprising an amino acid sequence having at least 99% identity to the sequence of SEQ ID NO: 10 and the light chain comprises a variable region light chain comprising an amino acid sequence having at least 99% identity to the sequence of SEQ ID NO: 9.

136. The pharmaceutical composition of embodiment 129, wherein the heavy chain comprises the amino acid sequence of SEQ ID NO: 2 and the light chain comprises the amino acid sequence of SEQ ID NO: 1.

137. The pharmaceutical composition of embodiment 129, wherein the heavy chain comprises a variable region heavy chain comprising the amino acid sequence of SEQ ID NO: 10 the light chain comprises a variable region light chain comprising the amino acid sequence of SEQ ID NO: 9.

138. The pharmaceutical composition of any one of embodiments 129-137, wherein the patient is suffering from generalized myasthenia gravis.

139. The pharmaceutical composition of any one of embodiments 129-138, wherein the patient is and adult patient or a pediatric patient.

140. The pharmaceutical composition of any one of embodiments 129-139, wherein the administration is intravenous or subcutaneous.

141. The pharmaceutical composition of any one of embodiments 129-140, wherein the administration comprises administering a pharmaceutical composition comprising about 10 mg/ml to about 60 mg/ml of the anti-FcRn antibody, about 20 mM to about 30 mM sodium phosphate, about 20 mM to about 30 mM sodium chloride, about 80 mg/ml to about 100 mg/ml Trehalose, and about 0.1% w/v to about 0.005% w/v Polysorbate 80.

142. The pharmaceutical composition of any one of embodiments 129-141, wherein the initial loading dose is about 60 mg/kg.

143. The pharmaceutical composition of any one of embodiments 129-142, wherein the initial loading dose is about 30 mg/kg.

144. The pharmaceutical composition of any one of embodiments 129-143, wherein the maintenance dose is about 15 mg/kg, about 30 mg/kg, about 45 mg/kg, or about 60 mg/kg.

145. The pharmaceutical composition of any one of embodiments 129-144, wherein the maintenance dose is about 15 mg/kg.

146. The pharmaceutical composition of any one of embodiments 129-144, wherein the maintenance dose is about 30 mg/kg.

147. The pharmaceutical composition of any one of embodiments 129-146, wherein the administering of the maintenance dose occurs 1 week, 2 weeks, 3 weeks, or 4 weeks after the administration of the initial loading dose.

148. The pharmaceutical composition of any one of embodiments 129-147, wherein the initial loading dose is infused into the subject in about 30 minutes to about 90 minutes.

149. The pharmaceutical composition of any one of embodiments 129-148, wherein the maintenance dose is infused into the subject in about 15 minutes to about 60 minutes.

150. The pharmaceutical composition of any one of embodiments 129-149, wherein the administration of the pharmaceutical composition achieves a reduction in one or more serum immunoglobulin isotypes or total IgG.

151. The pharmaceutical composition of any one of embodiments 129-150, wherein the isotype is IgG1, IgG2, IgG3, or IgG4.

152. The pharmaceutical composition of any one of embodiments 129-151, wherein the reduction in serum IgG is at least 10%, at least 20%, at least 30%, at least 40%, at least 50%, at least 60%, at least 70%, at least 80%, or at least 90% of baseline.

153. The pharmaceutical composition of any one of embodiments 129-152, wherein the administration of the pharmaceutical composition achieves a reduction in serum albumin by at most 18%, at most 16%, at most 14%, at most 12%, at most 10%, at most 8%, at most 6%, at most 4%, or at most 2% of baseline serum albumin.

154. The pharmaceutical composition of any one of embodiments 129-153, wherein the administration of the pharmaceutical composition achieves a reduction in autoantibodies.

155. The pharmaceutical composition of any one of embodiments 129-154, wherein autoantibodies are selected from the group consisting of: anti-acetylcholine receptors (AChRs), anti-muscle-specific kinase (MuSK) anti-low-density lipoprotein receptor-related protein 4 (LRP4), anti-agrin, anti-titin, anti-Kv1.4, anti-ryanodine receptors, anti-collagen Q, and anti-cortactin.

156. The pharmaceutical composition of any one of embodiments 129-155, wherein the autoantibodies are anti-AChR or anti-MuSK antibodies.

157. The pharmaceutical composition of any one of embodiments 129-156, wherein the administration of the pharmaceutical composition achieves a reduction of anti-AChR antibodies by at least 95%, at least 90%, at least 85%, at least 80%, at least 75%, at least 50%, or at least 25% of baseline.

158. The pharmaceutical composition of any one of embodiments 129-156, wherein the administration of the pharmaceutical composition achieves a reduction of anti-MuSK antibodies by at least 95%, at least 90%, at least 85%, at least 80%, at least 75%, at least 50%, or at least 25% of baseline.

159. The pharmaceutical composition of any one of embodiments 129-158, wherein the administration of the pharmaceutical composition achieves a change from baseline in MG-ADL, QMG, or MG-QoL15 scale, Neuro-QoL-Fatigue score, EQ-5D-5L score, MGFA score, PGI-C score, PGI-S score, C-SSRS score, and PedsQL score.

160. The pharmaceutical composition of any one of embodiments 129-159, wherein the administration of the pharmaceutical composition achieves a change from baseline on MG-ADL scale.

161. The pharmaceutical composition of any one of embodiments 129-160, wherein the administration of the pharmaceutical composition achieves a change from baseline on MG-ADL scale that is greater than or equal to 2.0 points on MG-ADL scale.

162. The pharmaceutical composition of any one of embodiments 129-160, wherein the administration of the pharmaceutical composition achieves a change from baseline on MG-ADL scale that is greater than or equal to 3.0 points on MG-ADL scale.

163. The pharmaceutical composition of any one of embodiments 129-162, wherein the change form baseline on MG-ADL scale persists for at least 4 weeks.

164. The pharmaceutical composition of any one of embodiments 129-163, wherein the administration of the pharmaceutical composition achieves a change from baseline on QMG scale.

165. The pharmaceutical composition of any one of embodiments 129-164, wherein the administration of the pharmaceutical composition achieves a change from baseline on QMG scale that is at least a 2, 3, 4, 5, 6, 7, or greater than or equal to 8 point reduction in QMG score.

166. The pharmaceutical composition of any one of embodiments 129-165, wherein the administration of the pharmaceutical composition achieves a change from baseline on QMG scale that is at least a 3 point reduction in QMG score.

167. The pharmaceutical composition of any one of embodiments 129-165, wherein the administration of the pharmaceutical composition achieves a change from baseline on QMG scale that is at least a 4 point reduction in QMG score.

168. The pharmaceutical composition of any one of embodiments 129-165, wherein the administration of the pharmaceutical composition achieves a change from baseline on QMG scale that is at least a 5 point reduction in QMG score.

169. The pharmaceutical composition of any one of embodiments 129-168, wherein the administration of the pharmaceutical composition achieves a change from baseline on MG-QoL15 scale.

170. The pharmaceutical composition of any one of embodiments 129-169, wherein the administration of the pharmaceutical composition achieves a change from baseline on MG-QoL-15r scale that is at least a 3, 4, 5, or 6 point reduction in MG-QoL-15r score.

171. The pharmaceutical composition of any one of embodiments 129-170, wherein the administration of the pharmaceutical composition achieves a change from baseline on MG-QoL-15r scale that is at least a 3 point reduction in MG-QoL-15r score.

172. The pharmaceutical composition of any one of embodiments 129-170, wherein the administration of the pharmaceutical composition achieves a change from baseline on MG-QoL-15r scale that is at least a 6 point reduction in MG-QoL-15r score.

173. The pharmaceutical composition of any one of embodiments 129-172, wherein the administration of the pharmaceutical composition achieves a change from baseline in MGFA classification.

174. The pharmaceutical composition of any one of embodiments 129-173, wherein the change from baseline in MGFA classification indicates improvement.

175. The pharmaceutical composition of any one of embodiments 129-174, wherein the administration of the pharmaceutical composition achieves a change from baseline on Neuro-QoL-Fatigue scale after 22, 23, and 24 weeks following treatment.

176. The pharmaceutical composition of any one of embodiments 129-175, wherein the change from baseline on Neuro-QoL-Fatigue scale indicates improvement.

177. The pharmaceutical composition of any one of embodiments 129-176, wherein the administration of the pharmaceutical composition achieves a change from baseline on EQ-5D-5L scale after 22, 23, and 24 weeks following treatment.

178. The pharmaceutical composition of any one of embodiments 129-177, wherein the change from baseline on EQ-5D-5L scale indicates improvement.

179. The pharmaceutical composition of any one of embodiments 129-178, wherein the administration of the pharmaceutical composition achieves a change from baseline on PGI-C scale after 22, 23, and 24 weeks following treatment.

180. The pharmaceutical composition of any one of embodiments 129-179, wherein the change from baseline on PGI-C scale indicates improvement.

181. The pharmaceutical composition of any one of embodiments 129-180, wherein the administration of the pharmaceutical composition achieves a change from baseline on PGI-S scale after 22, 23, and 24 weeks following treatment.

182. The pharmaceutical composition of any one of embodiments 129-181, wherein the change from baseline on PGI-S scale indicates improvement.

183. The pharmaceutical composition of any one of embodiments 129-182, wherein the administration of the pharmaceutical composition achieves a change from baseline on C-SSRS after 22, 23, and 24 weeks following treatment.

184. The pharmaceutical composition of any one of embodiments 129-183, wherein the change from baseline on C-SSRS scale indicates improvement.

185. The pharmaceutical composition of any one of embodiments 129-184, wherein the administration of the pharmaceutical composition achieves a change from baseline on PedsQL scale following treatment.

186. The pharmaceutical composition of any one of embodiments 129-185, wherein the change form baseline on PedsQL scale indicates improvement.

187. The pharmaceutical composition of any one of embodiments 129-186, wherein the administration of the pharmaceutical composition to the subject does not significantly increase levels of total cholesterol, HDL, calculated LDL, and triglycerides in the subject as compared to the levels prior to the administration of the pharmaceutical composition.

188. The pharmaceutical composition of embodiment 187, wherein the administration does not significantly increase levels of total cholesterol.

189. The pharmaceutical composition of embodiment 187, wherein the administration does not significantly increase levels of total HDL.

190. The pharmaceutical composition of embodiment 187, wherein the administration does not significantly increase levels of calculated LDL.

191. The pharmaceutical composition of embodiment 187, wherein the administration does not significantly increase levels of triglycerides.

192. The pharmaceutical composition of embodiment 129-191, wherein the pharmaceutical composition is co-administered with at least one additional therapeutic.

193. The pharmaceutical composition of any one of embodiments 129-192, wherein the at least one additional therapeutic is a acetylcholinesterase inhibitor, pyridostigmine, pyridostigmine bromide (Mestinon), neostigmine, prednisone, azathioprine (Imuran), mycophenylate mofetil (Cell-Cept), tacrolimus (Prograf), methotrexate, cyclosporine (Sandimmune, Neoral), and cyclophosphamide (Cytoxan, Neosar), rituximab (Rituxan), eculizumab (Soliris), IVIg, or any combination thereof.

194. The pharmaceutical composition of any one of embodiments 129-193, wherein the at least one additional therapeutic is administered concurrently or sequentially (prior to or after) with the anti-FcRn antibody.

EXAMPLES

The various FcRn antibodies described herein and their properties are described in detail in WO 2019/118791 (PCT/US2018/065568). The examples below used nipocalimab (also referred to as M281) as anti-FcRn antibody (amino acid sequences of light and heavy chains respectively provided by SEQ ID NOs: 1 and 2 herein).

Example 1. Pharmacokinetics and Pharmacodynamics Data for M281

Figure 2:
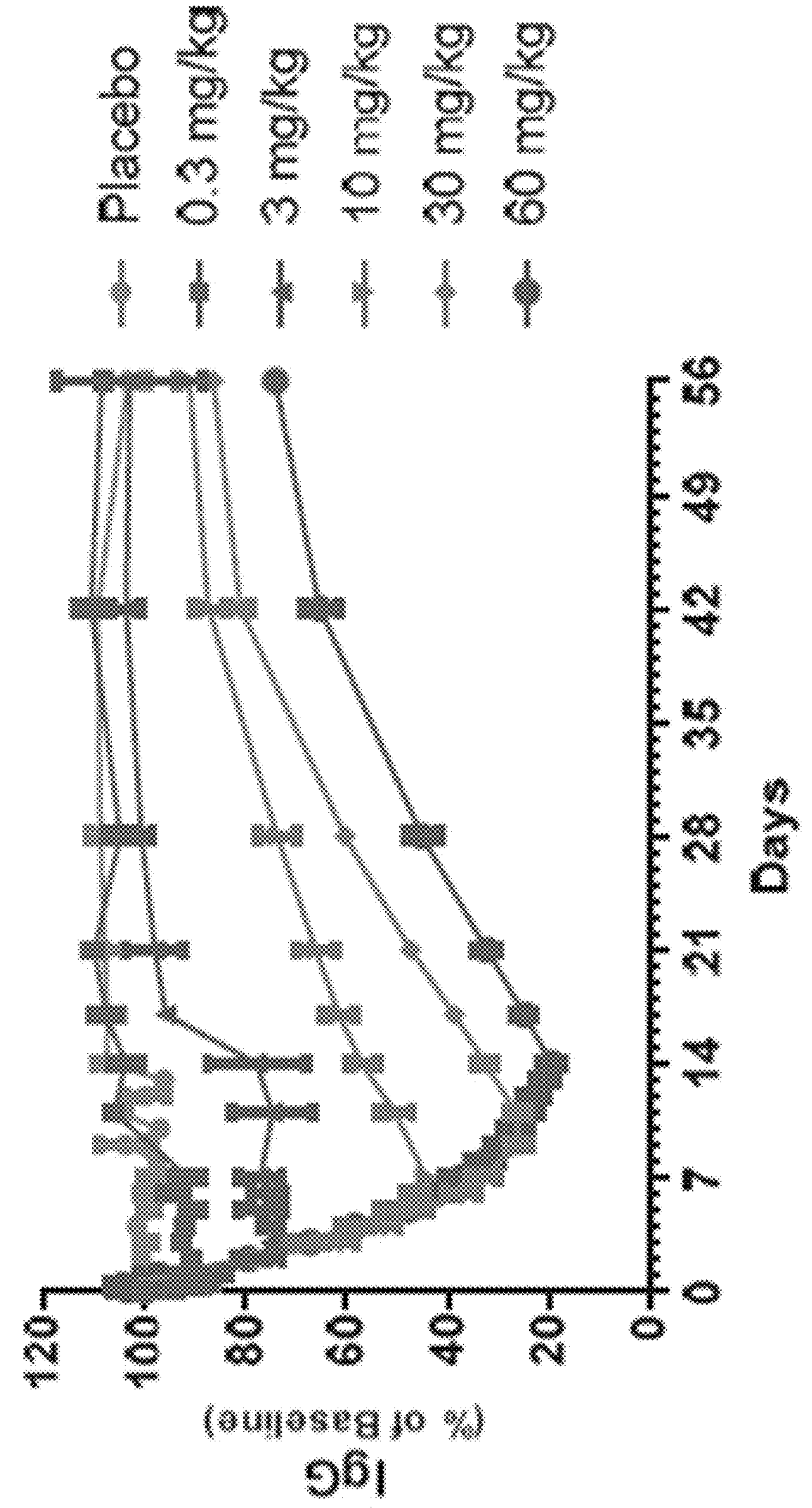
FIG. 2 is a graph showing mean (SD) serum IgG levels following single doses of 0.3 mg/kg, 3 mg/kg, 10 mg/kg, 30 mg/kg, and 60 mg/kg M281.
Figure 3A:
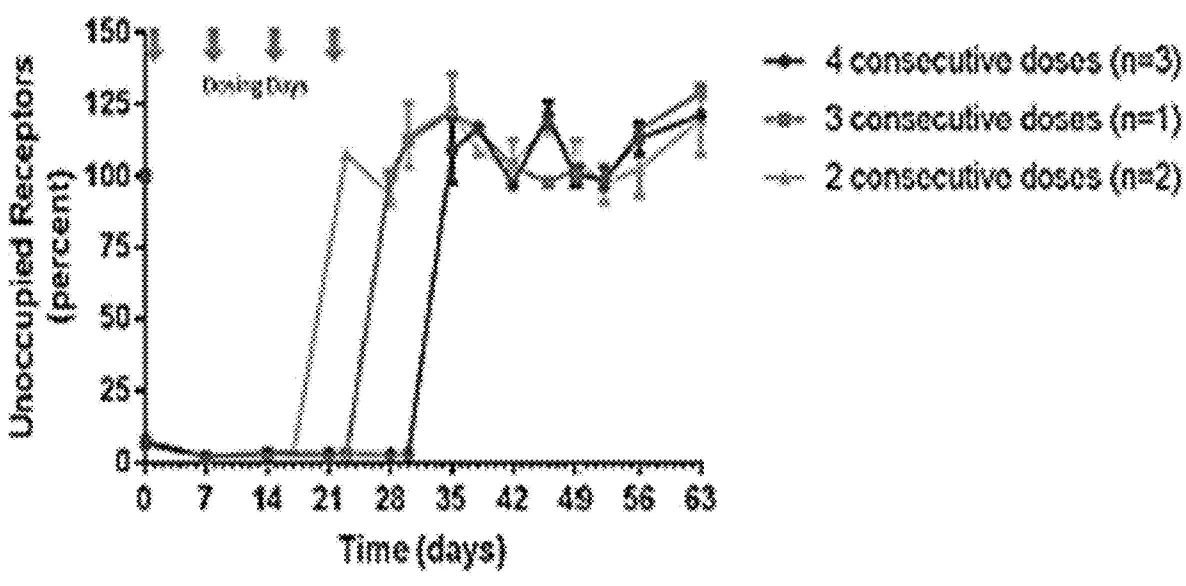
FIGS. 3A and 3B are graphs showing mean (SD) FcRn receptor occupancy in monocytes in the 30 mg/kg (FIG. 3A) and 15 mg/kg (FIG. 3B) MAD cohorts by number of doses given.
Figure 3B:
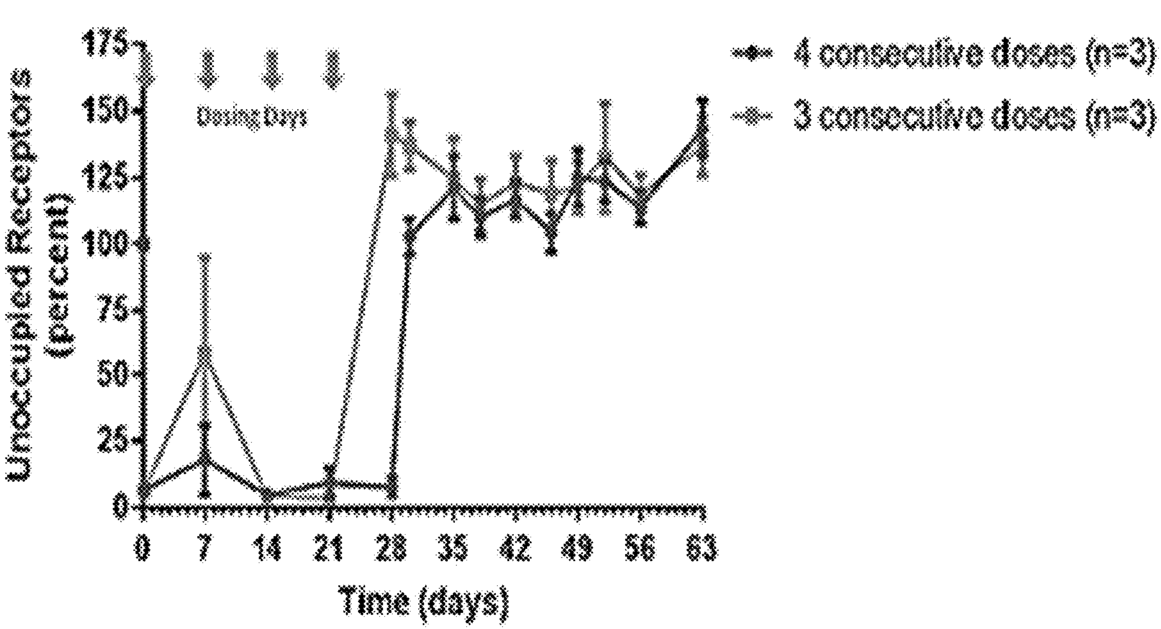

A Phase 1, single-center, randomized, double-blind placebo-controlled single ascending dose (SAD) and multiple ascending dose (MAD) (SAD/MAD) study in normal healthy volunteers (NHV) was conducted to evaluate the safety, tolerability, pharmacokinetics (PK), and pharmacodynamics (PD) of M281. In the SAD study, 5 cohorts received single intravenous infusions of placebo (n=2/cohort) or escalating doses of M281 at 0.3 (n=3), 3 (n=3), 10 (n=6), 30 (n=6), or 60 (n=6) mg/kg and were followed for safety, PK, and PD for 8 weeks. FcRn receptor occupancy (FIG. 1) and IgG level (FIG. 2) were measured In the MAD part of the study, subjects received up to 4 weekly intravenous infusions of M281 or placebo and were followed for safety, PK, and PD for 10 weeks post last dose. Subjects in the first cohort received 30 mg/kg M281 or placebo. The results indicated that complete FcRn receptor occupancy (RO) was achieved and maintained at 30 mg/kg (FIG. 3A). A second cohort of subjects was enrolled to receive 15 mg/kg M281 (or placebo) and it was determined complete RO was not maintained 15 mg/kg (FIG. 3B).

Mean serum M281 concentration data (Day 1 Cmax and trough) for subjects in the 30 and 15 mg/kg cohorts were measured. At 30 mg/kg M281, the 2-hour (Cmax) values following the first dose were within the expected range (based on SAD data) of 500-700 μg/mL and trough values on Days 7, 14, and 21 ranged from 40-140 μg/mL. With repeat dosing, group variability reduced as a steady state was established between 100-200 ug/mL. At 15 mg/kg M281, the 2-hour (Cmax) values following the first dose were between 200-400 ug/mL, and considerable variability in trough concentrations was observed, with the majority of the data falling below 10 μg/mL, providing a potential explanation for the inability to maintain complete RO was not maintained 15 mg/kg.

Figure 4A:
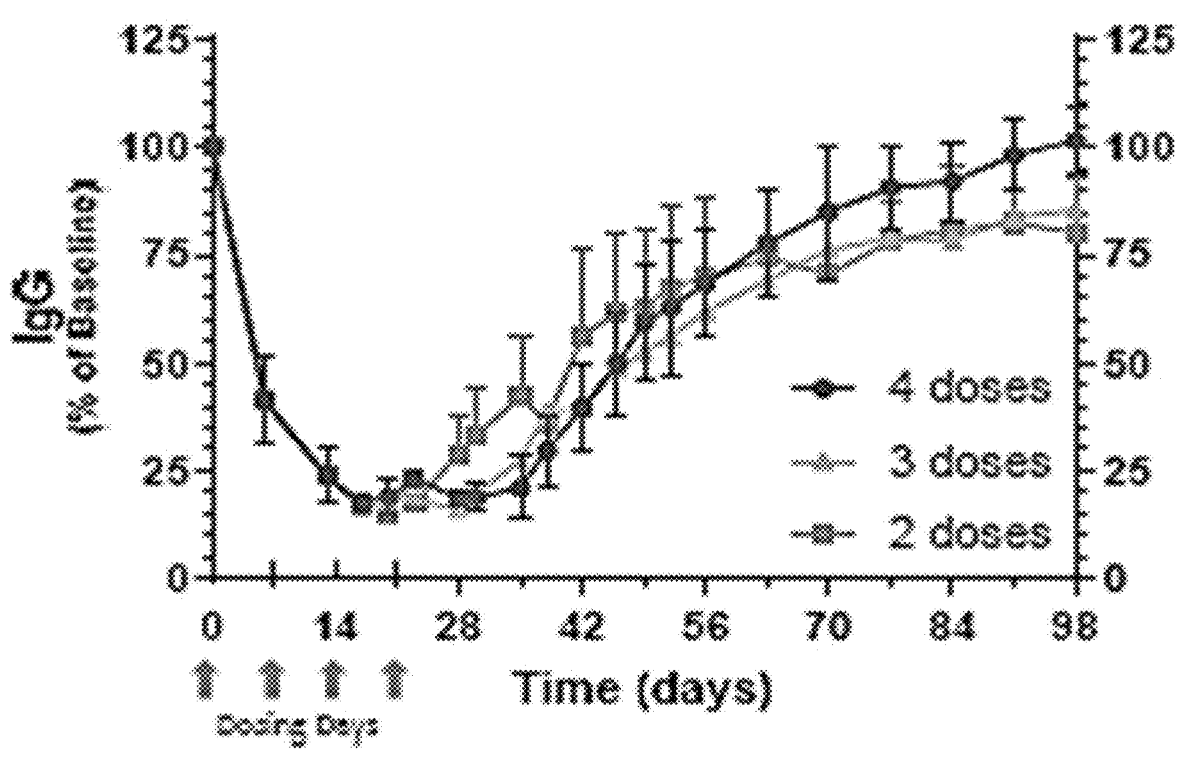
FIGS. 4A and 4B are graphs showing mean (SD) serum IgG in the 30 mg/kg (FIG. 4A) and 15 mg/kg (FIG. 4B) MAD cohorts by number of doses given.
Figure 4B:
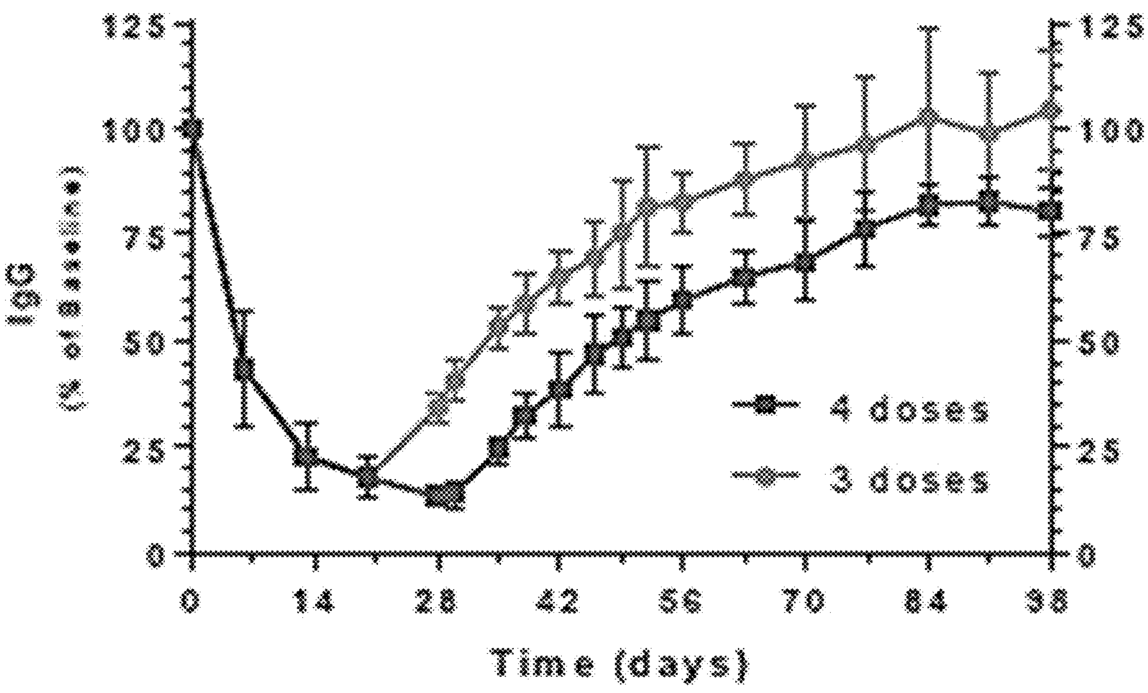

At both dose levels, serum IgG was suppressed to a similar degree during the period of dosing (FIGS. 4A and 4B).

Both the 15 mg/kg dose and the 30 mg/kg dose were safe and well-tolerated in this Phase I study.

Example 2. Safety and Tolerability of Intravenous Infusion of an Anti-FcRn Antibody A single-dose, sequential, randomized, double-blind (Sponsor-open), placebo-controlled, escalating dose and escalating infusion rate study of M281 was conducted. Healthy subjects were randomized to receive a single dose of 30 or 60 mg/kg antibody or placebo by intravenous infusion on Day 1. Each of five cohorts consisted of six subjects receiving antibody and two subjects receiving placebo for a total of 40 subjects. The five cohorts were: 30 mg/kg antibody administered over 60 minutes (6 subjects) or placebo (2 subjects); 30 mg/kg antibody administered over 30 minutes (6 subjects) or placebo (2 subjects); 30 mg/kg antibody administered over 15 minutes (6 subjects) or placebo (2 subjects); 30 mg/kg antibody administered over 7.5 minutes (6 subjects) or placebo (2 subjects); and 60 mg/kg antibody administered over 15 minutes (6 subjects) or placebo (2 subjects). The concentration of the antibody in the intravenous infusion was 30 mg/ml.

There were no deaths, serious adverse events (SAEs) or adverse events leading to subject withdrawal from the study. The most commonly reported treatment emergent adverse events were: headache, reported by 6 (20%) subjects in the active treatment groups and 1 (10%) subject receiving placebo and nausea, reported by 3 (10%) subjects receiving active treatment. Both 30 mg/kg infused in 7.5 min and 60 mg/kg infused in 15 min, although tolerated appeared to have higher rates of headache and nausea than at lower infusion rates.

Example 3. Modeling of Intravenous Dosing

Figure 5A:
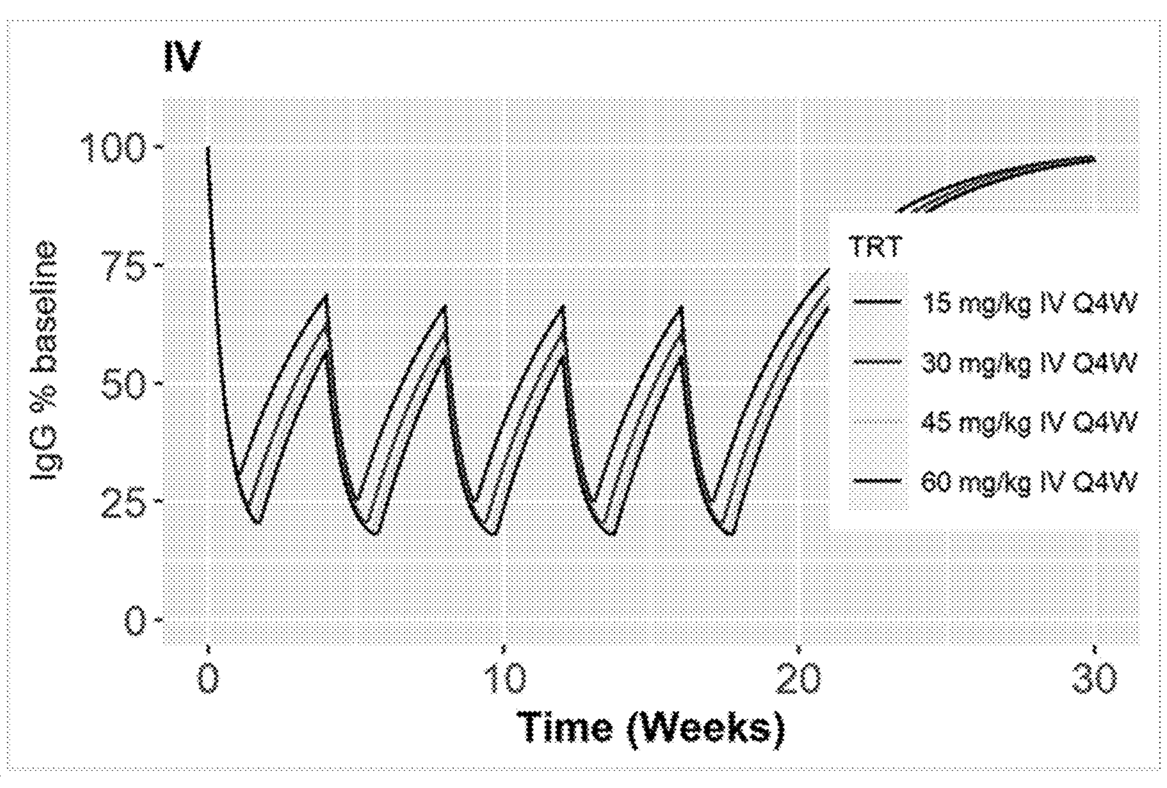
FIGS. 5A and 5B are graphs showing the results of modeling designed to predict the impact of various doses of M281 at Q4W (FIG. 5A) or Q2W (FIG. 5B) on serum IgG.
Figure 5B:
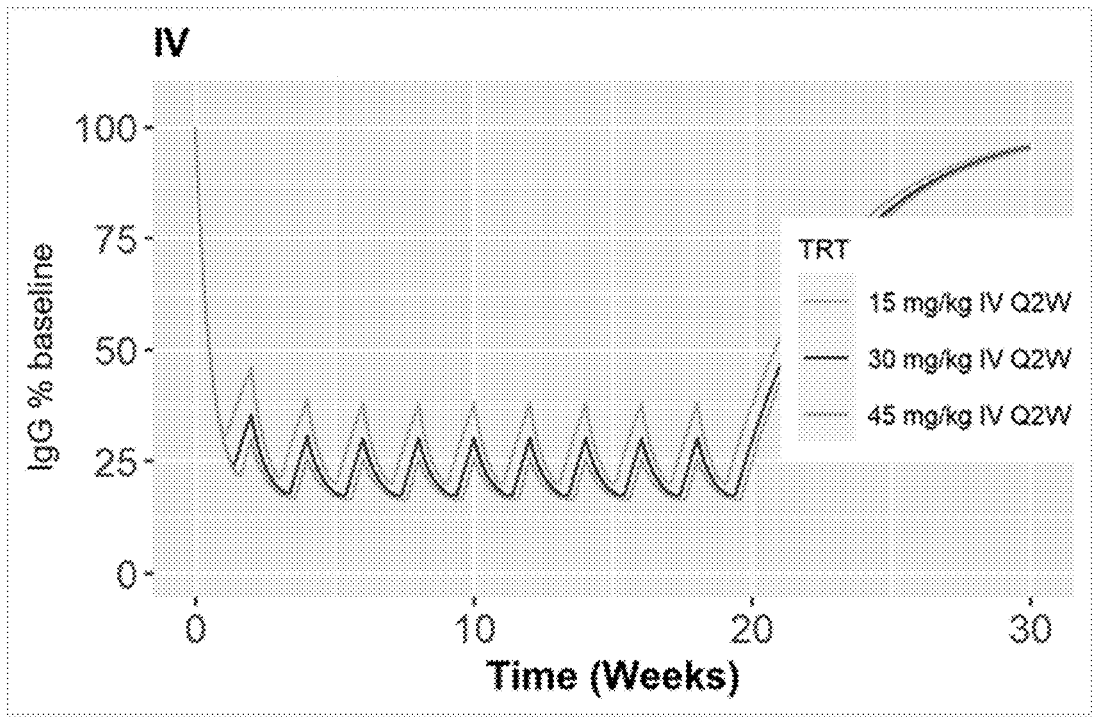

Various dosing regimens for M281 were modeled based on clinical data. First, the impact of 15, 30, 45 and 60 mg/kg IV every 4 weeks (Q4W) and 15, 30 and 35 mg/kg IV every 2 weeks (Q2W) on reduction in baseline IgG were modeled. The results of this analysis are shown in FIG. 5A and FIG. 5B. Based on this modeling, the Q2W regimen provides more sustained and overall stronger IgG reduction (30 mg/kg Q4W: mean IgG reduction ~50-60% (~40-80%) and 30 mg/kg Q2W mean IgG reduction ~79% (74-85%)).

Figure 6:
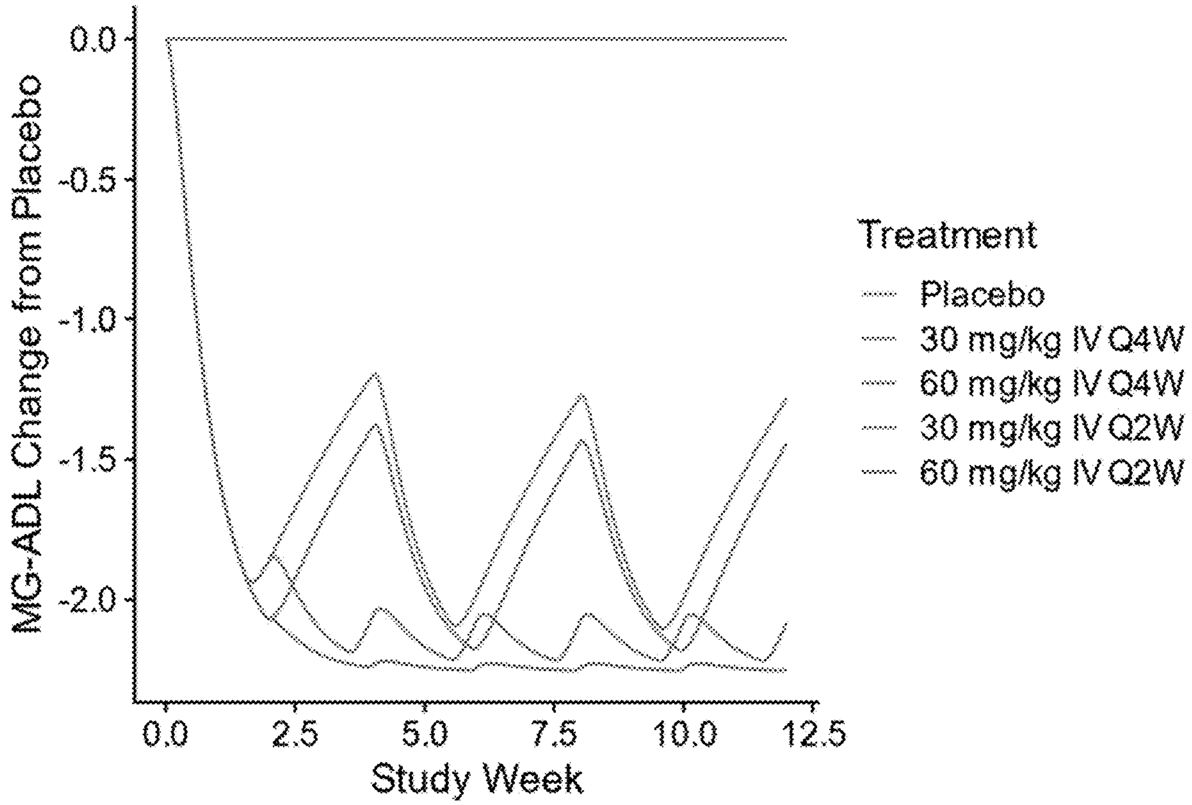
FIG. 6 is a graph showing the results of modeling designed to predict the impact of various doses of M281 on MG-ADL compared to placebo.

The impact of various dosing regimens on Myasthenia Gravis Activities of Daily Living (MG-ADL) was modeled. Among the doses modeled were: 30 mg/kg Q2W, 30 mg/kg Q4W, 60 mg/kg Q2W and 60 mg/kg Q4W. As shown in FIG. 6, based on this modeling, the dosing interval is expected to have greater impact than the dose amount.

Figure 7A:
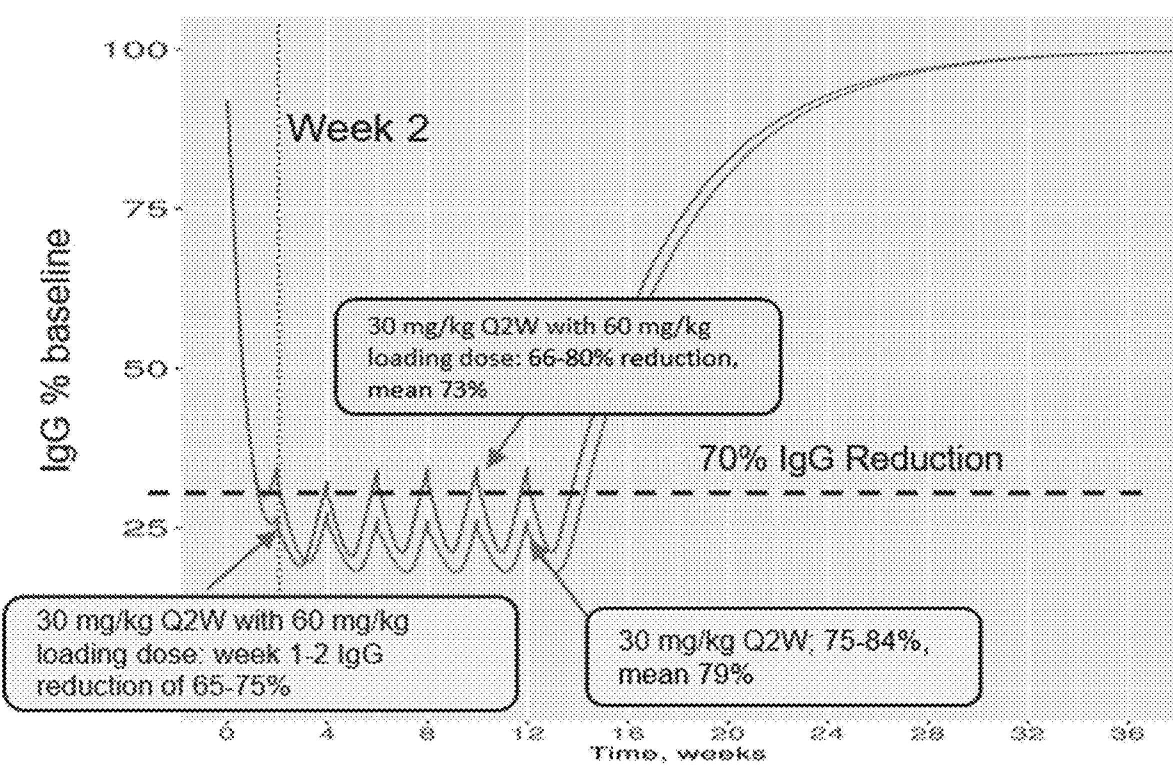
FIGS. 7A and 7B are graphs showing the results of modeling designed to predict the impact of various doses of M281 on serum IgG (FIG. 7A) and MG-ADL compared to placebo (FIG. 7B).
Figure 7B:
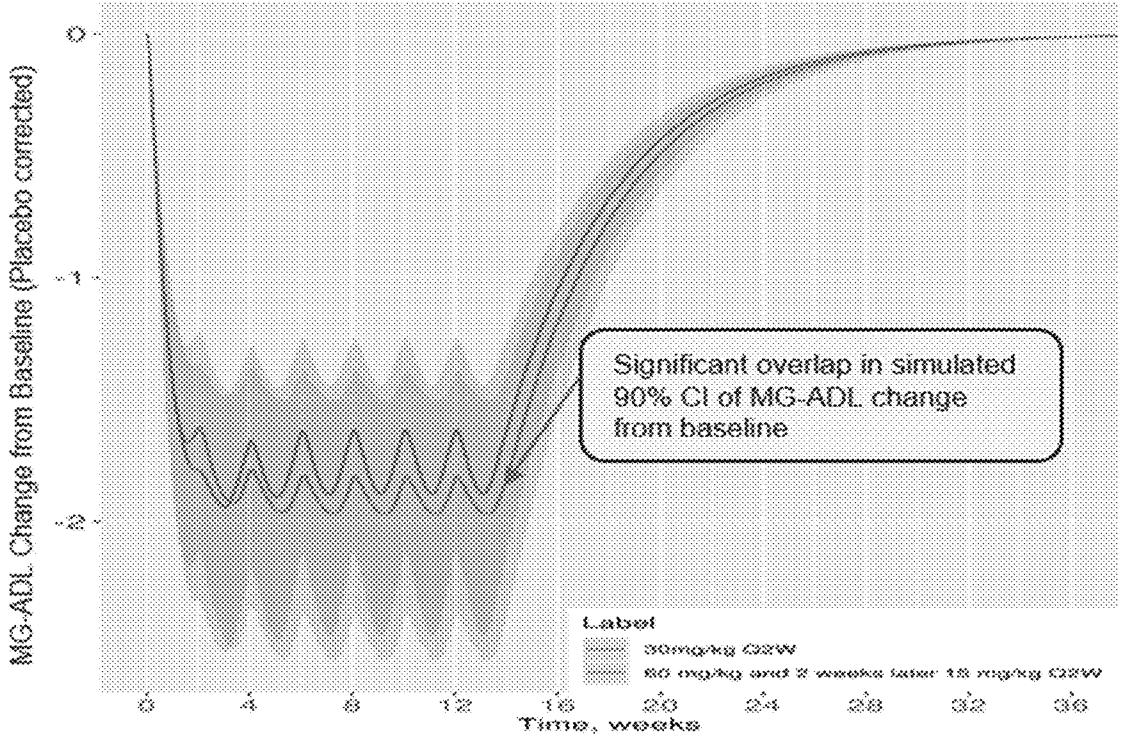
Figures 8A, 8B:
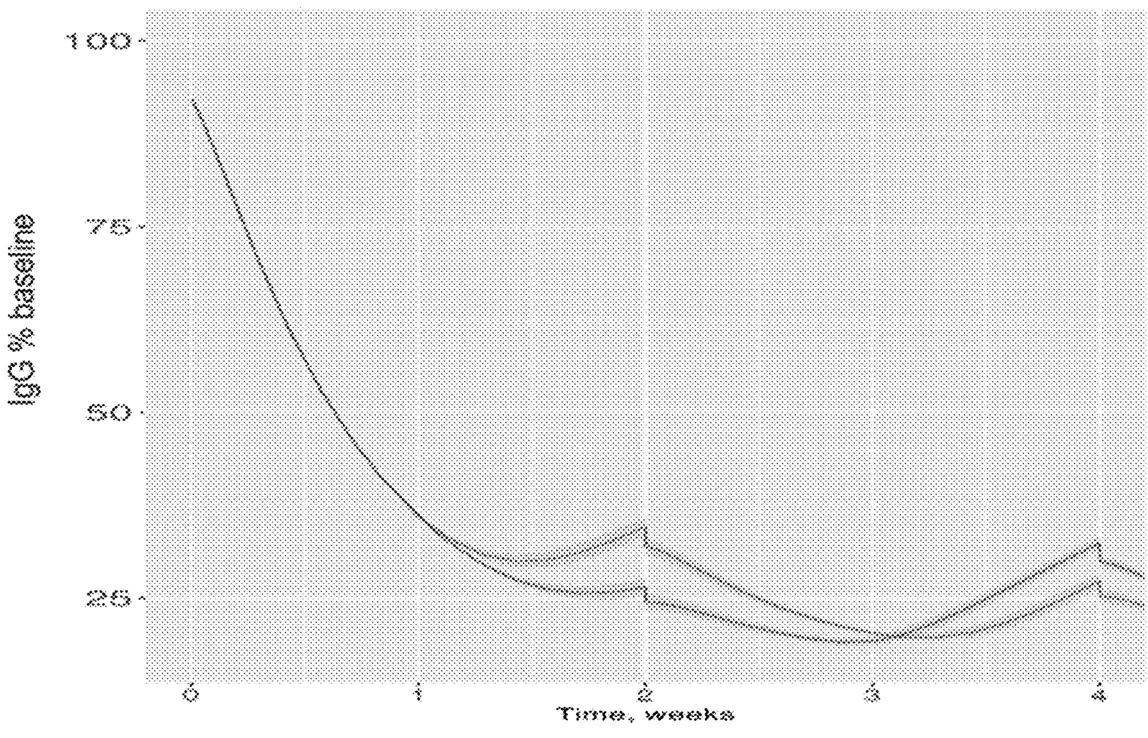
FIGS. 8A and 8B are enlargements of the Weeks 1-4 portion of the graphs in FIGS. 7A and 7B showing the results of modeling designed to predict the impact of various doses of M281 on serum IgG (FIG. 8A) and MG-ADL compared to placebo (FIG. 8B).

Next, the impact of an IV 60 mg/kg initial (loading) dose followed two weeks later by 15 mg/kg IV Q2W or 30 mg/kg IV Q2W on IgG reduction and change in MG-ADL from baseline was modeled. As shown in FIG. 7A and FIG. 7B, the inclusion of a 60 mg/kg loading dose provides superior IgG reduction in Week 1 and Week 2. This suggests the potential for earlier efficacy. FIG. 8A and FIG. 8B is a close up view of the modeling result in FIG. 7A and FIG. 7B for Week 1 and Week 2 showing that the inclusion of loading dose is expected to provide superior results during Weeks 1-2.

Figure 9:
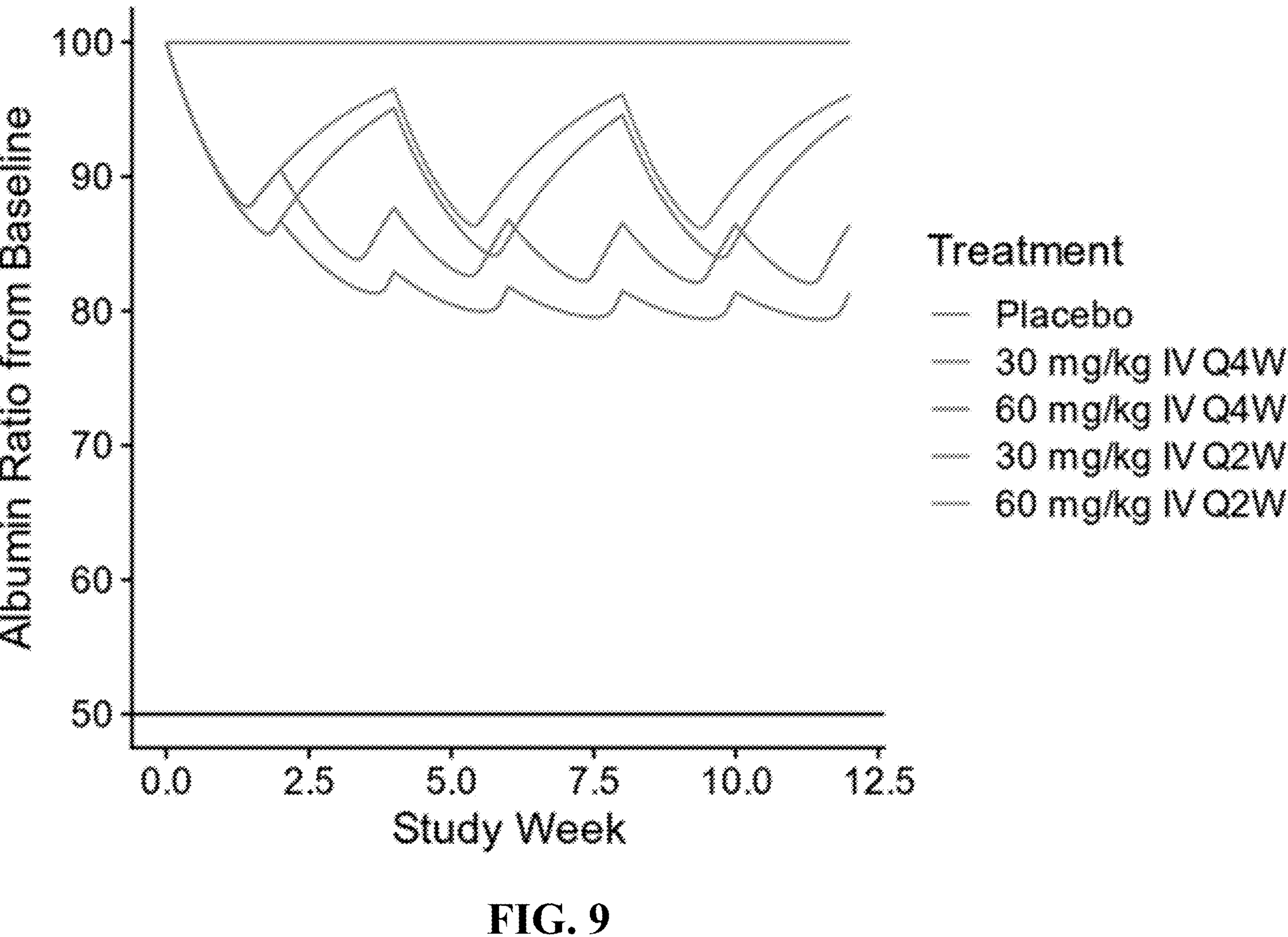
FIG. 9 is a graph showing the results of modeling designed to predict the impact of various doses of M281 on the level of serum albumin.

The impact of various intravenous doses (30 mg/kg Q4W, 60 mg/kg Q4W, 30 mg/kg Q2W, 60 mg/kg Q2W) of M281 on serum albumin was modeled. As can be seen in FIG. 9, all of the modeled doses suggest a reduction in serum albumin that is less than 25%. A 15 mg/kg Q2W dose is expected to exhibit a reduction in serum albumin that is similar to or less than that modeled for a 30 mg/kg Q2W dose.

Example 4. Clinical Study Protocol

A clinical study is performed comparing the effectiveness of various dosing regimens on fetal and neonatal alloimmune and/or autoimmune disorders by infusion of the anti-FcRn antibodies described herein in a pregnant subject identified as carrying a fetus or neonate in need thereof. As described above, diseases and disorders that may benefit from FcRn inhibition by the isolated anti-FcRn antibodies described herein include diseases and disorders in a fetus and/or neonate that are caused by the transfer of maternal pathogenic antibodies (e.g., maternal pathogenic IgG antibodies) across the placenta from a pregnant subject to the fetus and/or neonate. The diseases and disorders that may benefit from FcRn inhibition by the isolated anti-FcRn antibodies described herein are fetal and neonatal alloimmune thrombocytopenia (FNAIT), hemolytic disease of the fetus and newborn (HDFN), alloimmune pan-thrombocytopenia, congenital heart block, fetal arthrogryposis, neonatal myasthenia gravis, neonatal autoimmune hemolytic anemia, neonatal anti-phospholipid syndrome, neonatal polymyositis, dermatomyositis, neonatal lupus, neonatal scleroderma. Behcet's disease, neonatal Graves' disease, neonatal Kawasaki disease, neonatal autoimmune thyroid disease, and neonatal type I diabetes mellitus.

The dosing regimens are tested at a loading dose of 60 mg/kg followed by maintenance doses. One cohort will receive a maintenance dose of 15 mg/kg every 2 weeks, a second cohort will receive a maintenance dose of 30 mg/kg every 2 weeks, a third cohort will receive a maintenance dose of 15 mg/kg once per month, and a fourth cohort will receive a maintenance dose of 30 mg/kg once per month. In each case, the schedule will be followed until birth of the infant.

Levels of IgG and serum albumin are measured in the pregnant subject every week.

Example 5. M281 is Safe and Well-Tolerated in Patients with Generalized Myasthenia Gravis (gMG)

Sixty eight patients with either anti-AChR or anti-MuSK autoantibodies were randomized 1:1:1:1:1 to 4 M281 treatment groups or a placebo group. Doses of M281 were 5 mg/kg Q4W, 30 mg/kg Q4W and 60 mg/kg Q2W. A single dose of 60 mg/kg was also included to evaluate the duration of IgG lowering and efficacy. To maintain study blinding, all patients received an intravenous infusion (either M281 or placebo) every other week for a total of 5 infusions during the 8-week treatment period. After completion of the follow-up period, patients could enroll in a separate open-label extension study and receive treatment with M281.

M281 was generally well-tolerated. There were no discontinuations due to treatment emergent adverse effects (TEAEs) and no severe adverse effects (AEs) with M281. There was one serious adverse effect (SAE) in the M281 group (shoulder pain) and two SAEs in the placebo group (one case of ischemic stroke and one case of MG worsening). The frequency of infections in the M281 combined dose group vs. the placebo group was 33.3% vs. 21.4%, respectively and there were no severe or serious infections. The percentage of headaches with M281 was comparable to placebo. Accordingly, M281 is safe and well-tolerated in patients with gMG.

Figure 12:
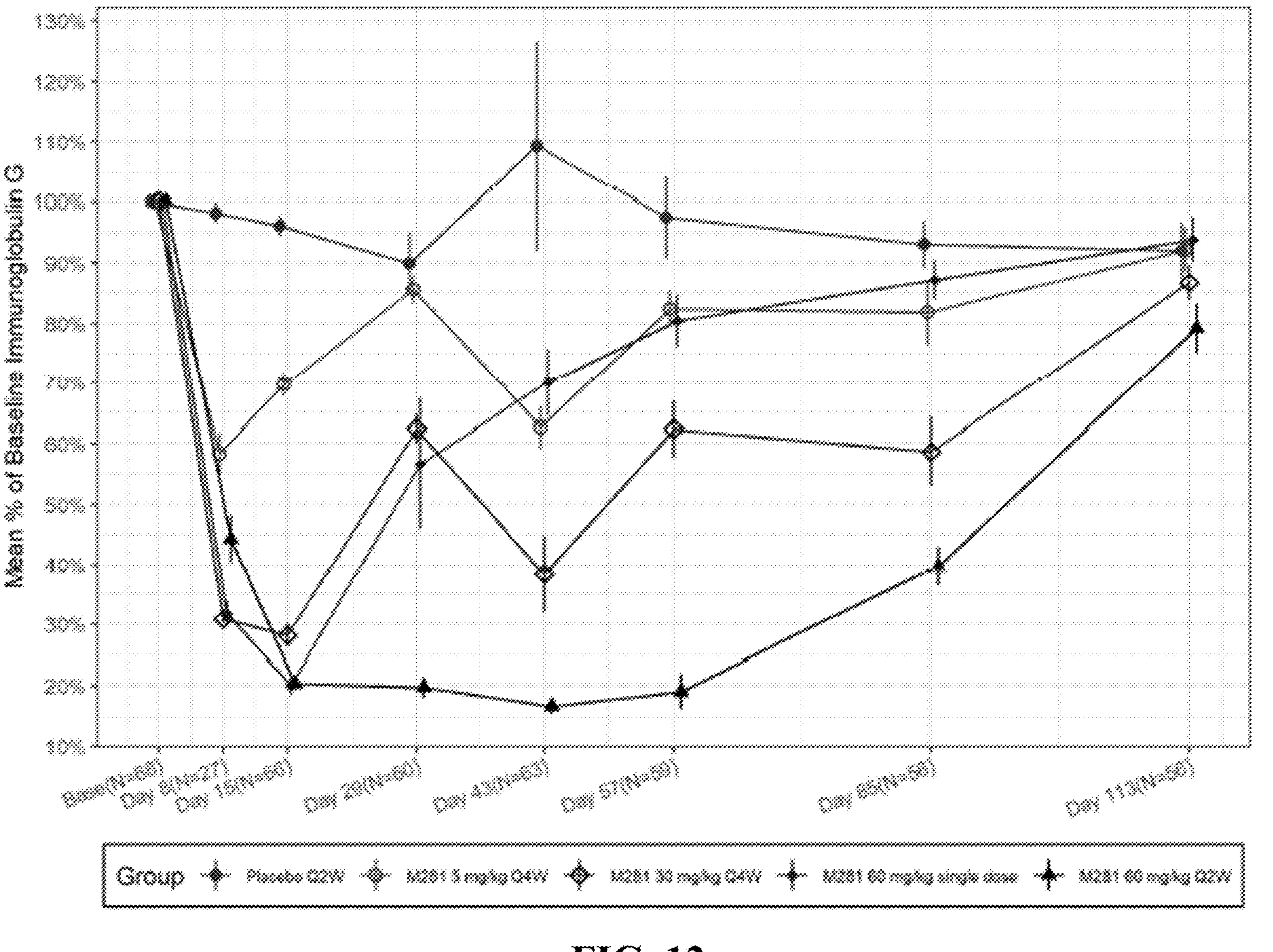
FIG. 12 is a graph showing mean (±SE) of percent of baseline IgG over time.
Figure 13:
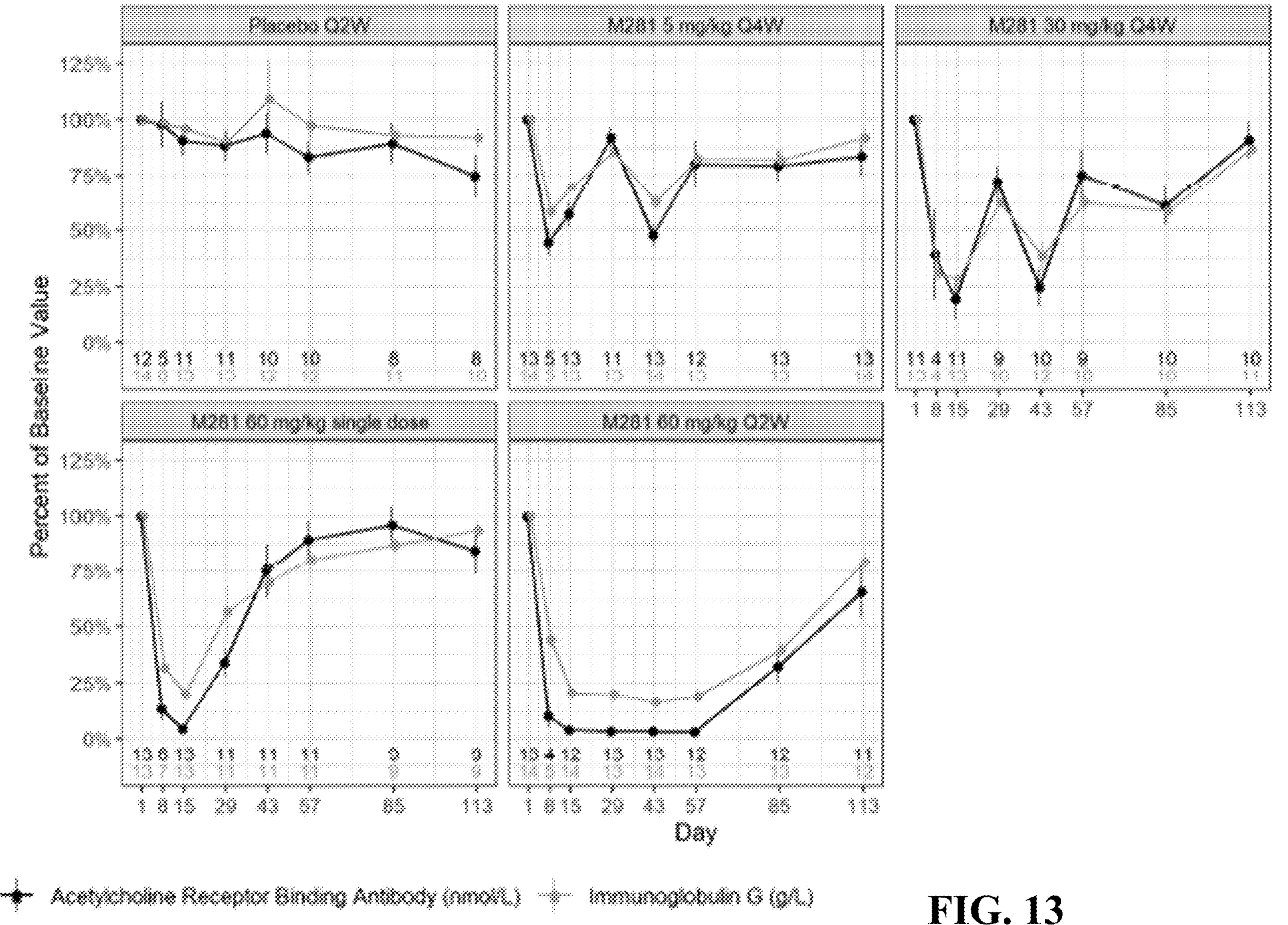
FIG. 13 is a graph showing the arithmetic mean (±SE) of percent of baseline over time of the AChR binding antibody and IgG.

Example 6. M281 Reduces Serum IgG, as Well as Anti-AChR and Anti-MuSK Autoantibodies Serum samples were collected from individuals as provided in Example 5 on infusion days and analyzed for M281 concentrations using an enzyme-linked immunosorbent assay (ELISA) method. Blood samples were taken immediately prior to the beginning of infusion at visits when a study agent administration was scheduled and post-infusion on days 1 and 57. Serum samples were also analyzed for changes in concentrations of total IgG, IgG subclasses, IgA, IgM and IgE and pathogenic MG antibodies (anti-AChR and anti-MuSK). Serum total IgG levels were accessed by Roche Cobas® 8000. Serum IgG subclasses (IgG1, IgG2, IgG3, and IgG4) and IgA, IgM and IgE levels were measured by a validated Immunonephelometry (Siemens) platform on Behring Nephelometer II (BN II). Serum levels of pathogenic anti-AChR and anti-MuSK autoantibodies were analyzed by ARUP Laboratories, UT, USA and The Doctors Laboratory, London, UK, respectively. Median trough serum M281 concentrations (Ctrough) were all below the lower limit of quantification (<0.15 μg/mL) for the 5 mg/kg Q4W and 30 mg/kg Q4W dose groups. However, median Ctrough ranged from 4.01 to 36.33 μg/mL for the 60 mg/kg Q2W group. No accumulations in serum M281 concentrations over time were observed across the 5 mg/kg Q4W, 30 mg/kg Q4W, and 60 mg/kg Q2W treatment groups. For subjects treated with M281, the overall incidence of antibodies to M281 through Day 113 (Week 16) was 40.7% (n=22). Antibody responses to M281 were in low titers (all titer levels≤1:16). Eight (34.4%) of the 22 subjects who were positive for antibodies to M281 had antibodies that were able to neutralize the bioactivity of M281 in vitro. Treatment with nipocalimab demonstrated substantial, rapid, and dose-dependent reduction in serum total IgG levels. Serum total IgG at one week after the first nipocalimab infusion resulted in mean reductions from baseline up to 40% at 5 mg/kg and 70% at 30 mg/kg or higher doses (FIG. 12). Maximal IgG reductions of 42%, 73% and 80% were observed with 5 mg/kg q4w, 30 mg/kg q4w and 60 mg/kg single dose or q4w (FIG. 12). The q2w dosing regimen provided a sustained reduction in mean serum IgG and the q4w dosing regimen provided peak and nadir reductions in mean serum IgG levels, with nadir approximately 2 weeks after nipocalimab administration and peak approximately 4 weeks after administration. Across nipocalimab treatment groups, similar reductions were seen with all IgG subclasses and no changes in total IgM, IgA, and IgE were observed. Dose-dependent reductions in pathogenic anti-AChR autoantibodies, concurrent with reductions in total IgG were also observed across nipocalimab treatment groups (FIG. 13). Reductions in anti-MuSK autoantibodies were observed in patients who were positive for anti-MuSK autoantibodies. Dose-dependent decreases from baseline in mean serum albumin were observed in the nipocalimab groups. At the highest dose group 60 mg/kg q2w, mean albumin reduction was approximately 20%. One patient in the 60 mg/kg q2w group had grade 2 albumin reduction. No patient had any symptom due to albumin reduction. All patients had albumin values within the normal range except 1 in the 60 mg/kg q2w group who had a grade 2 decrease (albumin value of 27 g/L on day 43; baseline value: 40 g/L; normal range: 35-55 g/L). Asymptomatic, dose-dependent and reversible elevations in non-fasting mean total cholesterol, LDL and HDL were observed in the higher dose nipocalimab groups. The cholesterol:HDL ratio were <5% across all dose groups. Maximum mean percentage increases in total cholesterol, LDL and HDL in the 30 mg/kg q4w group were 9.3%, 8.4%; 17.9%; in the 60 mg/kg single dose group were 15.6%, 13% and 23.3%; in the 60 mg/kg q2w group were 23.1%, 28.1% and 19.8%, respectively. In the 30 mg/kg q4w and 60 mg/kg single doses, the maximum mean values occurred primarily within a week of the first infusion whereas subsequent elevations were of lower magnitude.

Accordingly, M281 reduces serum IgG, as well as anti-AChR and anti-MuSK autoantibodies in patients with gMG.

Example 7. M281 Improves MG-ADL and QMG Scores in Patients with gMG

MG-ADL and QMG scores were measured in patients suffering from gMG following administration of M281 as provided in Example 5. Patient who received M281 achieved substantial and rapid reductions in serum total IgG and anti-AChR IgG autoantibodies which were correlated with MG-ADL improvement.

As shown in Tables 1 and 2, patients treated with M281 achieved a robust mean improvement from baseline in MG-ADL scores across M281 continuous dosing arms vs. placebo at the end of the treatment period (Day 57).

TABLE 1

| | | Nipocalimab | | | |
|---|---|---|---|---|---|
| | Placebo q2w (n = 14) | 5 mg/kg q4w (n = 14) | 30 mg/kg q4w (n = 13) | 60 mg/kg single dose (n = 13) | 60 mg/kg q2w (n = 14) |
| MG-ADL | | | | | |
| Baseline, mean (SD) | 7.3 (2.79) | 8.0 (2.75) | 8.0 (2.61) | 7.9 (2.78) | 8.1 (3.25) |
| Day 57, mean (SD) | 5.2 (3.09) | 5.5 (3.32) | 4.0 (2.63) | 6.5 (3.84) | 4.3 (2.95) |
| Change from baseline, mean (SD) | −1.8 (3.22) | −2.5 (2.41) | −3.9 (3.00) | −1.5 (2.82) | −3.9 (3.66) |
| LS Means (SE)[a] | −2.4 (0.9) | −2.4 (0.9) | −3.7 (0.9) | −1.4 (1.0) | −3.7 (0.9) |
| Difference in LS Means (nipocalimab vs placebo)[a] | | −0.0 (1.1) | −1.3 (1.1) | 1.0 (1.1) | −1.3 (1.1) |
| 95% CI | | (−2.1, 2.1) | (−3.5, 0.9) | (−1.2, 3.1) | (−3.4, 0.8) |
| p-value | | 0.99 | 0.24 | 0.36 | 0.22 |
| p-value of linear trend test of change from baseline[Error! Reference source not found.] | 0.03 | | | | |
| p-value of linear trend test based on the rank of change from baseline[Error! Reference source not found.] | 0.004 | | | | |
| QMG scores | | | | | |
| Baseline, mean (SD) | 17.6 (4.20) | 15.9 (2.93) | 17.1 (4.23) | 16.1 (4.07) | 16.9 (2.79) |
| Day 57, mean (SD) | 13.2 (4.92) | 12.2 (4.62) | 13.1 (2.64) | 14.0 (4.56) | 11.3 (4.40) |
| Change from baseline, mean (SD) | −3.7 (2.94) | −3.5 (4.10) | −4.1 (3.45) | −1.5 (2.54) | −5.9 (5.30) |
| LS Means (SE)[a] | −3.4 (1.2) | −3.5 (1.1) | −3.9 (1.2) | −1.3 (1.2) | −5.2 (1.1) |
| Difference in LS Means (nipocalimab vs placebo)[a] | | −0.1 (1.5) | −0.5 (1.6) | 2.1 (1.6) | −1.8 (1.5) |
| 95% CI | | (−3.1, 2.9) | (−3.6, 2.6) | (−1.0, 5.2) | (−4.8, 1.2) |
| p-value | | 0.93 | 0.73 | 0.18 | 0.23 |
| MG-QoL-15r total scores | | | | | |
| Baseline, mean (SD) | 17.4 (5.24) | 15.4 (6.26) | 15.6 (7.83) | 17.8 (5.87) | 15.7 (6.82) |
| Day 57, mean (SD) | 15.6 (7.03) | 13.6 (7.49) | 9.1 (7.88) | 16.7 (5.54) | 12.0 (8.53) |
| Change from baseline, mean (SD) | −2.0 (4.58) | −1.7 (4.16) | −6.8 (5.73) | −1.2 (1.91) | −3.7 (5.37) |
| LS Means (SE)[a] | −1.9 (1.4) | −2.1 (1.3) | −6.9 (1.4) | −1.3 (1.4) | −4.0 (1.3) |
| Difference in LS Means (nipocalimab vs placebo)[a] | | −0.2 (1.7) | −5.1 (1.8) | 0.6 (1.8) | −2.2 (1.7) |
| 95% CI | | (−3.7, 3.2) | (−8.6, −1.5) | (−3.0, 4.1) | (−5.6, 1.3) |
| p-value | | 0.90 | 0.005 | 0.754 | 0.21 |

[a]LS means, CIs, and p-values are from a mixed effect Model Repeated Measures (MMRM) at Day 57 with treatment group, visit, treatment group by visit interaction, and autoantibody type as fixed effects, and the baseline score as a covariate. Compound symmetry covariance structure is used;

[b]Linear trend test is based on the change from baseline at Day 57. The 60 mg/kg nipocalimab single-dose treatment group was not included in this analysis and the coefficients for testing linear trend used were −3, −1, 1, 3 for the Placebo, 5 mg/kg nipocalimab q4w, 30 mg/kg nipocalimab q4w, and 60 mg/kg nipocalimab q2w groups, respectively;

[c]Linear trend test is based on the rank of the change from baseline at Day 57. Subjects without a Day 57 result were assigned the largest rank-based on the rest of the subjects' results. The 60 mg/kg nipocalimab single-dose treatment group was not included in this analysis and the coefficients for testing linear trend used were −3, −1, 1, 3 for the Placebo, 5 mg/kg nipocalimab q4w, 30 mg/kg nipocalimab q4w, and 60 mg/kg nipocalimab q2w groups, respectively.

ITT, intent-to-treat; LS means, least squares means; MG-ADL, Myasthenia Gravis-Activities of Daily Living Total Score; MG-QoL-15r, Revised Myasthenia Gravis Quality of Life-15; QMG, Quantitative Myasthenia Gravis; q2w, every 2 weeks; q4w, every 4 weeks; SD, Standard deviation; SE, standard error The highest percentage of subjects with 2-, 3-, 4-, 5-, 6-, 7-, or ≥8-point improvement in total MG-ADL score from baseline to Day 57 were observed in the following treatment groups (Table 2): i) M281 30 mg/kg q4w comprising: 2-point Improvement, 83.3% of patients; 3-point Improvement, 66.7% of patients; 4-point Improvement, 41.7% of patients; 5-point Improvement, 41.7% of patients; 6-point Improvement, 25% of patients; 7-point Improvement, 25% of patients; and ≥8-point Improvement, 8.3% of patients; and ii) M281 60 mg/kg q2w comprising: 2-point Improvement, 85.7% of patients; 3-point Improvement, 78.6% of patients; 4-point Improvement, 50% of patients; 5-point Improvement, 42.9% of patients; 6-point Improvement, 21.4% of patients; 7-point Improvement, 14.3% of patients; and ≥8-point Improvement, 14.3% of patients. Reductions from baseline in the mean MG ADL total scores were observed for all treatment groups (including placebo) at Day 85 and Day 113, after the last dose administration on Day 57. The greatest and most consistent reductions were observed in subjects in the M281 30 mg/kg q4w and 60 mg/kg q2w treatment groups.

TABLE 2

Myasthenia Gravis-Activities of Daily Living at Day 57-Responder Analysis, ITT Population

| Criteria | Placebo q2w (N = 14) | Nipocalimab 5 mg/kg q4w (N = 14) | Nipocalimab 30 mg/kg q4w (N = 13) | Nipocalimab 60 mg/kg Single Dose (N = 13) | Nipocalimab 60 mg/kg q2w (N = 14) |
|---|---|---|---|---|---|
| Number of Subjects with Data at Day 57, n (%) | 11 (78.6) | 14 (100) | 12 (92.3) | 13 (100) | 14 (100) |
| 2-point Improved | | | | | |
| Yes | 7 (63.6) | 9 (64.3) | 10 (83.3) | 7 (53.8) | 12 (85.7) |
| No | 4 (36.4) | 5 (35.7) | 2 (16.7) | 6 (46.2) | 2 (14.3) |
| p-value | | 1.0000 | 0.3707 | 0.6968 | 0.3500 |
| 3-point Improved | | | | | |
| Yes | 5 (45.5) | 9 (64.3) | 8 (66.7) | 5 (38.5) | 11 (78.6) |
| No | 6 (54.5) | 5 (35.7) | 4 (33.3) | 8 (61.5) | 3 (21.4) |
| p-value | | 0.4347 | 0.4136 | 1.0000 | 0.1153 |
| 4-point Improved | | | | | |
| Yes | 1 (9.1) | 5 (35.7) | 5 (41.7) | 3 (23.1) | 7 (50.0) |
| No | 10 (90.9) | 9 (64.3) | 7 (58.3) | 10 (76.9) | 7 (50.0) |
| p-value | | 0.1804 | 0.1550 | 0.5963 | 0.0421 |
| 5-point Improved | | | | | |
| Yes | 1 (9.1) | 2 (14.3) | 5 (41.7) | 2 (15.4) | 6 (42.9) |
| No | 10 (90.9) | 12 (85.7) | 7 (58.3) | 11 (84.6) | 8 (57.1) |
| p-value | | 1.0000 | 0.1550 | 1.0000 | 0.0900 |
| 6-point Improved | | | | | |
| Yes | 1 (9.1) | 1 (7.1) | 3 (25.0) | 1 (7.7) | 3 (21.4) |
| No | 10 (90.9) | 13 (92.9) | 9 (75.0) | 12 (92.3) | 11 (78.6) |
| p-value | | 1.0000 | 0.5901 | 1.0000 | 0.6043 |
| 7-point Improved | | | | | |
| Yes | 1 (9.1) | 1 (7.1) | 3 (25.0) | 0 | 2 (14.3) |
| No | 10 (90.9) | 13 (92.9) | 9 (75.0) | 13 (100) | 12 (85.7) |
| p-value | | 1.0000 | 0.5901 | 0.4583 | 1.0000 |
| ≥8-point Improved | | | | | |
| Yes | 1 (9.1) | 0 | 1 (8.3) | 0 | 2 (14.3) |
| No | 10 (90.9) | 14 (100) | 11 (91.7) | 13 (100) | 12 (85.7) |
| p-value | | 0.4400 | 1.0000 | 0.4583 | 1.0000 |

[1] p-values are from Fisher's exact test comparing each active group vs. placebo group.

[2] Percentage for the improvement categories is based on number of subjects with Data at Day 57.

A greater proportion of patients treated with M281 exhibited rapid improvement (within two weeks of treatment) in MG-ADL across all 4 dosing arms vs. placebo. 51.9% of patients who received M281 (all doses) reported a durable MG-ADL response (defined as MG-ADL improvement of ≥2 points from baseline for at least 4 consecutive weeks during the first 8 weeks of treatment) vs. 15.4% of those who received placebo (p=0.017). The rapid and durable MG-ADL response indicates a clear clinical benefit with nipocalimab therapy, underscoring the potential for long-term treatment. Observed changes from baseline in MG-ADL following nipocalimab administration at doses ranging from 5 mg/kg q4w to 60 mg/kg q2w were dose-dependent, rapid in onset and closely associated with in onset and magnitude of IgG or anti-AChR autoantibody lowering. These results suggest that IgG lowering predicts MG efficacy in patients with gMG.

Duration of response was defined as number of consecutive weeks that the subject had an improvement ≥2 on MG-ADL (Table 3). The median duration of response was longer among subjects treated with M281 (ranging from 29.0 to 36.0 days across doses groups) compared with subjects treated with placebo (15.0 days). The percentage of subjects with durable response were higher in the M281 treatment groups compared to placebo treatment group. At Day 57, the number of subjects with a durable response (defined as ≥4 consecutive weeks with improvement ≥2 on MG-ADL) were higher in the M281-treated subjects (42.9%, 46.2%, 53.9%, and 64.3% in the 5 mg/kg q4w, 30 mg/kg q2w, 60 mg/kg single dose, and 60 mg/kg q2w dose groups, respectively) compared to the placebo-treated group (14.3%). The treatment difference reached the p-value of 0.0461 for the 60 mg/kg single-dose group and the p-value of 0.0183 for the 60 mg/kg q2w dose group. Additionally, the 5 mg/kg q4w group showed p-value of 0.2087, and the 30 mg/kg q4w group showed p-value of 0.1032. The percentage of subjects with a rapid onset of durable response (i.e., by the Week 2 planned visit [≤17 days from first study agent administration]) were higher among M281 treatment groups compared to placebo treatment group and showed values of: 42.9% (p=0.2087) for the 5 mg/kg Q4W treatment group; 38.5% (p=0.2087) for the 30 mg/kg Q4W treatment group; 46.2% (p=0.1032) for the 60 mg/kg single dose treatment group; 42.9% (p=0.2087) for the 60 mg/kg Q2W treatment group; and 14.3% for placebo.

TABLE 3

| Duration of Response up to Day 57-Myasthenia Gravis-Activities of Daily Living, Intent-to-treat Population | | | | | |
|---|---|---|---|---|---|
| | | Nipocalimab | | | |
| | Placebo q2w (N = 14) | 5 mg/kg q4w (N = 14) | 30 mg/kg q4w (N = 13) | 60 mg/kg Single Dose (N = 13) | 60 mg/kg q2w (N = 14) |
| Subjects with Improvement ≥2 on MG-ADL | | | | | |
| Yes | 11 (78.57) | 12 (85.71) | 10 (76.92) | 13 (100) | 12 (85.71) |
| No | 3 (21.43) | 2 (14.29) | 3 (23.08) | 0 | 2 (14.29) |
| p-value[c] | | 1.0000 | 1.0000 | 0.2222 | 1.0000 |
| Duration of Response (Days)[a] | | | | | |
| n | 11 | 12 | 10 | 13 | 12 |
| Mean | 17.8 | 25.0 | 26.9 | 25.8 | 31.9 |
| Standard Deviation | 15.22 | 20.80 | 20.26 | 18.56 | 15.04 |
| Minimum | 1 | 1 | 1 | 1 | 1 |
| Median | 15.0 | 29.0 | 36.0 | 28.0 | 34.5 |
| Maximum | 44 | 47 | 46 | 45 | 50 |
| Subjects with Durable Response[b] | | | | | |
| Yes | 2 (14.29) | 6 (42.86) | 6 (46.15) | 7 (53.85) | 9 (64.29) |
| No | 12 (85.71) | 8 (57.14) | 7 (53.85) | 6 (46.15) | 5 (35.71) |
| p-value[c] | | 0.2087 | 0.1032 | 0.0461 | 0.0183 |
| Duration of Durable Response (Days)b | | | | | |
| n | 2 | 6 | 6 | 7 | 9 |
| Mean | 43.5 | 44.3 | 41.8 | 41.3 | 39.0 |
| Standard Deviation | 0.71 | 1.51 | 6.37 | 5.96 | 8.22 |
| Minimum | 43 | 43 | 29 | 28 | 28 |
| Median | 43.5 | 44.0 | 44.0 | 43.0 | 43.0 |
| Maximum | 44 | 47 | 46 | 45 | 50 |
| Subjects with Durable Response within ≤17 days[b] | | | | | |
| Yes | 2 (14.29) | 6 (42.86) | 5 (38.46) | 6 (46.15) | 6 (42.86) |
| No | 12 (85.71) | 8 (57.14) | 8 (61.54) | 7 (53.85) | 8 (57.14) |
| p-value[c] | | 0.2087 | 0.2087 | 0.1032 | 0.2087 |

[a]Duration of response is defined as the number of consecutive days that the subject has an improvement ≥2 on MG-ADL. If the subject had an improvement ≥2 for only one visit the duration will be assumed to be 1 day.

[b]Durable response is defined as ≥4 weeks (26 days) with improvement ≥2 on MG-ADL.

[c]P-value from Fisher's exact test comparing Placebo to each nipocalimab dose group.

Time to response was defined as time from first infusion to the first time with improvement ≥2 on MG ADL. The median time to response ranged from 15.0 to 15.5 days across dose groups for the M281-treated subjects and was 16.0 days for placebo-treated subjects.

On Day 57 (before the last dose), the greatest reductions from baseline in the mean total QMG scores were observed in subjects in the M281 30 mg/kg q4w and 60 mg/kg q2w treatment groups (Table 1).

Treatment with M281 produced following changes from baseline on QMG scale: −0.1 LS mean, p=0.9289 for the 5 mg/kg q4w treatment group; −0.5 LS mean, p=0.7304 for the 30 mg/kg q4w treatment group; 2.1 LS mean, p=0.1845 for the 60 mg/kg single dose; and −1.8 LS mean, p=0.2344 for the 60 mg/kg q2w treatment group. Single-dose administration of M28160 mg/kg also produced large reductions in mean total QMG scores through Day 29 (Week 4; mean change from baseline: −2.2), with the maximum reduction at Day 15 (mean change from baseline: −4.1). The highest percentage of subjects with 3-, 4-, 5-, 6-, 7-, or ≥8 point improvement in total QMG score from baseline to Day 57 were observed in the following M281 treatment groups (Table 4): i) 30 mg/kg q4w comprising: 3-point Improvement, 60% of patients; 4-point Improvement, 60% of patients; 5-point Improvement, 50% of patients; 6-point Improvement, 40% of patients; 7-point Improvement, 10% of patients; and ≥8-point Improvement, 10% of patients; and ii) 60 mg/kg q2w comprising: 3-point Improvement, 76.9% of patients; 4-point Improvement, 76.9% of patients; 5-point Improvement, 61.5% of patients; 6-point Improvement, 38.5% of patients; 7-point Improvement, 23.10% of patients; and ≥8-point Improvement, 23.1% of patients. The reduction in the mean QMG total scores, after the last dose administration on Day 57, was maintained up to Day 113 across all treatment groups.

TABLE 4

Quantitative Myasthenia Gravis at Day 57-Responder Analysis, Intent-to-Treat Population

| Criteria | Placebo q2w (N = 14) | Nipocalimab 5 mg/kg q4w (N = 14) | Nipocalimab 30 mg/kg q4w (N = 13) | Nipocalimab 60 mg/kg Single Dose (N = 13) | Nipocalimab 60 mg/kg q2w (N = 14) |
|---|---|---|---|---|---|
| Number of Subjects with Data at Day 57, n (%) | 11 (78.6) | 13 (92.9) | 10 (76.9) | 11 (84.6) | 13 (92.9) |
| 3-point Improved | | | | | |
| Yes | 8 (72.7) | 6 (46.2) | 6 (60.0) | 4 (36.4) | 10 (76.9) |
| No | 3 (27.3) | 7 (53.8) | 4 (40.0) | 7 (63.6) | 3 (23.1) |
| p-value | | 0.2397 | 0.6594 | 0.1984 | 1.0000 |
| 4-point Improved | | | | | |
| Yes | 5 (45.5) | 5 (38.5) | 6 (60.0) | 3 (27.3) | 10 (76.9) |
| No | 6 (54.5) | 8 (61.5) | 4 (40.0) | 8 (72.7) | 3 (23.1) |
| p-value | | 1.0000 | 0.6699 | 0.6594 | 0.2060 |
| 5-point Improved | | | | | |
| Yes | 5 (45.5) | 5 (38.5) | 5 (50.0) | 1 (9.1) | 8 (61.5) |
| No | 6 (54.5) | 8 (61.5) | 5 (50.0) | 10 (90.9) | 5 (38.5) |
| p-value | | 1.0000 | 1.0000 | 0.1486 | 0.6824 |
| 6-point Improved | | | | | |
| Yes | 2 (18.2) | 5 (38.5) | 4 (40.0) | 1 (9.1) | 5 (38.5) |
| No | 9 (81.8) | 8 (61.5) | 6 (60.0) | 10 (90.9) | 8 (61.5) |
| p-value | | 0.3864 | 0.3615 | 1.0000 | 0.3864 |
| 7-point Improved | | | | | |
| Yes | 2 (18.2) | 5 (38.5) | 1 (10.0) | 0 | 3 (23.1) |
| No | 9 (81.8) | 8 (61.5) | 9 (90.0) | 11 (100) | 10 (76.9) |
| p-value | | 0.3864 | 1.0000 | 0.4762 | 1.0000 |
| ≥8-point Improved | | | | | |
| Yes | 2 (18.2) | 3 (23.1) | 1 (10.0) | 0 | 3 (23.1) |
| No | 9 (81.8) | 10 (76.9) | 9 (90.0) | 11 (100) | 10 (76.9) |
| p-value | | 1.0000 | 1.0000 | 0.4762 | 1.0000 |

[3] p-values are from Fisher's exact test comparing each active group vs. placebo group.
[4] Percentage for the improvement categories is based on number of subjects with Data at Day 57.

Durable response was defined as the number of consecutive days that the subject has an improvement ≥3 on QMG. At Day 57, the percentage of subjects with a durable response were higher in most M281 treatment groups and comprised: 35.7%, p=1 for 5 mg/kg q4w; 38.5%, p=0.6946 for 30 mg/kg q4w; 15.38%, p=0.6483 for 60 mg/kg single dose; and 42.9%, p=0.6946 for 60 mg/kg q2w, compared to placebo group (28.57%) (Table 5).

TABLE 5

Duration of Response up to Day 57-Quantitative Myasthenia Gravis, Intent-to-treat population

| | Placebo q2w (N = 14) | Nipocalimab 5 mg/kg q4w (N = 14) | Nipocalimab 30 mg/kg q4w (N = 13) | Nipocalimab 60 mg/kg Single Dose (N = 13) | Nipocalimab 60 mg/kg q2w (N = 14) |
|---|---|---|---|---|---|
| Subjects with Improvement ≥3 on QMG | | | | | |
| Yes | 10 (71.43) | 11 (78.57) | 11 (84.62) | 9 (69.23) | 11 (78.57) |
| No | 4 (28.57) | 3 (21.43) | 2 (15.38) | 4 (30.77) | 3 (21.43) |
| p-valuec | | 1.0000 | 0.6483 | 1.0000 | 1.0000 |
| Duration of Response (Days)[a] | | | | | |
| n | 10 | 11 | 11 | 9 | 11 |
| Mean | 22.0 | 23.0 | 25.0 | 13.8 | 23.2 |
| Standard Deviation | 19.16 | 20.61 | 18.84 | 18.03 | 21.68 |
| Minimum | 1 | 1 | 1 | 1 | 1 |
| Median | 16.0 | 15.0 | 24.0 | 1.0 | 31.0 |
| Maximum | 44 | 47 | 44 | 44 | 50 |
| Subjects with Durable Response[b] | | | | | |
| Yes | 4 (28.57) | 5 (35.71) | 5 (38.46) | 2 (15.38) | 6 (42.86) |
| No | 10 (71.43) | 9 (64.29) | 8 (61.54) | 11 (84.62) | 8 (57.14) |
| p-value[c] | | 1.0000 | 0.6946 | 0.6483 | 0.6946 |

TABLE 5-continued

Duration of Response up to Day 57-Quantitative Myasthenia Gravis, Intent-to-treat population

| | Placebo q2w (N = 14) | Nipocalimab 5 mg/kg q4w (N = 14) | 30 mg/kg q4w (N = 13) | 60 mg/kg Single Dose (N = 13) | 60 mg/kg q2w (N = 14) |
|---|---|---|---|---|---|
| Duration of Durable Response (Days)[b] | | | | | |
| n | 4 | 5 | 5 | 2 | 6 |
| Mean | 43.3 | 43.8 | 43.2 | 43.5 | 41.7 |
| Standard Deviation | 0.50 | 2.17 | 0.45 | 0.71 | 6.19 |
| Minimum | 43 | 41 | 43 | 43 | 31 |
| Median | 43.0 | 44.0 | 43.0 | 43.5 | 43.0 |
| Maximum | 44 | 47 | 44 | 44 | 50 |
| Subjects with Durable Response within ≤17 days[b] | | | | | |
| Yes | 4 (28.57) | 4 (28.57) | 5 (38.46) | 2 (15.38) | 5 (35.71) |
| No | 10 (71.43) | 10 (71.43) | 8 (61.54) | 11 (84.62) | 9 (64.29) |
| p-value[c] | | 1.0000 | 0.6946 | 0.6483 | 1.0000 |

[a]Duration of response is defined as the number of consecutive days that the subject has an improvement ≥3 on QMG. If the subject had an improvement ≥3 for only one visit the duration will be assumed to be 1 day.
[b]Durable response is defined as ≥4 weeks (26 days) with improvement ≥3 on QMG.
[c]P-value from Fisher's exact test comparing Placebo to each nipocalimab dose group.

Duration of response was defined as number of consecutive weeks that the subject had an improvement ≥3 on QMG. The longest median duration of response was observed in the 60 mg/kg q2w group (31.0 days), followed by the 30 mg/kg q4w group (24.0 days). The median duration of response was the shortest in the 60 mg/kg single-dose group (1.0 day), followed by the 5 mg/kg q4w group (15.0 days) and the placebo group (16.0 days). The highest percentage of subjects with durable response were observed in the 60 mg/kg q2w dose group followed by the 30 mg/kg q4w group and the 5 mg/kg q4w group. The median duration of durable response ranged from 43.0 to 44.0 days across dose groups for the M281-treated subjects and was 43.0 days for placebo-treated subjects. The percentage of subjects with durable response within ≤17 days were higher in the 30 mg/kg q4w group (38.5%, p=0.6946) and the 60 mg/kg q2w group (35.7%, p=1), lower in the 60 mg/kg single-dose group (15.4%, p=0.6483), and similar in the 5 mg/kg q4w group (28.6%, p=1), compared to the placebo treatment group (28.6%). Time to response was defined as time from the first infusion to the first time with improvement ≥3 on QMG. The median time to response among M281-treated subjects (ranging from 15.0 to 16.0 days across dose groups) was shorter compared with that observed among placebo-treated subjects (22.0 days). The data show that M281 improves MG-ADL and QMG scores in patients with gMG.

Example 8. M281 Improves MG-QoL-15r Score and MGFA Classification in Patients with gMG MG-QoL-15r and MGFA scores measured in patients suffering from gMG following administration of M281 as provided in Example 5. A reduction in total MG-QoL-15r over time was observed following administration of study agent in all treatment groups, including placebo. On Day 57 (before the last dose), the greatest reductions from baseline in the mean total MG-QoL-15r scores were observed in subjects in the M281 30 mg/kg q4w and 60 mg/kg q2w treatment groups, and comprised the following scores: −2.1 LS mean, p=0.9008 for 5 mg/kg q4w; −6.9 LS mean, p=0.0054 for 30 mg/kg q4w; −1.3 LS mean, p=0.7540 for 60 mg/kg single dose; and −4.0 LS mean. P=0.2135 for 60 mg/kg q2w treatment group (Table 1).

Single-dose administration of M281 60 mg/kg also produced large reductions in mean total MG-QoL-15r scores through Day 29 (Week 4), but scores increased thereafter. Reduction in the mean MG-QoL15 total scores overtime, after the last dose administration on Day 57, were maintained up to Day 113 visit across all treatment groups, including placebo. At Day 57, MGFA scores showed: 21.4% improvement, 64.3% same status, p=0.2156 for 5 mg/kg q4w; 53.8% improvement, 23.1% same status, 7.7% worsened, p=0.3774 for 30 mg/kg q4w group; 30.8% improvement, 61.5% same status, p=0.4176 for 60 mg/kg single dose group; and 50% improvement, 28.6% same status, 7.1% worsened, p=0.4928 for 60 mg/kg q2w group (Table 8).

TABLE 8

Shift in Myasthenia Gravis Foundation of America Clinical Classification from Baseline to Day 57, Intent-to-Treat Population

| MGFA at Day 57 | Placebo q2w (N = 14) | Nipocalimab 5 mg/kg q4w (N = 14) | 30 mg/kg q4w (N = 13) | 60 mg/kg Single Dose (N = 13) | 60 mg/kg q2w (N = 14) |
|---|---|---|---|---|---|
| Number of Subjects with Data at Day 57, n (%) | 12 (85.7) | 12 (85.7) | 11 (84.6) | 12 (92.3) | 12 (85.7) |
| MGFA Clinical Classification Status | | | | | |
| Improved | 6 (42.9) | 3 (21.4) | 7 (53.8) | 4 (30.8) | 7 (50.0) |
| Same | 6 (42.9) | 9 (64.3) | 3 (23.1) | 8 (61.5) | 4 (28.6) |

TABLE 8-continued

Shift in Myasthenia Gravis Foundation of America Clinical Classification from Baseline to Day 57, Intent-to-Treat Population

| MGFA at Day 57 | Placebo q2w (N = 14) | Nipocalimab 5 mg/kg q4w (N = 14) | Nipocalimab 30 mg/kg q4w (N = 13) | Nipocalimab 60 mg/kg Single Dose (N = 13) | Nipocalimab 60 mg/kg q2w (N = 14) |
|---|---|---|---|---|---|
| Worsened | 0 | 0 | 1 (7.7) | 0 | 1 (7.1) |
| p-value | | 0.2156 | 0.3774 | 0.4176 | 0.4928 |

[5] p-values are from Cochran-Mantel-Haenszel test comparing each active group vs. placebo group At Day 57, the highest percentage of subjects with improved MGFA classification status at Day 57 were observed in 30 mg/kg q4w and 60 mg/kg q2w treatment groups. At baseline, the majority of subjects had an MGFA classification status of <IIIa (ranging from 69.2% to 78.6% across all treatment groups). Most of these subjects had either improved or maintained the same MGFA classification up to Day 57. Accordingly, M281 improves MG-QoL15 score and MGFA classification.

Example 9. Treatment of Myasthenia Gravis with M281 does not Significantly Elevate Cholesterol Elevations in total cholesterol and low-density lipoprotein (LDL) were reported recently with another experimental anti-FcRN antibody that is not M281 in the same pharmacological class of FcRn antagonists. This finding triggered a review of lipid data in Sponsor-completed and ongoing M281 studies. In the Phase 1 healthy volunteer and Phase 2 generalized myasthenia gravis studies, asymptomatic, dose dependent, reversible elevations in non-fasting mean total cholesterol were observed up to 25% of baseline. At the highest dose of 60 mg/kg every 2 weeks (Q2W), the mean percent change in total cholesterol increased to a stable maximum of 21% to 23% above baseline within 1 month of initiation of dosing and declined to near baseline level 1-2 months after the last dose. Maximum mean percentage increases in total cholesterol, LDL and HDL in the 30 mg/kg q4w group were 9.3%, 8.4%; 17.9%; in the 60 mg/kg single dose group were 15.6%, 13% and 23.3%; in the 60 mg/kg q2w group were 23.1%, 28.1% and 19.8%, respectively. In the 30 mg/kg q4w and 60 mg/kg single doses, the maximum mean values occurred primarily within a week of the first infusion whereas subsequent elevations were of lower magnitude. The cholesterol:HDL ratio were <5% across all dose groups. As a result of these findings, the following assessments are conducted: 1) assessment for lipids (total cholesterol, HDL, calculated LDL, and triglycerides) in fasting and non-fasting conditions at multiple time points on and off treatment, 2) exclusion criterion for patients with a recent significant cardiovascular event, 3) recommendation for lipid abnormalities management according to local health guidelines.

Example 10. Phase 3 Study Design

This multicenter, randomized, double-blind, placebo-controlled study is designed to evaluate the safety, tolerability, efficacy, PD, and immunogenicity of nipocalimab compared with placebo when administered by intravenous (IV) infusion to adults with gMG. Following a Screening Period of up to 4 weeks, approximately 150 eligible autoantibody positive (anti-AChR, anti-MuSK, and/or anti-LRP4) patients and 30 eligible autoantibody negative patients will be enrolled. Participants are randomized 1:1 to one of two treatment groups. The randomization is stratified by Baseline MG-ADL score (≤9, >9), region (East Asia, United states, rest of world), and autoantibody status (seropositive or seronegative). The treatment groups comprise: 1) placebo infusion once every 2 weeks (Q2W); and 2) nipocalimab infused at an initial loading dose of 30 mg/kg followed by infusion of 15 mg/kg maintenance dose every 2 weeks (Q2W). The regimen of 30 mg/kg loading dose administered intravenously on Day 1 followed by 15 mg/kg IV q2w maintenance doses from Week 2 onwards was based on observed data from the Phase 2 study and extensive population PK/PD/efficacy modeling analyses and simulation to evaluate the relationship between PK, IgG lowering, and MG-ADL as well as other efficacy and safety endpoints (including serum albumin and total cholesterol). The results indicated that the 15 mg/kg q2w dosing would provide the highest safety with near equivalent sustained IgG lowering (73.8%) when compared with the 30 mg q4w dosing (79.4%), with minimal additional MG-ADL improvement at steady-state trough. Therefore, the 15 mg/kg q2w dose regimen was selected as the single maintenance dose regimen to be studied for this Phase 3 study in gMG. Beginning at Baseline (Day 1), the patients receive an infusion of study drug (placebo or nipocalimab) over 15-30 minutes Q2W, and undergo safety, efficacy, PD, and immunogenicity assessments. Efficacy assessments are collected every 2-4 weeks. Efficacy assessments include MG-ADL, QMG, MG-QoL15r, and other patient-reported outcomes (PROs). All visits except Week 1, 3 and 23 (which will be done by phone contact) are performed at the study center. At the Week 24 visit, patients have the option of enrolling into a separate open-label extension (OLE) study where they receive nipocalimab infusions every 2 weeks. Patients who do not wish to continue in the OLE, or are not eligible for it, or who discontinue prematurely from the study and do not qualify for the OLE, return to the study center 8 weeks after their last infusion to complete safety follow-up assessments. Patients who require rescue treatment may be eligible to enter the OLE at the Investigator's discretion. Safety assessments include collection of adverse effects (AEs; including serious AEs [SAEs] and AEs of special interest [AESIs]), clinical laboratory testing (including chemistry, hematology, coagulation, and urinalysis), vital signs, ECGs, physical examinations, and the Columbia-Suicide Severity Rating Scale (C-SSRS). An independent Drug Safety Monitoring Board (DSMB) will be responsible for oversight of patient safety during the study.

Example 11. M281 is Safe and Well-Tolerated in Patient with gMG

A subject in Phase 3 study is evaluated, prior to treatment with M281, utilizing one or more of: physical examination, C-SSRS, vital signs, 12-lead ECG, lipid panel, urinalysis (dipstick), urine drug screen, pregnancy test (serum or urine), FSH (for menopausal women), HIV-1 & 2, hepatitis B & C. Additionally, blood and serum is collected for exploratory biomarker analysis, Ig type analysis, and clinical laboratory assessments. A subject with myasthenia gravis or a subject with gMG who have an insufficient clinical response to ongoing, stable standard of care therapy is evaluated utilizing physical examination, C-SSRS, vital signs, 12-lead ECG, lipid panel, urinalysis (dipstick), urine drug screen, pregnancy test (serum or urine), FSH (for menopausal women), HIV-1 & 2, and hepatitis B & C assessment tests prior to treatment with M281 to generate baseline scores. The subject is administered M281 at a single dose, or a loading dose and a maintenance dose every 2 weeks for 24 weeks. After 24 weeks, and throughout the study, the subject is evaluated for changes in vital signs, clinical laboratory values, and C-SSRS score.

Example 12. Treatment of Myasthenia Gravis with an Anti-FcRn Antibody Leads to Change from Baseline on MG-ADL Scale A subject in Phase 3 study is evaluated, prior to treatment with M281, utilizing Myasthenia Gravis-Activities of Daily Living (MG-ADL) scale. A subject with myasthenia gravis or a subject with gMG who have an insufficient clinical response to ongoing, stable standard of care therapy is evaluated utilizing MG-ADL prior to treatment with M281 to generate a MG-ADL score. The subject is administered M281 at a single dose, or a loading dose and a maintenance dose every 2 weeks for 24 weeks. After 24 weeks, and throughout the study, the subject is evaluated for changes in MG-ADL score. After 24 weeks, and throughout the study, the subject is evaluated using MG-ADL scale and found to achieve change from baseline on MG-ADL scale.

Example 13. Treatment of Myasthenia Gravis with an Anti-FcRn Antibody Leads to Change from Baseline on QMG and MG-QoL-15r Scales A subject in Phase 3 study is evaluated, prior to treatment with M281, utilizing QMG and MG-QoL-15r scales. A subject with myasthenia gravis or a subject with gMG who have an insufficient clinical response to ongoing, stable standard of care therapy is evaluated utilizing QMG and MG-QoL-15r prior to treatment with M281 to generate a QMG and MG-QoL-15r score. The subject is administered M281 at a single dose, or a loading dose and a maintenance dose every 2 weeks for 24 weeks. After 24 weeks, and throughout the study, the subject is evaluated for changes in QMG and MG-QoL15r scores. After 24 weeks, and throughout the study, the subject is evaluated using QMG and MG-QoL-15r scales and found to achieve change from baseline on QMG and MG-QoL-15r scales.

Example 14. Treatment of Myasthenia Gravis with an Anti-FcRn Antibody Leads to Change from Baseline on Neuro-QoL-Fatigue, EQ-5D-5L, MGFA, PGI-C, and PGI-S Scales A subject in Phase 3 study is evaluated, prior to treatment with M281, utilizing Neuro-QoL-Fatigue, EQ-5D-5L, MGFA, PGI-C, and PGI-S scales. A subject with myasthenia gravis or a subject with gMG who have an insufficient clinical response to ongoing, stable standard of care therapy is evaluated utilizing Neuro-QoL-Fatigue, EQ-5D-5L, MGFA, PGI-C, and PGI-S prior to treatment with M281 to generate a Neuro-QoL-Fatigue, EQ-5D-5L, MGFA, PGI-C, and PGI-S score. The subject is administered M281 at a single dose, or a loading dose and a maintenance dose every 2 weeks for 24 weeks. After 24 weeks, and throughout the study, the subject is evaluated for changes in Neuro-QoL-Fatigue, EQ-5D-5L, MGFA, PGI-C, and PGI-S scores. After 24 weeks, and throughout the study, the subject is evaluated using Neuro-QoL-Fatigue, EQ-5D-5L, MGFA, PGI-C, and PGI-S scales and found to achieve change from baseline on Neuro-QoL-Fatigue, EQ-5D-5L, MGFA, PGI-C, and PGI-S.

Example 15. Pediatric Study Design

This is an open-label, multicenter study to evaluate the PK, PD, safety, tolerability, and efficacy of study drug in pediatric subjects with gMG who have an insufficient clinical response to ongoing, stable standard of care therapy. A screening period of up to 28 days allows for sufficient time to perform screening evaluations and determine study eligibility. Total of 12 subjects proposed, 6 in each of the two age cohorts: Cohort 1) >=12 years to <18 Years; and Cohort 2) >=2 years to <12 years. The active treatment phase includes Cohorts 1 and 2, which can be unblinded and open to all male and female pediatric subjects meeting study specific inclusion and exclusion criteria. Cohort 1 enrolls adolescents (aged 12 to <18 years) to assess PK, PD, safety and activity of study drug treatment. Twelve weeks after all participants have entered Cohort 1, an interim analysis evaluates PK, PD, and safety data, which, if acceptable, initiates the study in Cohort 2 (participants aged 2 to <12 years). Once adolescents are enrolled, younger subjects aged 2 to <12 years can be enrolled. All subjects are administered study drug via IV infusion over 15-30 minutes every two weeks. Participants in Cohort 1 of the study receive a single 30 mg/kg loading dose followed by 15 mg/kg every 2 weeks [q2w]. Dosing for Cohort 2 is modeled based on all extant PK and PD data available (including adult data from Phase 1 to Phase 3 studies and adolescent data from Cohort 1 of this study) at the time of the interim analysis. A total of at least 12 subjects are studied, with at least 6 in each of the two age cohorts (adolescents and younger children). Study duration is 24 weeks, with an option to enter a long term extension (LTE) after study completion; subjects who discontinue early or do not enter the LTE after completing the study undergo a safety evaluation 8 weeks after terminating their enrollment. The LTE is expected to be approximately 104 weeks (~2 years) duration. All Cohort 1 participants in the LTE phase of the study have the option to receive nipocalimab infusion q2w (15 mg/kg) or q4w (30 mg/kg), or change background concomitant medications, based on the Investigator's discretion. Options for changing the Cohort 2 participant's dose and regimen during the LTE phase are modeled and based on all extant PK and PD data available (including adult data from Phase 1 to Phase 3 studies and adolescent data from Cohort 1 of this study) at the time of the interim analysis. No other dosing regimen should be used. Participants who discontinue early or do not enter the LTE after completing the study undergo a Safety Follow-up Visit 8 weeks after their last infusion of study intervention.

To assess the PK and PD of study drug in pediatric participants with gMG blood samples are collected at selected visits in this study. Serum samples for immunogenicity assessment are collected at selected visits in this study. Biomarker samples are collected to evaluate the mechanism of action of study drug or may help to identify population subgroups that respond differently to an intervention. The duration of the Active treatment Phase (24 weeks) is anticipated to be sufficient for the assessment of activity and safety based on nipocalimab's mechanism of action and results of the adult Phase 2 study demonstrating efficacy on the MG-ADL as early as Week 2 and sustained up to Day 57 (the primary assessment time point in the adult Phase 2 study). The maintenance of nipocalimab's effect, as well as the long-term safety of nipocalimab are further evaluated in the LTE phase. Safety assessments include collection of AEs and SAEs, use of concomitant medications, clinical laboratory testing (including chemistry, hematology, lipid profiles, urinalysis, and testing for total serum IgG and vaccine titers to diphtheria/tetanus), ECGs, vital signs, physical examinations and Tanner staging. Urine pregnancy testing is performed only for girls of childbearing potential. In addition, the emergence of suicidal ideation is assessed using the Columbia-Suicide Severity Rating Scale (C-SSRS). Severe or serious infections, events of hypoalbuminemia (<20 g/L), and opportunistic infections are considered adverse events of special interest (AESI).

Example 16. Nipocalimab is Safe and Well-Tolerated in Pediatric Patients with gMG A pediatric subject is evaluated, prior to treatment with nipocalimab, utilizing one or more of: physical examination, C-SSRS, vital signs, 12-lead ECG, urinalysis. Additionally, blood and serum is collected for exploratory biomarker analysis, Ig type analysis, and clinical laboratory assessments. A subject with myasthenia gravis or a subject with gMG who have an insufficient clinical response to ongoing, stable standard of care therapy is evaluated utilizing physical examination, C-SSRS, vital signs, 12-lead ECG, urinalysis, blood and serum assessment tests prior to treatment with nipocalimab to generate baseline scores. The subject is administered nipocalimab at a single dose, or a loading dose and a maintenance dose every 2 weeks for 24 weeks. After 24 weeks, and throughout the study, the subject is evaluated for changes in vital signs, clinical laboratory values, and C-SSRS score.

Example 17. Modeling of Intravenous Dosing for Use in Pediatric Patients

Various dosing regimens for M281 are modeled based on clinical data from adolescent patients. The impact of various dosing regimens on Myasthenia Gravis Activities of Daily Living (MG-ADL) is modeled. Among the doses modeled are: about 5 mg/kg, about 10 mg/kg, about 15 mg/kg, about 20 mg/kg, about 25 mg/kg, about 30 mg/kg, about 40 mg/kg, about 45 mg/kg, about 50 mg/kg, about 55 mg/kg, about 60 mg/kg. Based on this modeling, the dosing regimen for the younger patients is derived.

Example 18. Treatment of Myasthenia Gravis in Pediatric Patients with an Anti-FcRn Antibody Leads to Change from Baseline on MG-ADL Scale A pediatric subject is evaluated, prior to treatment with nipocalimab, utilizing Myasthenia Gravis-Activities of Daily Living (MG-ADL) scale. A subject with myasthenia gravis or a subject with gMG who have an insufficient clinical response to ongoing, stable standard of care therapy is evaluated utilizing MG-ADL prior to treatment with nipocalimab to generate a MG-ADL score. The subject is administered nipocalimab at a single dose, or a loading dose and a maintenance dose every 2 weeks for 24 weeks. After 24 weeks, and throughout the study at day 1, week 1, week 2, week 3, week 4, week 6, week 8, week 12, week 16, week 18, week 20, week 22, week 23, and week 24, the subject is evaluated for changes in MG-ADL score. After 24 weeks, and throughout the study, the subject is evaluated using MG-ADL scale and found to achieve change from baseline on MG-ADL scale.

Example 19. Treatment of Myasthenia Gravis in Pediatric Patients with an Anti-FcRn Antibody Leads to Change from Baseline on QMG and MG-QoL-15r Scales A pediatric subject is evaluated, prior to treatment with nipocalimab, utilizing QMG and MG-QoL-15r scales. A subject with myasthenia gravis or a subject with gMG who have an insufficient clinical response to ongoing, stable standard of care therapy is evaluated utilizing QMG and MG-QoL-15r prior to treatment with nipocalimab to generate a QMG and MG-QoL-15r score. The subject is administered nipocalimab at a single dose, or a loading dose and a maintenance dose every 2 weeks for 24 weeks. After 24 weeks, and throughout the study at day 1, week 2, week 4, week 8, week 12, week 16, week 20, week 22, and week 24, the subject is evaluated for changes in QMG and MG-QoL-15r scores. After 24 weeks, and throughout the study, the subject is evaluated using QMG and MG-QoL-15r scales and found to achieve change from baseline on QMG and MG-QoL-15r scales.

Example 20. Treatment of Myasthenia Gravis in Pediatric Patients with an Anti-FcRn Antibody Leads to Change from Baseline on Neuro-QoL-Pediatric Fatigue, EQ-5D-5L, MGFA, PGI-C, PGI-S, and PedsQL Scales A pediatric subject is evaluated, prior to treatment with nipocalimab, utilizing Neuro-QoL-Pediatric Fatigue (older cohort only), EQ-5D-5L (older cohort only), MGFA, PGI-C (older cohort only), PGI-S (older cohort only), and PedsQL scales. A pediatric subject with myasthenia gravis or a subject with gMG who have an insufficient clinical response to ongoing, stable standard of care therapy is evaluated utilizing Neuro-QoL-Fatigue (older cohort only), EQ-5D-5L (older cohort only), MGFA, PGI-C (older cohort only), PGI-S (older cohort only), and PedsQL scales prior to treatment with nipocalimab to generate a Neuro-QoL-Pediatric Fatigue (older cohort only), EQ-5D-5L (older cohort only), MGFA, PGI-C (older cohort only), PGI-S (older cohort only), and PedsQL score. The pediatric subject is administered nipocalimab at a single dose, or a loading dose and a maintenance dose every 2 weeks for 24 weeks. After 24 weeks, and throughout the study at day 1 (except for PGI-C), week 2, week 4, week 8, week 12, week 16, week 20, week 22, and week 24, the pediatric subject is evaluated for changes in Neuro-QoL-Pediatric Fatigue, EQ-5D-5L, PGI-C, PGI-S, and PedsQL scores. After 24 weeks, and throughout the study at day 1 and week 12, the pediatric subject is evaluated for changes in MGFA score. After 24 weeks, and throughout the study, the pediatric subject is evaluated using Neuro-QoL-Pediatric Fatigue, EQ-5D-5L, MGFA, PGI-C, PGI-S, and PedsQL scales and found to achieve change from baseline on Neuro-QoL-Pediatric Fatigue, EQ-5D-5L, MGFA, PGI-C, PGI-S, and PedsQL scales.

Example 21. Pediatric Dose Justification

Figure 10:
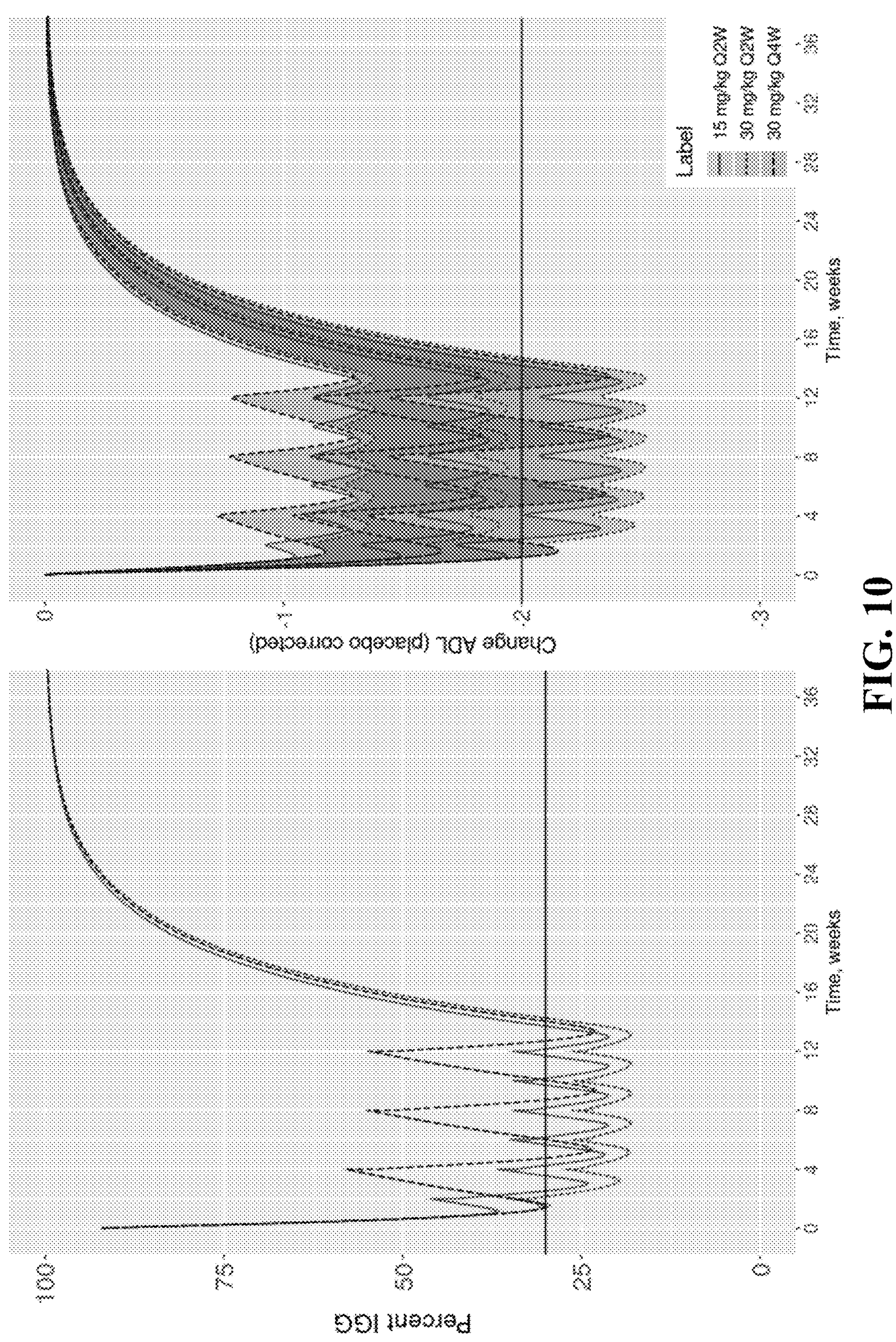
FIG. 10 is a graph showing the results of modeling designed to predict the IgG reduction and MG-ADL improvement with 15 mg/kg and 30 mg/kg q2w maintenance dosing in adult patients with gMG.
Figure 11:
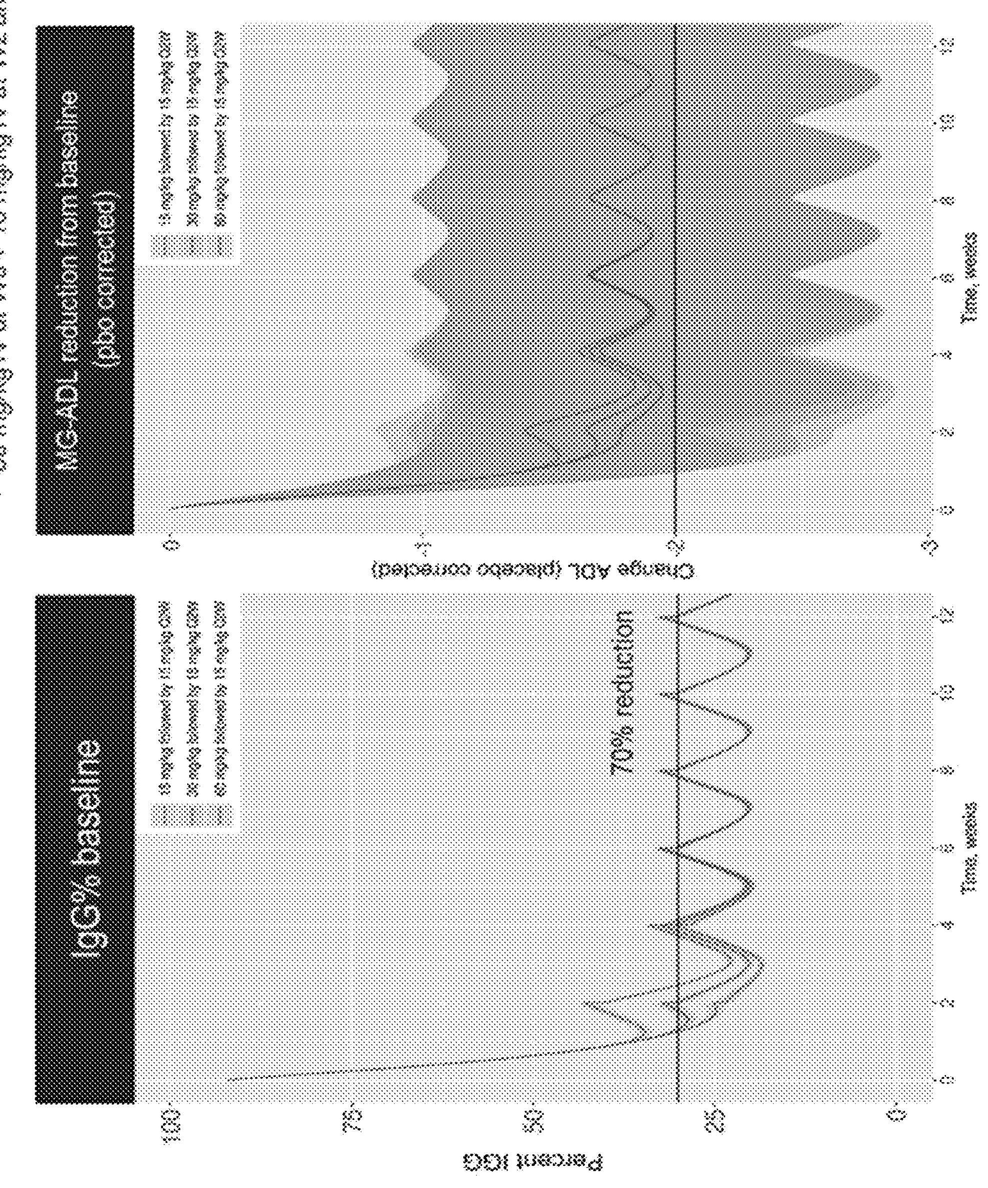
FIG. 11 is a graph showing the results of modeling designed to predict the IgG reduction and MG-ADL improvement with a 30 mg/kg loading dose in adult patients with gMG.

The proposed dose level and dosing regimen for Cohort 1 of this Phase 2/3 study in adolescent participants with gMG (ie, 30 mg/kg IV loading dose on Day 1 followed by 15 mg/kg IV q2w maintenance doses from Week 2) was based on the dose level and dosing regimen selected for the Phase 3 study in adult participants with gMG. The dose level and dosing regimen for the adult Phase 3 gMG study was based on observed data from the adult Phase 2 study in participants with gMG and extensive modeling and simulation of the dose response relationships for IgG and MG-ADL using data from adult Phase 1 and Phase 2 studies. Dosing for Cohort 2 of the present study, and as proposed in Example 15, is modeled based on all extant PK and PD data available (including adult data from Phase 1 to Phase 3 studies and adolescent data from Cohort 1 of the present study) at the time of the interim analysis. In the adult Phase 2 gMG study, rapid, dose-dependent IgG lowering was observed one week after the initial dose in all dose groups, with maximal IgG lowering achieved at Week 2 in the 60 mg/kg single dose and 60 mg/kg q2w groups. Dose-dependent improvements in MG-ADL scores were also observed, suggesting a correlation between IgG lowering and MG-ADL score improvement. Importantly, nipocalimab was generally well tolerated across all dose groups. Population PK/PD/efficacy modeling analyses were conducted using data obtained from nipocalimab adult Phase 1 and 2 studies to evaluate the relationship between PK, IgG lowering, and MG-ADL, in addition to other efficacy and safety endpoints (including serum albumin and cholesterol). The results indicated that the q2w dosing interval would provide more sustained IgG lowering and MG-ADL reduction at all simulated dose levels when compared with the q4w dosing interval. While modeling and simulation suggested numerical differences in IgG lowering and MG-ADL reduction between the 15 and 30 mg/kg q2w dosing regimens (the model-predicted mean IgG lowering is 73.8% versus 79.4%, respectively), the additional 5.6% IgG reduction with 30 mg/kg q2w translates to minimal additional MG-ADL improvement at steady-state trough beyond the improvement expected with 15 mg/kg q2w (FIG. 10). Therefore, the 15 mg/kg q2w dose regimen is selected as the single maintenance dose regimen to be studied for the adult Phase 3 gMG study since this is a rare disease with high unmet need. Lower doses likely result in suboptimal efficacy, while higher doses may not yield much difference in efficacy as predicted for gMG. The predicted exposure with a 30 mg/kg IV loading dose on Day 1 followed by 15 mg/kg IV q2w maintenance doses is well below the PK exposure observed from the 60 mg/kg q2w dosing regimen in the adult Phase 2 gMG study, which was generally well-tolerated based on the currently available safety data. The dosing regimen planned for the adult Phase 3 gMG study is expected to have an average of <20% albumin lowering and <20% total cholesterol increase at steady state. The magnitudes of albumin reduction and total cholesterol increase are not expected to be clinically significant and are less than those observed in prior adult studies with 30 mg/kg IV weekly or 60 mg/kg IV q2w dose regimens. Therefore, the proposed dose for the adult Phase 3 gMG study is expected to be safe and well tolerated. To propose the dose regimen for adolescent participants with gMG, a population PK/receptor occupancy (RO)/IgG model was developed using data from adults and the model was adapted for dose selection in pediatric participants with gMG. Based on data from literature, the adapted model accounted for 1) lower clearance (CL) and volume of distribution (V) in pediatric patients: the CL and V were scaled by body weight according to allometry; and 2) age and/or weight-dependent FcRn and IgG at baseline in pediatric patients: the FcRn and IgG were scaled by age and/or weight (Hardiansyah 2018). The results from the model-based simulation demonstrated comparable PK and IgG profiles between adolescent and adult patients with gMG when treated with the proposed dose and dosing regimen (FIG. 11). Therefore, the dose and dosing regimen selected for the adult Phase 3 gMG study are also used for Cohort 1 of this study in adolescent patients 12 to <18 years of age and no dose adjustment is needed. An interim analysis is performed to evaluate the PK, PD, and safety data after adolescent participants in Cohort 1 complete their first 12 weeks of treatment with nipocalimab. The dose regimen for children (2 to <12 years of age) in Cohort 2 is selected based on PK-PD modeling and simulation using all extant PK and PD data (including adult data from Phase 1 to Phase 3 studies and adolescent data from Cohort 1 of this study) available at the time of interim analysis. In the interim PK-PD modeling and simulation, the CL and V are scaled by body weight or body surface area (BSA) and the FcRn and IgG will be scaled by age, weight, or BSA. Depending on the results from interim analysis, dose adjustment may be needed for children in Cohort 2.

The embodiments and examples provided herein demonstrate that an anti-FcRn antibody, such as, but not limited to, M281 is effective to treat myasthenia gravis as measured one or more of the indices and outcomes as provided for herein.

The disclosures of each and every patent, patent application, and publication cited herein are hereby incorporated herein by reference in their entirety. While various embodiments have been disclosed with reference to specific aspects, it is apparent that other aspects and variations of these embodiments may be devised by others skilled in the art without departing from the true spirit and scope of the embodiments. The appended claims are intended to be construed to include all such aspects and equivalent variations.

The invention claimed is:

1. A method of treating myasthenia gravis (MG) in a patient in need thereof, the method comprising:

intravenously administering an initial loading dose of about 30 mg/kg of an anti-FcRn antibody followed by intravenously administering a maintenance dose of about 15 mg/kg of the anti-FcRn antibody, wherein the anti-FcRn antibody comprises:

a heavy chain comprising a HCDR1 of SEQ ID NO: 6, a HCDR2 of SEQ ID NO: 7, and a HCDR3 of SEQ ID NO: 8; and a light chain comprising a LCDR1 of SEQ ID NO: 3, a LCDR2 of SEQ ID NO: 4, and a LCDR3 of SEQ ID NO: 5;

wherein the initial loading dose is administered as a single dose;

wherein the maintenance dose is administered 2 weeks after the administration of the initial loading dose and every 2 weeks thereafter;

wherein the patient achieves at least 3 points reduction from baseline in MG activity of daily living profile (MG-ADL) score and at least 4 points reduction from baseline in quantitative MG (QMG) score following said administration of the anti-FcRn antibody by 24 weeks from the initial loading dose;

wherein an increase in levels of total cholesterol or low-density lipoprotein (LDL) in the patient as compared to the levels prior to the administration of the anti-FcRn antibody is at most 10% by 24 weeks from the initial loading dose.

2. The method of claim 1, wherein the heavy chain comprises an amino acid sequence having at least 95% identity to the sequence of SEQ ID NO: 2 and the light chain comprises an amino acid sequence having at least 95% identity to the sequence of SEQ ID NO: 1.

3. The method of claim 1, wherein the heavy chain comprises the amino acid sequence of SEQ ID NO: 2 and the light chain comprises the amino acid sequence of SEQ ID NO: 1.

4. The method of claim 1, wherein the heavy chain comprises a variable region heavy chain comprising the amino acid sequence of SEQ ID NO: 10 and the light chain comprises a variable region light chain comprising the amino acid sequence of SEQ ID NO: 9.

5. The method of claim 1, wherein:

the initial loading dose is infused into the patient in about 30 minutes to about 90 minutes; and the maintenance dose is infused into the patient in about 15 to about 60 minutes.

6. The method of claim 1, further comprising measuring serum albumin, wherein administering the anti-FcRn antibody reduces serum albumin by at most 18%, at most 16%, at most 14%, at most 12%, at most 10%, at most 8%, at most 6%, at most 4%, or at most 2% of baseline of serum albumin.

7. The method of claim 1, further comprising measuring serum autoantibodies, wherein administering the anti-FcRn antibody reduces serum autoantibodies, and wherein:

the autoantibodies are selected from the group consisting of: anti-acetylcholine receptors (AChRs), anti-musclespecific kinase (MuSK) anti-low-density lipoprotein receptor-related protein 4 (LRP4), anti-agrin, anti-titin, anti-Kv1.4, anti-ryanodine receptors, anti-collagen Q, anti-cortactin, and combinations thereof; and the reduction is by at least 95%, at least 90%, at least 85%, at least 80%, at least 75%, at least 50%, or at least 25% of baseline serum autoantibodies.

8. The method of claim 7, wherein administering the anti-FcRn antibody reduces anti-AChR antibodies by at least 95%, at least 90%, at least 85%, at least 80%, at least 75%, at least 50%, or at least 25% of baseline anti-AChR antibodies.

9. The method of claim 7, wherein administering the anti-FcRn antibody reduces anti-MuSK antibodies by at least 95%, at least 90%, at least 85%, at least 80%, at least 75%, at least 50%, or at least 25% of baseline anti-MuSK antibodies.

10. A method of treating myasthenia gravis (MG) in a patient in need thereof comprising:

intravenously administering an initial loading dose of about 30 mg/kg of an anti-FcRn antibody followed by intravenously administering a maintenance dose of about 15 mg/kg of the anti-FcRn antibody; and measuring levels of total cholesterol or calculated low-density lipoprotein (LDL) in the patient;

wherein the anti-FcRn antibody comprises:

a heavy chain comprising a HCDR1 of SEQ ID NO: 6, a HCDR2 of SEQ ID NO: 7, and a HCDR3 of SEQ ID NO: 8; and a light chain comprising a LCDR1 of SEQ ID NO: 3, a LCDR2 of SEQ ID NO: 4, and a LCDR3 of SEQ ID NO: 5;

wherein the initial loading dose is administered as a single dose;

wherein the maintenance dose is administered 2 weeks after the administration of the initial loading dose and every 2 weeks thereafter;

wherein the patient achieves at least 3 points reduction from baseline in MG activity of daily living profile (MG-ADL) score and at least 4 points reduction from baseline in quantitative MG (QMG) score following said administration of the anti-FcRn antibody by 24 weeks from the initial loading dose;

wherein an increase in levels of total cholesterol or low-density lipoprotein (LDL) in the patient as compared to the levels prior to the administration of the anti-FcRn antibody is at most by 24 weeks 10% from the initial loading dose.

11. The method of claim 1, further comprising measuring serum IgG, and wherein administering the anti-FcRn antibody reduces serum IgG in the patient by at least 10%, at least 20%, at least 30%, at least 40%, at least 50%, at least 60%, at least 70%, at least 80%, or at least 90% of baseline serum IgG following said administration of the anti-FcRn antibody.

12. The method of claim 11, wherein the serum IgG is IgG1, IgG2, IgG3, or IgG4, or any combination thereof, and wherein the reduction is by at least 20% of baseline, or at least 30% of baseline.

13. The method of claim 12, wherein the reduction is by at least 70% of baseline.

14. The method of claim 1, wherein the patient is 18 years of age or older.

15. The method of claim 1, wherein the patient is seropositive for anti-acetylcholine receptor (AChR) autoantibodies, anti-muscle-specific kinase (MuSK) autoantibodies, and/or anti-low-density lipoprotein receptor-related protein 4 (LRP4) antibodies, or any combination thereof.

16. The method of claim 15, wherein the patient is seropositive for anti-AChR autoantibodies.

17. The method of claim 15, wherein the patient is seropositive for anti-MuSK autoantibodies.

18. The method of claim 15, wherein the patient is seropositive for anti-LRP4 antibodies.

* * * * *

SEQUENCE LISTING

```
<160> NUMBER OF SEQ ID NOS: 26

<210> SEQ ID NO 1
<211> LENGTH: 216
<212> TYPE: PRT
<213> ORGANISM: Artificial Sequence
<220> FEATURE:
<223> OTHER INFORMATION: synthetic sequence

<400> SEQUENCE: 1

Gln Ser Ala Leu Thr Gln Pro Ala Ser Val Ser Gly Ser Pro Gly Gln
1               5                   10                  15
```

```
Ser Ile Thr Ile Ser Cys Thr Gly Thr Gly Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Gly Asp Ser Glu Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Gly Ile Tyr Val Phe Gly Thr Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 2
<211> LENGTH: 445
<212> TYPE: PRT
<213> ORGANISM: Artificial Sequence
<220> FEATURE:
<223> OTHER INFORMATION: synthetic sequence

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Trp Val
        35                  40                  45

Ser Ser Ile Gly Ala Ser Gly Ser Gln Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445


<210> SEQ ID NO 3
<211> LENGTH: 14
<212> TYPE: PRT
<213> ORGANISM: Artificial Sequence
<220> FEATURE:
<223> OTHER INFORMATION: synthetic sequence

<400> SEQUENCE: 3

Thr Gly Thr Gly Ser Asp Val Gly Ser Tyr Asn Leu Val Ser
1               5                   10


<210> SEQ ID NO 4
<211> LENGTH: 7
<212> TYPE: PRT
<213> ORGANISM: Artificial Sequence
<220> FEATURE:
<223> OTHER INFORMATION: synthetic sequence

<400> SEQUENCE: 4

Gly Asp Ser Glu Arg Pro Ser
1               5
```

<210> SEQ ID NO 5
<211> LENGTH: 10
<212> TYPE: PRT
<213> ORGANISM: Artificial Sequence
<220> FEATURE:
<223> OTHER INFORMATION: synthetic sequence

<400> SEQUENCE: 5

```
Ser Ser Tyr Ala Gly Ser Gly Ile Tyr Val
1               5                   10
```

<210> SEQ ID NO 6
<211> LENGTH: 5
<212> TYPE: PRT
<213> ORGANISM: Artificial Sequence
<220> FEATURE:
<223> OTHER INFORMATION: synthetic sequence

<400> SEQUENCE: 6

```
Thr Tyr Ala Met Gly
1               5
```

<210> SEQ ID NO 7
<211> LENGTH: 14
<212> TYPE: PRT
<213> ORGANISM: Artificial Sequence
<220> FEATURE:
<223> OTHER INFORMATION: synthetic sequence

<400> SEQUENCE: 7

```
Ser Ile Gly Ala Ser Gly Ser Gln Thr Arg Tyr Ala Asp Ser
1               5                   10
```

<210> SEQ ID NO 8
<211> LENGTH: 7
<212> TYPE: PRT
<213> ORGANISM: Artificial Sequence
<220> FEATURE:
<223> OTHER INFORMATION: synthetic sequence

<400> SEQUENCE: 8

```
Leu Ala Ile Gly Asp Ser Tyr
1               5
```

<210> SEQ ID NO 9
<211> LENGTH: 110
<212> TYPE: PRT
<213> ORGANISM: Artificial Sequence
<220> FEATURE:
<223> OTHER INFORMATION: synthetic sequence

<400> SEQUENCE: 9

```
Gln Ser Ala Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Gly Asp Ser Glu Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
```

```
                85                  90                  95

Gly Ile Tyr Val Phe Gly Thr Gly Thr Lys Val Thr Val Leu
            100                 105                 110


<210> SEQ ID NO 10
<211> LENGTH: 116
<212> TYPE: PRT
<213> ORGANISM: Artificial Sequence
<220> FEATURE:
<223> OTHER INFORMATION: synthetic sequence

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Trp Val
        35                  40                  45

Ser Ser Ile Gly Ala Ser Gly Ser Gln Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser
        115


<210> SEQ ID NO 11

<400> SEQUENCE: 11

000


<210> SEQ ID NO 12
<211> LENGTH: 5
<212> TYPE: PRT
<213> ORGANISM: Artificial Sequence
<220> FEATURE:
<223> OTHER INFORMATION: synthetic sequence

<400> SEQUENCE: 12

Asn Tyr Ala Met Gly
1               5


<210> SEQ ID NO 13

<400> SEQUENCE: 13

000


<210> SEQ ID NO 14
<211> LENGTH: 14
<212> TYPE: PRT
<213> ORGANISM: Artificial Sequence
<220> FEATURE:
<223> OTHER INFORMATION: synthetic sequence

<400> SEQUENCE: 14

Ser Ile Gly Ala Ser Gly Ala Gln Thr Arg Tyr Ala Asp Ser
1               5                   10
```

<210> SEQ ID NO 15
<211> LENGTH: 14
<212> TYPE: PRT
<213> ORGANISM: Artificial Sequence
<220> FEATURE:
<223> OTHER INFORMATION: synthetic sequence

<400> SEQUENCE: 15

Ser Ile Gly Ala Ser Gly Gly Gln Thr Arg Tyr Ala Asp Ser
1               5                   10

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23
<211> LENGTH: 445
<212> TYPE: PRT
<213> ORGANISM: Artificial Sequence
<220> FEATURE:
<223> OTHER INFORMATION: synthetic sequence

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Trp Val

```
        35                  40                  45

Ser Ser Ile Gly Ser Ser Gly Ala Gln Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445
```

<210> SEQ ID NO 24

<211> LENGTH: 445
<212> TYPE: PRT
<213> ORGANISM: Artificial Sequence
<220> FEATURE:
<223> OTHER INFORMATION: synthetic sequence

<400> SEQUENCE: 24

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Gly Trp Val Arg Gln Ala Pro Gly Lys Gly Leu Glu Trp Val
        35                  40                  45

Ser Ser Ile Gly Ala Ser Gly Ser Gln Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380
```

```
Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445


<210> SEQ ID NO 25
<211> LENGTH: 445
<212> TYPE: PRT
<213> ORGANISM: Artificial Sequence
<220> FEATURE:
<223> OTHER INFORMATION: synthetic sequence

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Val Arg Gln Ala Pro Gly Lys Gly Leu Glu Trp Val
        35                  40                  45

Ser Ser Ile Gly Ala Ser Gly Ala Gln Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445


<210> SEQ ID NO 26
<211> LENGTH: 445
<212> TYPE: PRT
<213> ORGANISM: Artificial Sequence
<220> FEATURE:
<223> OTHER INFORMATION: synthetic sequence

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Trp Val
        35                  40                  45

Ser Ser Ile Gly Ala Ser Gly Gly Gln Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220
```

-continued

```
Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445
```